US012617852B2

(12) United States Patent
Lin et al.

(10) Patent No.: US 12,617,852 B2
(45) Date of Patent: May 5, 2026

(54) PVRIG BINDING PROTEIN AND ITS MEDICAL USES

(71) Applicants: Jiangsu Hengrui Pharmaceuticals Co., Ltd., Jiangsu (CN); Shanghai Shengdi Pharmaceutical Co., Ltd., Shanghai (CN)

(72) Inventors: Yuan Lin, Jiangsu (CN); Kan Lin, Jiangsu (CN); Xinsheng Jin, Jiangsu (CN); Man Zhang, Jiangsu (CN); Cheng Liao, Jiangsu (CN)

(73) Assignees: Jiangsu Hengrui Pharmaceuticals Co., Ltd., Lianyungang (CN); SHANGHAI SHENGDI PHARMACEUTICAL CO., LTD., Shanghai (CN)

( * ) Notice: Subject to any disclaimer, the term of this patent is extended or adjusted under 35 U.S.C. 154(b) by 815 days.

(21) Appl. No.: 17/905,694

(22) PCT Filed: Mar. 12, 2021

(86) PCT No.: PCT/CN2021/080470
§ 371 (c)(1),
(2) Date: Sep. 6, 2022

(87) PCT Pub. No.: WO2021/180205
PCT Pub. Date: Sep. 16, 2021

(65) Prior Publication Data
US 2024/0043530 A1 Feb. 8, 2024

(30) Foreign Application Priority Data
Mar. 13, 2020 (CN) ......................... 202010174835.4

(51) Int. Cl.
*C07K 16/28* (2006.01)
(52) U.S. Cl.
CPC ...... *C07K 16/2803* (2013.01); *C07K 2317/31* (2013.01); *C07K 2317/569* (2013.01)
(58) Field of Classification Search
CPC ...................... C07K 2317/565; C07K 16/2803
USPC ................................................... 424/135.1
See application file for complete search history.

(56) References Cited

U.S. PATENT DOCUMENTS

| | | | |
|---|---|---|---|
| 2016/0244521 A1 | 8/2016 | White et al. | |
| 2018/0169238 A1 | 6/2018 | White et al. | |
| 2019/0010246 A1 | 1/2019 | Liang et al. | |
| 2024/0343803 A1* | 10/2024 | Zhao | A61P 35/00 |
| 2024/0376204 A1* | 11/2024 | Cao | C07K 16/28 |
| 2024/0376207 A1* | 11/2024 | Yang | A61K 39/39591 |

FOREIGN PATENT DOCUMENTS

| | | |
|---|---|---|
| CN | 107580500 A | 1/2018 |
| CN | 110088132 A | 8/2019 |
| CN | 110799213 A | 2/2020 |
| WO | 2016134335 A9 | 8/2016 |
| WO | 2017066714 A1 | 4/2017 |
| WO | 2019232484 A1 | 12/2019 |
| WO | 2023040940 * | 3/2023 |
| WO | 2023040945 * | 3/2023 |

OTHER PUBLICATIONS

Lin et al (Mol Cancer Ther (2025) 24 (5): 664-677).*
Frenkel et al (Exp Hematol. Mar. 2025:143:104696; Epub Dec. 1, 2024).*
Hansen et al (Cancer Immunology, Immunotherapy (2021) 70:3525-3540).*
Lin et al (Mol Cancer Ther 2025;24:664-77).*
Xue et al (Meeting Abstract: 2024 ASCO Annual Meeting I; Developmental Therapeutics—Immunotherapy May 29, 2024; J Clin Oncol 42, e14695(2024) vol. 42, No. 16_suppl DOI: 10.1200/JCO.2024.42.16_suppl.e14695; Abstract).*
Sanchez-Correa, Beatriz et al. "DNAM-1 and the TIGIT/PVRIG/TACTILE Axis:Novel Immune Checkpoints for Natural Killer Cell-Based Cancer Immunotherapy," Cancers, vol. 11, issue 6, article No. 877 (Jun. 23, 2019) 15 pages.
Jagannathan, Sujatha et al. "Translational plasticity facilitates the accumulation of nonsense genetic variants in the human population," Genome Research, vol. 26 (2016) pp. 1639-1650.
International Search Report (Form PCT/ISA/210) for International Patent Application No. PCT/CN2021/080470, issued from the International Searching Authority, date of mailing Jun. 10, 2021, 16 pages.
Written Opinion of the International Searching Authority (Form PCT/ISA/237) for International Patent Application No. PCT/CN2021/080470, issued from the International Searching Authority, date of mailing Jun. 10, 2021, 8 pages.
International Preliminary Report on Patentability (Form PCT/IB/373) for International Patent Application No. PCT/CN2021/080470, issued from the International Searching Authority, date of mailing Sep. 6, 2022, 5 pages.

* cited by examiner

*Primary Examiner* — Lynn A Bristol
(74) *Attorney, Agent, or Firm* — Ice Miller LLP

(57) ABSTRACT

A PVRIG binding protein and its medical uses. Specifically, an anti-PVRIG single-domain antibody and an anti-PVRIG and -TIGIT bispecific antibody, pharmaceutical compositions comprising the antibodies, a method for treating cancer, and pharmaceutical uses.

22 Claims, 11 Drawing Sheets
Specification includes a Sequence Listing.

PVRIG BINDING PROTEIN AND ITS MEDICAL USES

CROSS-REFERENCE TO RELATED APPLICATIONS

This application is a Section 371 of International Application No. PCT/CN2021/080470, filed on Mar. 12, 2021, which published in the Chinese language on Sep. 16, 2021, under International Publication No. WO 2021/180205 A1, which claims priority to Chinese Patent Application No. CN 202010174835.4 filed on Mar. 13, 2020. Each disclosure is incorporated herein by reference in its entirety.

REFERENCE TO SEQUENCE LISTING SUBMITTED ELECTRONICALLY

This application contains a sequence listing that is submitted electronically via EFS-Web as an ASCII formatted sequence listing with a file name "065827-6US1 Update ST25-v2" and a creation date of Nov. 18, 2025 and having a size of 147,726 bytes. The sequence listing, submitted via EFS-Web, is part of the specification and is herein incorporated by reference in its entirety.

TECHNICAL FIELD

The present disclosure relates to a PVRIG binding protein, e.g., an anti-PVRIG antibody and a bispecific antibody formed thereby together with anti-TIGIT antibody, and use thereof as a medicament for treating cancer.

BACKGROUND

Cancer is the greatest health challenge facing human society for a long term today. Traditional therapies such as surgery, chemotherapy and radiotherapy have shown little efficacy in treating disseminated solid tumors. Tumor immunotherapy is a hot spot in the field of tumor treatment, where tumor immunotherapy of T cells is in its central position. The tumor immunotherapy features fully utilizing and mobilizing killer T cells in a tumor patient to kill the tumor, and it is probably the most effective and the safest way to treat tumors. Tumor immunotherapy currently exhibits great promise for the treatment of several different types of cancers, including disseminated metastatic tumors.

The activation of T cells in humans adopts a system of two signaling pathways. In addition to providing the first signal to T cells by presenting MHC-antigen peptides via antigen presenting cells (APCs), a series of co-stimulatory molecules are also needed to provide the second signal, thereby enabling the T cells to generate normal immune response. This dual-signaling pathway system plays a crucial role in the balance of the immune system in vivo, and it strictly regulates the body's generation of different immune responses to self and non-self antigens. If the second signal provided by the co-stimulatory molecules is absent, there will be T cell non-response or sustained specific immune response, resulting in tolerance. Thus, the second signaling pathway plays a very critical regulatory role throughout the body's immune response.

PVRIG, also known as CD112R, is a protein expressed on the cell surface and belongs to the B7/CD28 superfamily, just like TIGIT, CD96, CD226, etc., and it plays an important role in the immune system. It comprises an extracellular region, a transmembrane region and an intracellular region. When its ligand PVRL2 (also known as CD112) binds to PVRIG, the ITIM domain of PVRIG intracellular region will be activated, thus enabling PVRIG to play the role of immunosuppression.

PVRIG is mainly expressed on the surface of CD4$^+$ T cells, CD8$^+$ T cells and NK cells. PVRIG and its ligand PVRL2 are highly expressed in many solid tumors, including lung cancer, breast cancer, ovarian cancer, renal cancer, gastric cancer, endometrial cancer, head and neck cancer, and the like. The expression of PVRIG in these cancers is highly correlated with TIGIT and PD-1. Similar to PD-1 and TIGIT, PVRIG-positive T cells are also Eomes-positive and Tbet-negative, indicating that PVRIG is associated with T cell depletion. Thus, PVRIG may represent a new immune checkpoint in addition to PD-1 and TIGIT and plays a redundancy role. In vitro cell experiments and mouse models show that the knockout or inhibition of mouse PVRIG can effectively inhibit the growth of tumors and generate coordination action with PD-1 and TIGIT inhibitors.

Another target of interest, TIGIT, is highly expressed on lymphocytes, including tumor infiltrating lymphocytes (TILs) and Treg infiltrating different types of tumors. It has been proved that engagement of TIGIT signaling to its cognate ligand PVR (also known as CD155) directly suppresses NK cell cytotoxicity through its cytoplasmic ITIM domain. PVR is also widely expressed in tumors, suggesting that the TIGIT-PVR signaling axis may be a dominant immune escape mechanism for cancer.

However, no PVRIG/TIGIT bispecific antibody drug has entered the clinic trial phase at present. COM701 by Compugen is the first humanized hybridoma antibody against PVRIG in the world approved by FDA to enter the clinic trial phase, and it is currently in phase I clinical stage and used for treating cancer. Surface Oncology is also developing an anti-PVRIG antibody, SRF-813. Anti-TIGIT antibodies include tiragolumab by Genentech, BMS-986207 developed by Ono Pharmaceutical in cooperation with BMS, MK-7684 by MSD, EOS-884448 by iTeos Therapeutics, and AB-154 by Arcus Biosciences, all in phase II clinical stage.

There remains a lack in the art of high-affinity, high-selectivity and high-bioactivity anti-PVRIG antibodies and anti-PVRIG/TIGIT bispecific antibodies capable of inhibiting cancer or tumor growth in vivo, and the present disclosure aims to provide such antibodies that activate immunity by blocking the inhibitory pathways of PVRIG and/or TIGIT to treat cancer.

SUMMARY

The present disclosure provides a PVRIG binding protein, an anti-PVRIG antibody (e.g., VHH) and a bispecific antibody formed thereby together with an anti-TIGIT antibody, as well as an encoding nucleic acid, a vector, a host cell, a pharmaceutical composition, a method for treating cancer and pharmaceutical use thereof.

In a first aspect, the present disclosure provides a PVRIG binding protein or an anti-PVRIG antibody.

In some embodiments, the PVRIG binding protein comprises at least one immunoglobulin single variable domain comprising three complementarity determining regions, a CDR1, a CDR2 and a CDR3, wherein:

the CDR1 is selected from the group consisting of an amino acid sequence set forth in any one of SEQ ID NOs: 7. 10, 13, 16, 19, 22, 25, 28, 31, 34, 37, 40, 43, 46, 49, 52, 55, 58, 61 and 64, and an amino acid sequence having 3, 2, 1 or more amino acid differences compared thereto, and/or the CDR2 is selected from the group consisting of an amino acid sequence set forth in any one of SEQ ID NOs: 8, 11, 14, 17, 20, 23, 26, 29, 32, 35, 38, 41, 44, 47, 50, 53, 56, 59, 62 and 65, and an amino acid sequence having 3, 2, 1 or more amino acid differences compared thereto, and/or the CDR3 is selected from the group consisting of an amino acid sequence set forth in any one of SEQ ID NOs: 9, 12, 15, 18, 21, 24, 27, 30, 33, 36, 39, 42, 45, 48, 51, 54, 57, 60, 63, 66, 150 and 151, and an amino acid sequence having 3, 2, 1 or more amino acid differences compared thereto.

SEQ ID NOs: 7-21, 150 and 151 are based on Kabat numbering scheme, SEQ ID NOs: 22-36 are based on Chothia numbering scheme, SEQ ID NOs: 37-51 are based on IMGT numbering scheme, and SEQ ID NOs: 52-66 are based on AbM numbering scheme.

In some embodiments, the PVRIG binding protein comprises at least one immunoglobulin single variable domain comprising a CDR1, a CDR2 and a CDR3 in a sequence set forth in any one of SEQ ID NOs: 2 and 75-79, a CDR1, a CDR2 and a CDR3 in a sequence set forth in any one of SEQ ID NOs: 3 and 80-84, a CDR1, a CDR2 and a CDR3 in a sequence set forth in any one of SEQ ID NOs: 4 and 86-90, a CDR1, a CDR2 and a CDR3 in a sequence set forth in any one of SEQ ID NOs: 5 and 91-95, or a CDR1, a CDR2 and a CDR3 in a sequence set forth in any one of SEQ ID NOs: 6 and 96-100, wherein the CDR1, the CDR2 and the CDR3 are defined according to Kabat, IMGT, Chothia, AbM or Contact numbering system, and in some specific embodiments, the CDRs are determined according to the Kabat numbering scheme.

In some embodiments, according to the Kabat numbering scheme, the immunoglobulin single variable domain of the PVRIG binding protein comprises three complementarity determining regions, a CDR1, a CDR2, and a CDR3, wherein:

amino acid sequences of the CDR1, the CDR2 and the CDR3 are set forth in SEQ ID NOs: 7, 8 and 9, respectively;

amino acid sequences of the CDR1, the CDR2 and the CDR3 are set forth in SEQ ID NOs: 7, 8 and 150, respectively;

amino acid sequences of the CDR1, the CDR2 and the CDR3 are set forth in SEQ ID NOs: 10, 11 and 12, respectively;

amino acid sequences of the CDR1, the CDR2 and the CDR3 are set forth in SEQ ID NOs: 10, 11 and 151, respectively;

amino acid sequences of the CDR1, the CDR2 and the CDR3 are set forth in SEQ ID NOs: 13, 14 and 15, respectively;

amino acid sequences of the CDR1, the CDR2 and the CDR3 are set forth in SEQ ID NOs: 16, 17 and 18, respectively; or amino acid sequences of the CDR1, the CDR2 and the CDR3 are set forth in SEQ ID NOs: 19, 20 and 21, respectively.

In some embodiments, according to the Chothia numbering scheme, the immunoglobulin single variable domain of the PVRIG binding protein comprises three complementarity determining regions, a CDR1, a CDR2, and a CDR3, wherein:

amino acid sequences of the CDR1, the CDR2 and the CDR3 are set forth in SEQ ID NOs: 22, 23 and 24, respectively;

amino acid sequences of the CDR1, the CDR2 and the CDR3 are set forth in SEQ ID NOs: 25, 26 and 27, respectively;

amino acid sequences of the CDR1, the CDR2 and the CDR3 are set forth in SEQ ID NOs: 28, 29 and 30, respectively;

amino acid sequences of the CDR1, the CDR2 and the CDR3 are set forth in SEQ ID NOs: 31, 32 and 33, respectively; or amino acid sequences of the CDR1, the CDR2 and the CDR3 are set forth in SEQ ID NOs: 34, 35 and 36, respectively.

In some embodiments, according to the IMGT numbering scheme, the immunoglobulin single variable domain of the PVRIG binding protein comprises three complementarity determining regions, a CDR1, a CDR2, and a CDR3, wherein:

amino acid sequences of the CDR1, the CDR2 and the CDR3 are set forth in SEQ ID NOs: 37, 38 and 39, respectively;

amino acid sequences of the CDR1, the CDR2 and the CDR3 are set forth in SEQ ID NOs: 40, 41 and 42, respectively;

amino acid sequences of the CDR1, the CDR2 and the CDR3 are set forth in SEQ ID NOs: 43, 44 and 45, respectively;

amino acid sequences of the CDR1, the CDR2 and the CDR3 are set forth in SEQ ID NOs: 46, 47 and 48, respectively; or amino acid sequences of the CDR1, the CDR2 and the CDR3 are set forth in SEQ ID NOs: 49, 50 and 51, respectively.

In some embodiments, according to the AbM numbering scheme, the immunoglobulin single variable domain of the PVRIG binding protein comprises three complementarity determining regions, a CDR1, a CDR2, and a CDR3, wherein:

amino acid sequences of the CDR1, the CDR2 and the CDR3 are set forth in SEQ ID NOs: 52, 53 and 54, respectively;

amino acid sequences of the CDR1, the CDR2 and the CDR3 are set forth in SEQ ID NOs: 55, 56 and 57, respectively;

amino acid sequences of the CDR1, the CDR2 and the CDR3 are set forth in SEQ ID NOs: 58, 59 and 60, respectively;

amino acid sequences of the CDR1, the CDR2 and the CDR3 are set forth in SEQ ID NOs: 61, 62 and 63, respectively; or amino acid sequences of the CDR1, the CDR2 and the CDR3 are set forth in SEQ ID NOs: 64, 65 and 66, respectively.

In some embodiments, provided is a PVRIG binding protein comprising an immunoglobulin single variable domain comprising a CDR1, a CDR2 and a CDR3, wherein according to Kabat numbering scheme, amino acid sequences of the CDR1, the CDR2 and the CDR3 of the immunoglobulin single variable domain are set forth in SEQ ID NOs: 7, 8 and 9, respectively; or SEQ ID NOs: 7, 8 and 150, respectively; or SEQ ID NOs: 10, 11 and 12, respectively; or SEQ ID NOs: 10, 11 and 151, respectively; or SEQ ID NOs: 13, 14 and 15, respectively; or SEQ ID NOs: 16, 17 and 18, respectively; or SEQ ID NOs: 19, 20 and 21, respectively.

In some embodiments, the PVRIG binding protein of the present disclosure is an antibody or an antigen-binding fragment thereof, preferably a VHH antibody, more preferably a humanized and/or affinity-matured VHH antibody.

In some embodiments, an amino acid sequence of the immunoglobulin single variable domain of the PVRIG binding protein of the present disclosure is one set forth in any one of SEQ ID NOs: 2-6, or having at least 80%, at least 90%, at least 95%, at least 98% or at least 99% sequence identity thereto. In some embodiments, the PVRIG binding protein is a variant protein having 3, 2, 1 or more amino acid differences at the CDR1, and/or 3, 2, 1 or more amino acid differences at the CDR2, and/or 3, 2, 1 or more amino acid differences at the CDR3, of the PVRIG binding protein described above.

In some embodiments, provided is an anti-PVRIG antibody comprising the CDR1, the CDR2 and the CDR3 in the PVRIG binding protein described above. The antibody may be humanized and/or affinity-matured. In some specific embodiments, an amino acid sequence of the anti-PVRIG antibody is one set forth in any one of SEQ ID NOs: 2-6, 75-84 and 86-100 or having at least 80%, at least 90%, at least 95%, at least 98% or at least 99% sequence identity thereto. In some specific embodiments, the anti-PVRIG single-domain antibody is linked to an Fc region of human IgG1, IgG2, IgG3 or IgG4, e.g., linked to the Fc region of IgG4 with S228P, F234A, L235A and/or K447A mutations (e.g., as shown in SEQ ID NO: 101 or 153).

In some embodiments, the immunoglobulin single variable domain in the PVRIG binding protein of the present disclosure is a single-domain antibody (VHH), and in some specific embodiments, the VHH is a humanized and/or affinity-matured VHH.

In some embodiments, the PVRIG binding protein of the present disclosure comprises an antibody.

In some embodiments, the PVRIG binding protein of the present disclosure is an antibody (e.g., a VHH).

In some embodiments, the PVRIG binding protein of the present disclosure is a camelid antibody, a humanized antibody or a fully human antibody.

In some embodiments, the PVRIG binding protein of the present disclosure or the immunoglobulin single variable domain therein is a camelid antibody, wherein an amino acid sequence of the VHH is one set forth in any one of SEQ ID NOs: 2-6 or having at least 70%, at least 80%, at least 90%, at least 95%, at least 96%, at least 97%, at least 98% or at least 99% sequence identity thereto.

In some embodiments, the PVRIG binding protein of the present disclosure or the immunoglobulin single variable domain therein is a humanized antibody, and a framework region of the antibody is a heavy chain framework region of a human germline template, such as IGHV3-7, specifically such as IGHV3-7*01 or IGHV3-30*02.

In some specific embodiments, the amino acid sequence of the anti-PVRIG humanized antibody of the disclosure is one set forth in any one of SEQ ID NOs: 75-84 and 86-100 or having at least 70%, at least 80%, at least 90%, at least 95%, at least 96%, at least 97%, at least 98% or at least 99% sequence identity thereto.

In some embodiments, the PVRIG binding protein of the present disclosure comprises or is a humanized antibody comprising a heavy chain framework region of a human germline template.

In some embodiments, the heavy chain framework region of the human germline template is IGHV3-7*01 or IGHV3-30*02.

In some embodiments, the amino acid sequence of the immunoglobulin single variable domain of the humanized antibody is one set forth in any one of SEQ ID NOs: 75-84 and 86-100 or having at least 90%, at least 95%, at least 98% or at least 99% sequence identity thereto.

In some embodiments, the PVRIG binding protein of the present disclosure further comprises a human immunoglobulin Fc region, e.g., an Fc region of human IgG1, IgG2, IgG3 or IgG4. In some specific embodiments, the human immunoglobulin Fc region is the Fc region of human IgG4. In some specific embodiments, the human immunoglobulin Fc region is the Fc region of human IgG1. The Fc region may have mutations, such as amino acid mutations of S228P, F234A, L235A and/or K447A (e.g., as shown in SEQ ID NO: 101 or 153).

In some embodiments, in the PVRIG binding protein of the present disclosure, the immunoglobulin single variable domain capable of specifically binding to PVRIG is linked, directly or via a linker, to the immunoglobulin Fc region. The linker may be a non-functional amino acid sequence having 1-20, 1-30, 1-40, 1-50 or more amino acids in length and no secondary or higher structure. The linker may be a flexible linker, such as GS, GAP, ASGS (SEQ ID NO: 154), $G_4S$ (SEQ ID NO: 155), $(G_4S)_2$ (SEQ ID NO: 152), $(G_4S)_3$ (SEQ ID NO: 156), $(G_4S)_4$ (SEQ ID NO: 157), $(G_4S)_5$ (SEQ ID NO: 158), $(G_4S)_6$ (SEQ ID NO: 159), YGNGT (SEQ ID NO: 160), $(YGNGT)_2$ (SEQ ID NO: 161), $(YGNGT)_3$ (SEQ ID NO: 162), $(YGNGT)_4$ (SEQ ID NO: 163), $(YGNGT)_5$ (SEQ ID NO: 164) and $(YGNGT)_6$ (SEQ ID NO: 165).

In some specific embodiments, the Fc region in the PVRIG binding protein of the present disclosure allows the PVRIG binding protein to form a dimer molecule comprising two or four PVRIG binding domains. Such a PVRIG binding protein is also referred to as a bivalent or tetravalent PVRIG binding protein. The dimer is, for example, a homodimer. The PVRIG binding protein or the anti-PVRIG antibody of the present disclosure has at least one of the following characteristics:

(a) binding to PVRIG with a $K_D$ value of less than $1 \times 10^{-7}$ M;

(b) blocking the interaction of PVRIG with its ligand (e.g., PVRL2);

(c) relieving the inhibition of dendritic cells against T cells and activating the T cells;

(d) relieving the inhibition of tumor cells against NK cells; and (e) inhibiting tumor growth.

The PVRIG binding protein or the anti-PVRIG antibody of the present disclosure can bind to PVRIG with a $K_D$ value of less than $1 \times 10^{-7}$ M, less than $1 \times 10^{-8}$ M, less than $1 \times 10^{-9}$ M or less than $1 \times 10^{10}$ M.

The PVRIG binding protein or the anti-PVRIG antibody of the present disclosure is capable of inhibiting tumor growth by at least about 10%, at least about 20%, at least about 30%, at least about 40%, at least about 50%, at least about 60%, at least about 70% or at least about 80%.

The PVRIG binding protein or the anti-PVRIG antibody of the present disclosure can be monomeric, and/or PEGylated, and/or glycosylated, and/or albumin-conjugated or -fused, and/or Fc-fused, and/or hydroxyethylated, and/or de-O-glycosylated.

In a second aspect, the present disclosure provides a bispecific antibody against PVRIG. In some embodiments, provided is a bispecific antibody comprising a first antigen-binding domain and a second antigen-binding domain, wherein the first antigen-binding domain specifically binds to PVRIG.

In some embodiments, the first antigen-binding domain of the bispecific antibody of the present disclosure specifically binds to PVRIG, and the first antigen-binding domain comprises at least one immunoglobulin single variable domain (such as a VHH) comprising three complementarity determining regions, a CDR1, a CDR2 and a CDR3, wherein:

the CDR1 is selected from the group consisting of an amino acid sequence set forth in any one of SEQ ID NOs: 7. 10, 13, 16, 19, 22, 25, 28, 31, 34, 37, 40, 43, 46, 49, 52, 55, 58, 61 and 64, and an amino acid sequence having 3, 2, 1 or more amino acid differences compared thereto, and/or the CDR2 is selected from the group consisting of an amino acid sequence set forth in any one of SEQ ID NOs: 8, 11, 14, 17, 20, 23, 26, 29, 32, 35, 38, 41, 44, 47, 50, 53, 56, 59, 62 and 65, and an amino acid sequence having 3, 2, 1 or more amino acid differences compared thereto, and/or the CDR3 is selected from the group consisting of an amino acid sequence set forth in any one of SEQ ID NOs: 9, 12, 15, 18, 21, 24, 27, 30, 33, 36, 39, 42, 45, 48, 51, 54, 57, 60, 63, 66, 150 and 151, and an amino acid sequence having 3, 2, 1 or more amino acid differences compared thereto.

SEQ ID NOs: 7-21 are based on Kabat numbering scheme, SEQ ID NOs: 22-36 are based on Chothia numbering scheme, SEQ ID NOs: 37-51 are based on IMGT numbering scheme, and SEQ ID NOs: 52-66 are based on AbM numbering scheme.

In some embodiments, the first antigen-binding domain specifically binding to PVRIG in the bispecific antibody comprises at least one immunoglobulin single variable domain comprising a CDR1, a CDR2 and a CDR3 in a sequence set forth in any one of SEQ ID NOs: 2 and 75-79, a CDR1, a CDR2 and a CDR3 in a sequence set forth in any one of SEQ ID NOs: 3 and 80-84, a CDR1, a CDR2 and a CDR3 in a sequence set forth in any one of SEQ ID NOs: 4 and 86-90, a CDR1, a CDR2 and a CDR3 in a sequence set forth in any one of SEQ ID NOs: 5 and 91-95, or a CDR1, a CDR2 and a CDR3 in a sequence set forth in any one of SEQ ID NOs: 6 and 96-100, wherein the CDR1, the CDR2 and the CDR3 are defined according to Kabat, IMGT, Chothia, AbM or Contact numbering system, and in some specific embodiments, the CDRs are determined according to the Kabat numbering scheme.

In some specific embodiments, according to the Kabat numbering scheme, the first antigen-binding domain specifically binding to PVRIG (e.g., a VHH) comprises three complementarity determining regions, a CDR1, a CDR2 and a CDR3, wherein:

amino acid sequences of the CDR1, the CDR2 and the CDR3 are set forth in SEQ ID NOs: 7, 8 and 9, respectively;

amino acid sequences of the CDR1, the CDR2 and the CDR3 are set forth in SEQ ID NOs: 7, 8 and 150, respectively;

amino acid sequences of the CDR1, the CDR2 and the CDR3 are set forth in SEQ ID NOs: 10, 11 and 12, respectively;

amino acid sequences of the CDR1, the CDR2 and the CDR3 are set forth in SEQ ID NOs: 10, 11 and 151, respectively;

amino acid sequences of the CDR1, the CDR2 and the CDR3 are set forth in SEQ ID NOs: 13, 14 and 15, respectively;

amino acid sequences of the CDR1, the CDR2 and the CDR3 are set forth in SEQ ID NOs: 16, 17 and 18, respectively; or amino acid sequences of the CDR1, the CDR2 and the CDR3 are set forth in SEQ ID NOs: 19, 20 and 21, respectively.

In some specific embodiments, according to the Chothia numbering scheme, the first antigen-binding domain specifically binding to PVRIG (e.g., a VHH) comprises three complementarity determining regions, a CDR1, a CDR2 and a CDR3, wherein:

amino acid sequences of the CDR1, the CDR2 and the CDR3 are set forth in SEQ ID NOs: 22, 23 and 24, respectively;

amino acid sequences of the CDR1, the CDR2 and the CDR3 are set forth in SEQ ID NOs: 25, 26 and 27, respectively;

amino acid sequences of the CDR1, the CDR2 and the CDR3 are set forth in SEQ ID NOs: 28, 29 and 30, respectively;

amino acid sequences of the CDR1, the CDR2 and the CDR3 are set forth in SEQ ID NOs: 31, 32 and 33, respectively; or amino acid sequences of the CDR1, the CDR2 and the CDR3 are set forth in SEQ ID NOs: 34, 35 and 36, respectively.

In some specific embodiments, according to the IMGT numbering scheme, the first antigen-binding domain specifically binding to PVRIG (e.g., a VHH) comprises three complementarity determining regions, a CDR1, a CDR2 and a CDR3, wherein:

amino acid sequences of the CDR1, the CDR2 and the CDR3 are set forth in SEQ ID NOs: 37, 38 and 39, respectively;

amino acid sequences of the CDR1, the CDR2 and the CDR3 are set forth in SEQ ID NOs: 40, 41 and 42, respectively;

amino acid sequences of the CDR1, the CDR2 and the CDR3 are set forth in SEQ ID NOs: 43, 44 and 45, respectively;

amino acid sequences of the CDR1, the CDR2 and the CDR3 are set forth in SEQ ID NOs: 46, 47 and 48, respectively; or amino acid sequences of the CDR1, the CDR2 and the CDR3 are set forth in SEQ ID NOs: 49, 50 and 51, respectively.

In some specific embodiments, according to the AbM numbering scheme, the first antigen-binding domain specifically binding to PVRIG (e.g., a VHH) comprises three complementarity determining regions, a CDR1, a CDR2 and a CDR3, wherein:

amino acid sequences of the CDR1, the CDR2 and the CDR3 are set forth in SEQ ID NOs: 52, 53 and 54, respectively;

amino acid sequences of the CDR1, the CDR2 and the CDR3 are set forth in SEQ ID NOs: 55, 56 and 57, respectively;

amino acid sequences of the CDR1, the CDR2 and the CDR3 are set forth in SEQ ID NOs: 58, 59 and 60, respectively;

amino acid sequences of the CDR1, the CDR2 and the CDR3 are set forth in SEQ ID NOs: 61, 62 and 63, respectively; or amino acid sequences of the CDR1, the CDR2 and the CDR3 are set forth in SEQ ID NOs: 64, 65 and 66, respectively.

In some embodiments, the first antigen-binding domain (e.g., a VHH) of the bispecific antibody of the present disclosure comprises an amino acid sequence set forth in any one of SEQ ID NOs: 2-6, 75-84 and 86-100, or a sequence having at least 70%, at least 80%, at least 90%, at least 95%, at least 96%, at least 97%, at least 98% or at least 99% identity thereto.

In some embodiments, in the bispecific antibody of the present disclosure:

the first antigen-binding domain is a first antibody, which is a VHH;

the second antigen-binding domain is a second antibody comprising a heavy chain (HC) and a light chain (LC);

the VHH, as the first antibody, is located at N- and/or C-terminal of the HC or LC of the second antibody.

In some specific embodiments, the bispecific antibody of the present disclosure comprises 1 second antibody and 2 VHH first antibodies; the second antibody comprises two HCs and two LCs, and in the second antibody, a VH of one HC forms an antigen-binding site with a VL of one LC, and a VH of the other HC forms an antigen-binding site with a VL of the other LC.

In some specific embodiments, in the bispecific antibody of the present disclosure, one VHH first antibody is located at N-terminal of the HC or LC of the second antibody, and the other VHH first antibody is located at C-terminal of the HC or LC of the second antibody.

In some specific embodiments, in the bispecific antibody of the present disclosure, the VHH first antibodies are located at N-terminals of both HCs or both LCs, respectively, of the second antibody; or, the VHH first antibodies are located at C-terminals of both HCs or both LCs, respectively, of the second antibody.

In some specific embodiments, in the bispecific antibody of the present disclosure, the VHH first antibodies are located at N-terminals to the two HCs, respectively, of the first antibody; or, the VHH first antibodies are located at C-terminals of both HCs, respectively, of the first antibody.

In some specific embodiments, the first antibody of the present disclosure may be connected to 1, 2, 3, 4, 5, 6, 7 or 8 VHH second antibodies, which may be the same or different, may all be connected to the N-terminal of the HC of the first antibody, or may all be connected to the C-terminal of the HC of the first antibody, or may all be connected to the N-terminal of the LC of the first antibody, or may all be connected to the C-terminal of the LC of the first antibody, or may be connected to any combination of the N-terminal of the HC, the C-terminal of the HC, the N-terminal of the LC and the C-terminal of the LC.

In some specific embodiments, the VHH first antibody in the bispecific antibody of the present disclosure is linked, directly or via a linker, to the N-terminal or C-terminal of each HC of the second antibody. The linker is selected from the group consisting of amino acid sequences set forth in $(G_mS_n)_x$, $(GGNGT)_x$ (SEQ ID NO: 166) and $(YGNGT)_x$ (SEQ ID NO: 167), where m and n are independently selected from the group consisting of integers of 1-8 (e.g., 1, 2, 3, 4, 5, 6, 7 or 8), and x is independently selected from the group consisting of integers of 1-20 (e.g., 1, 2, 3, 4, 5, 6, 7, 8, 9, 10, 11, 12, 13, 14, 15, 16, 17, 18, 19 or 20). For example, the linker is an amino acid sequence set forth in $G_4S$ (SEQ ID NO: 155), $(G_4S)_2$ (SEQ ID NO: 152), $(G_4S)_3$ (SEQ ID NO: 156), $(G_4S)_4$ (SEQ ID NO: 157), $(G_4S)_5$ (SEQ ID NO: 158) or $(G_4S)_6$ (SEQ ID NO: 159).

In some embodiments, the HC of the second antibody of the bispecific antibody of the present disclosure comprises a heavy chain variable region (VH) and a heavy chain constant region (CH), and the LC comprises a light chain variable region (VL) and a light chain constant region (CL). The second antibody may be a full-length antibody.

In some embodiments, the HC of the second antibody of the bispecific antibody of the present disclosure is of IgG isotype (e.g., IgG1, IgG2, IgG3 or IgG4), such as of IgG1 isotype; and/or the LC of the second antibody is of Kappa isotype.

In some embodiments, the two HCs of the second antibody of the bispecific antibody of the present disclosure comprise identical CDRs and/or the two LCs comprise identical CDRs. In some specific embodiments, the two HCs of the second antibody comprise identical VH and/or the two LCs comprise identical VL. In some specific embodiments, the two HCs of the second antibody have identical amino acid sequences, and/or the two LCs have identical amino acid sequences.

In some embodiments, the two VHH first antibodies of the bispecific antibody of the present disclosure have identical or different amino acid sequences. For example, the two VHH first antibodies have identical amino acid sequences.

In some embodiments, the bispecific antibody of the present disclosure comprises two first polypeptide chains and two second polypeptide chains, where for each polypeptide chain: a) the first polypeptide chains each independently comprise the VHH first antibody and a heavy chain (HC) of the second antibody; and b) the second polypeptide chains each independently comprise a light chain (LC) of the second antibody; where the VHH is linked, via a linker, to the N-terminal and/or C-terminal of the HC of the first antibody. Or, i) the first polypeptide chains each independently comprise a heavy chain (HC) of the second antibody; and ii) the second polypeptide chains each independently comprise the VHH first antibody and a light chain (LC) of the second antibody; where the VHH is linked, directly or via a linker, to the N-terminal and/or C-terminal of the LC of the second antibody.

In some specific embodiments, the bispecific antibody of the present disclosure comprises two identical first polypeptide chains and two identical second polypeptide chains.

In some embodiments, the second antigen-binding domain of the bispecific antibody of the present disclosure is any anti-TIGIT antibody. TIGIT antibodies in WO2009126688, WO2014089113, WO2015009856, WO2015143343, WO2015174439, WO2016028656, WO2016106302, WO2017053748, WO2017030823, US20160176963, US20130251720, WO2019232484 and WO2019062832 are incorporated herein by reference in their entireties. For example, the TIGIT antibody may be any one of CPA·9·083·H4(S241P), CPA·9·086·H4(S241P), CHA·9·547·7·H4(S241P) and CHA·9·547·13·H4(S241P) (see WO2019232484).

In some embodiments, the second antigen-binding domain of the bispecific antibody of the present disclosure is the second antibody. The anti-TIGIT antibody in WO2019062832 is incorporated herein by reference in its entirety to be used as the second antibody. In the second antibody:

the heavy chain variable region comprises an HCDR1, an HCDR2 and an HCDR3 set forth in SEQ ID NOs: 115, 116 and 117, respectively, and the light chain variable region comprises an LCDR1, an LCDR2 and an LCDR3 set forth in SEQ ID NOs: 118, 119 and 120, respectively; or the heavy chain variable region comprises an HCDR1, an HCDR2 and an HCDR3 set forth in SEQ ID NOs: 121, 122 and 123, respectively, and the light chain variable region comprises an LCDR1, an LCDR2 and an LCDR3 set forth in SEQ ID NOs: 124, 125 and 126, respectively; or the heavy chain variable region comprises an HCDR1, an HCDR2 and an HCDR3 set forth in SEQ ID NOs: 127, 128 and 129, respectively, and the light chain variable region comprises an LCDR1, an LCDR2 and an LCDR3 set forth in SEQ ID NOs: 130, 131 and 132, respectively; or the heavy chain variable region comprises an HCDR1, an HCDR2 and an HCDR3 set forth in SEQ ID NOs: 133, 134 and 135, respectively, and the light chain variable region comprises an LCDR1, an LCDR2 and an LCDR3 set forth in SEQ ID NOs: 136, 137 and 138, respectively; or the heavy chain variable region comprises an HCDR1, an HCDR2 and an HCDR3 set forth in SEQ ID NOs: 139, 140 and 141, respectively, and the light chain variable region comprises an LCDR1, an LCDR2 and an LCDR3 set forth in SEQ ID NOs: 142, 143 and 144, respectively.

In some specific embodiments, the first antigen-binding domain or the first antibody (e.g., a VHH) in the bispecific antibody of the present disclosure comprises a CDR1, a CDR2 and a CDR3 set forth in SEQ ID NOs: 7, 8 and 9, respectively, or comprises a CDR1, a CDR2 and a CDR3 set forth in SEQ ID NOs: 7, 8 and 150, respectively; the heavy chain variable region of the second antigen-binding domain or the second antibody comprises an HCDR1, an HCDR2 and an HCDR3 set forth in SEQ ID NOs: 121, 122 and 123, respectively, and the light chain variable region comprises an LCDR1, an LCDR2 and an LCDR3 set forth in SEQ ID NOs: 124, 125 and 126, respectively.

In some specific embodiments, the first antigen-binding domain or the first antibody (e.g., a VHH) in the bispecific antibody of the present disclosure comprises a CDR1, a CDR2 and a CDR3 set forth in SEQ ID NOs: 10, 11 and 12, respectively, or comprises a CDR1, a CDR2 and a CDR3 set forth in SEQ ID NOs: 10, 11 and 151, respectively; the heavy chain variable region of the second antigen-binding domain or the second antibody comprises an HCDR1, an HCDR2 and an HCDR3 set forth in SEQ ID NOs: 121, 122 and 123, respectively, and the light chain variable region comprises an LCDR1, an LCDR2 and an LCDR3 set forth in SEQ ID NOs: 124, 125 and 126, respectively.

In some specific embodiments, the VHH first antibody in the bispecific antibody of the present disclosure comprises an amino acid sequence set forth in any one of SEQ ID NOs: 6, 79, 81, 92, 98 and 99 or an amino acid sequence having at least 70%, at least 80%, at least 90%, at least 95%, at least 96%, at least 97%, at least 98% or at least 99% sequence identity thereto; the second antibody comprises a VH set forth in any one of SEQ ID NOs: 145-147, a VL set forth in any one of SEQ ID NOs: 148-149, an HC set forth in SEQ ID NO: 102 and an LC set forth in SEQ ID NO: 103 or sequences having at least 70%, at least 80%, at least 90%, at least 95%, at least 96%, at least 97%, at least 98% or at least 99% sequence identity to the VH and HC or VL and LC.

In some specific embodiments, the bispecific antibody of the present disclosure comprises:

a first polypeptide set forth in SEQ ID NO: 104, and a second polypeptide set forth in SEQ ID NO: 103;

a first polypeptide set forth in SEQ ID NO: 105, and a second polypeptide set forth in SEQ ID NO: 103;

a first polypeptide set forth in SEQ ID NO: 102, and a second polypeptide set forth in SEQ ID NO: 106;

a first polypeptide set forth in SEQ ID NO: 102, and a second polypeptide set forth in SEQ ID NO: 107;

a first polypeptide set forth in any one of SEQ ID NOs: 108-112 and 114, and a second polypeptide set forth in SEQ ID NO: 103; or variants having at least 70%, at least 80%, at least 90%, at least 95%, at least 96%, at least 97%, at least 98% or at least 99% sequence identity to the first polypeptide chain and/or the second polypeptide chain described above.

In some embodiments, the PVRIG binding protein, the anti-PVRIG antibody and the bispecific antibody formed thereby together with the anti-TIGIT of the present disclosure have mutations in the Fc region, including one or more amino acid mutations selected from the group consisting of:

i) mutations that alter the number of cysteine residues in the hinge region of CH1 to facilitate assembly of the light and heavy chains or to increase or decrease the stability of the antibody;

ii) mutations that enhance binding to FcγRIIIa to result in enhanced ADCC and mutations that attenuate binding to FcγRIIb, such as 236A, 239D, 239E, 332E, 332D, 239D/332E, 267D, 267E, 328F, 267E/328F, 236A/332E, 239D/332E/330Y, 239D, 332E/330L, 299T, 297N or any combination thereof, iii) mutations that increase the biological half-life, such as T252L, T254S, T256F, 428L, 434A, 434S 428L/434S or any combination thereof;

iv) one or more amino acid mutations at positions 234, 235, 236, 237, 297, 318, 320 and 322, or any combination thereof, to alter the affinity of the antibody for an effector ligand while retaining the antigen-binding ability of the parent antibody;

v) one or more amino acid mutations at positions 329, 331 and 322, or any combination thereof, such that the antibody has altered C1q binding and/or the complement dependent cytotoxicity (CDC) is reduced or eliminated;

vi) one or more amino acid mutations within 231-239 or any combination thereof, such that the antibody's ability to fix complement is altered;

vii) one or more amino acid mutations in 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 and 439, or any combination thereof, to increase the capacity for ADCC and/or to increase the affinity of the antibody for the Fcγ receptor;

viii) amino acid mutations of S228P, F234A, L235A and/or K447A; and ix) amino acid mutations of S354C, E356D, M358 μL and/or T366W.

In some embodiments, provided are antibodies that compete for binding to the same epitope with the PVRIG binding protein, the PVRIG\TIGIT binding protein, the anti-PVRIG single-domain antibody, and the anti-PVRIG/TIGIT bispecific antibody of the present disclosure.

In some embodiments, the present disclosure provides a PVRIG/TIGIT binding protein comprising a first antigen-binding domain specifically binding to PVRIG and a second antigen-binding domain specifically binding to TIGIT, wherein the first antigen-binding domain specifically binding to PVRIG comprises an immunoglobulin single variable domain comprising:

a CDR1, a CDR2 and a CDR3 in a sequence set forth in any one of SEQ ID NOs: 3 and 80-84; or a CDR1, a CDR2 and a CDR3 in a sequence set forth in any one of SEQ ID NOs: 2 and 75-79; or a CDR1, a CDR2 and a CDR3 in a sequence set forth in any one of SEQ ID NOs: 4 and 86-90; or a CDR1, a CDR2 and a CDR3 in a sequence set forth in any one of SEQ ID NOs: 5 and 91-95; or a CDR1, a CDR2 and a CDR3 in a sequence set forth in any one of SEQ ID NOs: 6 and 96-100;

wherein the CDR1, the CDR2 and the CDR3 are defined according to Kabat, IMGT, Chothia, AbM or Contact numbering system.

According to the Kabat numbering system, amino acid sequences of the CDR1, the CDR2 and the CDR3 of the immunoglobulin single variable domain are set forth in SEQ ID NOs: 7, 8 and 9, respectively; or SEQ ID NOs: 7, 8 and 150, respectively; or SEQ ID NOs: 10, 11 and 12, respectively; or SEQ ID NOs: 10, 11 and 151, respectively; or SEQ ID NOs: 13, 14 and 15, respectively; or SEQ ID NOs: 16, 17 and 18, respectively; or SEQ ID NOs: 19, 20 and 21, respectively.

In specific embodiments, the first antigen-binding domain of the PVRIG/TIGIT binding protein comprises an amino acid sequence set forth in any one of SEQ ID NOs: 2-6, 75-84, and 86-100 or an amino acid sequence having at least 90%, at least 95%, at least 98% or at least 99% sequence identity thereto.

In specific embodiments, the second antigen-binding domain of the PVRIG/TIGIT binding protein comprises a heavy chain variable region (VH) and a light chain variable region (VL), wherein:

the heavy chain variable region comprises an HCDR1, an HCDR2 and an HCDR3 set forth in SEQ ID NOs: 115, 116 and 117, respectively, and the light chain variable region comprises an LCDR1, an LCDR2 and an LCDR3 set forth in SEQ ID NOs: 118, 119 and 120, respectively;

the heavy chain variable region comprises an HCDR1, an HCDR2 and an HCDR3 set forth in SEQ ID NOs: 121, 122 and 123, respectively, and the light chain variable region comprises an LCDR1, an LCDR2 and an LCDR3 set forth in SEQ ID NOs: 124, 125 and 126, respectively;

the heavy chain variable region comprises an HCDR1, an HCDR2 and an HCDR3 set forth in SEQ ID NOs: 127, 128 and 129, respectively, and the light chain variable region comprises an LCDR1, an LCDR2 and an LCDR3 set forth in SEQ ID NOs: 130, 131 and 132, respectively;

the heavy chain variable region comprises an HCDR1, an HCDR2 and an HCDR3 set forth in SEQ ID NOs: 133, 134 and 135, respectively, and the light chain variable region comprises an LCDR1, an LCDR2 and an LCDR3 set forth in SEQ ID NOs: 136, 137 and 138, respectively; or the heavy chain variable region comprises an HCDR1, an HCDR2 and an HCDR3 set forth in SEQ ID NOs: 139, 140 and 141, respectively, and the light chain variable region comprises an LCDR1, an LCDR2 and an LCDR3 set forth in SEQ ID NOs: 142, 143 and 144, respectively.

In specific embodiments, the second antigen-binding domain of the PVRIG/TIGIT binding protein comprises a full-length heavy chain (HC) and a full-length light chain (LC);

specifically, the full-length heavy chain is of IgG1 or IgG4 isotype, and the full-length light chain is of Kappa isotype;

more specifically, a sequence of the heavy chain is one set forth in SEQ ID NO: 102 or having at least 90% sequence identity thereto, and a sequence of the light chain is one set forth in SEQ ID NO: 103 or having at least 90% sequence identity thereto.

In specific embodiments of the PVRIG/TIGIT binding protein of the present disclosure, the VHH of the first antigen-binding domain specifically binding to PVRIG is located at N-terminal of the heavy chain variable region or the full-length heavy chain of the second antigen-binding domain specifically binding to TIGIT;

the VHH of the first antigen-binding domain specifically binding to PVRIG is located at C-terminal of the heavy chain variable region or the full-length heavy chain of the second antigen-binding domain specifically binding to TIGIT;

the VHH of the first antigen-binding domain specifically binding to PVRIG is located at N-terminal of the light chain variable region or the full-length light chain of the second antigen-binding domain specifically binding to TIGIT; and/or the VHH of the first antigen-binding domain specifically binding to PVRIG is located at C-terminal of the light chain variable region or the full-length light chain of the second antigen-binding domain specifically binding to TIGIT.

In specific embodiments of the PVRIG/TIGIT binding protein of the present disclosure, the VHH of the first antigen-binding domain specifically binding to PVRIG is linked, directly or via a linker, to the second antigen-binding domain specifically binding to TIGIT;

preferably, the linker is an amino acid sequence set forth in $(G_4S)_x$ (SEQ ID NO: 168), wherein x is independently selected from the group consisting of integers of 1 to 20; more preferably, the linker is an amino acid sequence set forth in $(G_4S)_2$ (SEQ ID NO: 152) or $(G_4S)_3$ (SEQ ID NO: 156).

In some embodiments, the PVRIG/TIGIT binding protein provided in the present disclosure comprises a first polypeptide chain and a second polypeptide chain, wherein: the first polypeptide chain comprises an amino acid sequence set forth in any one of SEQ ID NOs: 108-112 and 114, and the second polypeptide chain comprises an amino acid sequence set forth in SEQ ID NO: 103; or the first polypeptide chain comprises an amino acid sequence set forth in SEQ ID NO: 104 or 105, and the second polypeptide chain comprises an amino acid sequence set forth in SEQ ID NO: 103; or the first polypeptide chain comprises an amino acid sequence set forth in SEQ ID NO: 102, and the second polypeptide chain comprises an amino acid sequence set forth in SEQ ID NO: 106 or 107.

In a third aspect, the present disclosure provides a polynucleotide encoding the aforementioned PVRIG binding protein, PVRIG/TIGIT binding protein, anti-PVRIG antibody (such as VHH) or anti-PVRIG/TIGIT bispecific antibody. The polynucleotide may be DNA or RNA.

In some embodiments, provided is a polynucleotide composition comprising:

a first nucleic acid encoding the VH or HC of the anti-PVRIG/TIGIT bispecific antibody of the present disclosure; and a second nucleic acid encoding the VL or LC of the anti-PVRIG/TIGIT bispecific antibody of the present disclosure.

In a fourth aspect, the present disclosure provides an expression vector or expression vector composition comprising the polynucleotide or polynucleotide composition described above, wherein the expression vector may be a eukaryotic expression vector, a prokaryotic expression vector or a viral vector.

In some embodiments, provided is an expression vector composition comprising:

a first expression vector comprising the first nucleic acid in the polynucleotide composition described above; and a second expression vector comprising the second nucleic acid in the polynucleotide composition described above.

In a fifth aspect, the present disclosure provides a host cell transformed with or comprising the expression vector or expression vector composition described above, and the host cell may be a eukaryotic cell, or a prokaryotic cell.

In some embodiments, the host cell is the bacteria, yeast or mammalian cell. In some specific embodiments, the host cell is the *E. coli, Pichia pastoris*, Chinese hamster ovary (CHO) cell or human embryonic kidney (HEK) 293 cell.

In a sixth aspect, the present disclosure provides a preparation method, which comprises: expressing the PVRIG binding protein, the anti-PVRIG antibody (such as VHH) or the anti-PVRIG/TIGIT bispecific antibody in the host cell described above, and isolating and recovering the PVRIG binding protein, the anti-PVRIG antibody (such as VHH) or the anti-PVRIG/TIGIT bispecific antibody from the host cell.

In specific embodiments, the present disclosure provides a method for preparing a PVRIG binding protein, a PVRIG/TIGIT binding protein or an anti-PVRIG antibody or an antigen-binding fragment thereof, which comprises:

expressing the polynucleotide of the present disclosure in the host cell of the present disclosure, and isolating the expressed PVRIG binding protein, PVRIG/TIGIT binding protein or anti-PVRIG antibody or antigen-binding fragment thereof from the host cell.

In a seventh aspect, the present disclosure provides a composition (e.g., a pharmaceutical composition) comprising a therapeutically effective amount of the PVRIG binding protein, the anti-PVRIG antibody (e.g., the VHH), the anti-PVRIG/TIGIT bispecific antibody or the PVRIG/TIGIT binding protein described above, and a pharmaceutically acceptable excipient, diluent or carrier.

In some embodiments, the composition (e.g., the pharmaceutical composition) comprises the PVRIG binding protein or the anti-PVRIG antibody (e.g., the VHH) of the present disclosure, and an anti-TIGIT antibody. The TIGIT antibody may be any anti-TIGIT antibody described above, e.g., an anti-TIGIT antibody in Tables 23 and 24 of the present disclosure. Besides, the composition may comprise a pharmaceutically acceptable excipient, diluent or carrier.

In some specific embodiments, the anti-TIGIT antibody comprises an HCDR1, an HCDR2 and an HCDR3 set forth in SEQ ID NOs: 121, 122 and 123, respectively, and the light chain variable region comprises an LCDR1, an LCDR2 and an LCDR3 set forth in SEQ ID NOs: 124, 125 and 126, respectively.

In some specific embodiments, the pharmaceutical composition may comprise, per unit dose, 0.01-99 wt. % of the PVRIG binding protein, the anti-PVRIG antibody (e.g., the VHH) or the anti-PVRIG/TIGIT bispecific antibody, or the amount of the PVRIG binding protein, the anti-PVRIG antibody (e.g., the VHH) or the anti-PVRIG/TIGIT bispecific antibody in the pharmaceutical composition, per unit dose, is 0.1-2000 mg or 1-1000 mg. In an eighth aspect, provided is use of any one of or any combination of the PVRIG binding protein, the anti-PVRIG antibody (e.g., the VHH), the anti-PVRIG/TIGIT bispecific antibody, the PVRIG/TIGIT binding protein, and the polynucleotide encoding the PVRIG binding protein, the anti-PVRIG antibody (e.g., the VHH), the anti-PVRIG/TIGIT bispecific antibody or the PVRIG/TIGIT binding protein of the present disclosure in a method for diagnosing, treating or preventing a disease and in preparing a medicament or a pharmaceutical composition (e.g., for treating or preventing a proliferative disorder (such as a cancer or tumor) or delaying progression of a related disorder).

In some embodiments, provided is a method for treating or ameliorating a disorder in a subject, which comprises administering to the subject the PVRIG binding protein, the anti-PVRIG antibody (e.g., the VHH) or the anti-PVRIG/TIGIT bispecific antibody of the present disclosure, wherein the disorder is cancer.

In some embodiments, provided is a method for activating cytotoxic T cells (CTLs) of a subject, which comprises administering to the subject the PVRIG binding protein, the anti-PVRIG antibody (e.g., the VHH) or the anti-PVRIG/TIGIT bispecific antibody of the present disclosure, wherein a subset of the CTLs of the subject are activated.

In some embodiments, provided is a method for activating NK cells of a subject, which comprises administering to the subject the PVRIG binding protein, the anti-PVRIG antibody (e.g., the VHH) or the anti-PVRIG/TIGIT bispecific antibody of the present disclosure, wherein a subset of the NK cells of the subject are activated.

In some embodiments, provided is a method for activating γδT cells of a subject, which comprises administering to the subject the PVRIG binding protein, the anti-PVRIG antibody (e.g., the VHH) or the anti-PVRIG/TIGIT bispecific antibody of the present disclosure, wherein a subset of the γδT cells of the subject are activated.

In some embodiments, provided is a method for activating Th1 cells of a subject, which comprises administering to the subject the PVRIG binding protein, the anti-PVRIG antibody (e.g., the VHH) or the anti-PVRIG/TIGIT bispecific antibody of the present disclosure, wherein a subset of the Th1 cells of the subject are activated.

In some embodiments, provided is a method for activating, reducing or eliminating the cell number and/or activity of at least one type of regulatory T cells (Tregs) in a subject, which comprises administering to the subject the PVRIG binding protein, the anti-PVRIG antibody (e.g., the VHH) or the anti-PVRIG/TIGIT bispecific antibody of the present disclosure.

In some embodiments, provided is a method for increasing generation of interferon-γ and/or secretion of pro-inflammatory cytokine in a subject, which comprises administering to the subject the PVRIG binding protein, the anti-PVRIG antibody (e.g., the VHH) or the anti-PVRIG/TIGIT bispecific antibody of the present disclosure.

In some embodiments, provided is a method for inhibiting interaction of PVRIG and PVLR2 in a subject, which comprises administering to the subject the PVRIG binding protein, the anti-PVRIG antibody (e.g., the VHH) or the anti-PVRIG/TIGIT bispecific antibody of the present disclosure.

In some embodiments, provided is a method for treating a subject, which comprises administering to the subject or the subject the PVRIG binding protein, the anti-PVRIG antibody (e.g., the VHH) or the anti-PVRIG/TIGIT bispecific antibody of the present disclosure.

In some specific embodiments, the disorder in the subject described above is a proliferative disorder (e.g., a cancer or tumor) or the subject has a proliferative disorder (e.g., a cancer or tumor). The cancer or tumor is selected from the group consisting of the following disorders or combinations thereof: prostate cancer, liver cancer (HCC), colorectal cancer, ovarian cancer, endometrial cancer, breast cancer, triple negative breast cancer, pancreatic cancer, stomach/gastric cancer, cervical cancer, head and neck cancer, thyroid cancer, testicular cancer, urothelial cancer, lung cancer (small cell lung cancer or non-small cell lung cancer), melanoma, non-melanoma skin cancer (squamous and basal cell carcinoma), glioma, renal carcinoma (RCC), lymphoma (NHL or HL), acute myelogenous leukemia (AMIL), T-cell acute lymphoblastic leukemia (T-ALL), diffuse large B-cell lymphoma, testis germ cell tumor, mesothelioma, esophageal cancer, Merkel cells cancer, MSI-high cancer, KRAS-mutant tumor, adult T-cell leukemia/lymphoma and myelodysplastic syndrome (MDS). The disorders described above may be associated with aberrant expression of PVRIG and/or TIGIT. In some specific embodiments, the cancer or tumor is selected from the group consisting of the following cancers or combinations thereof: triple negative breast cancer, stomach/gastric cancer, lung cancer (small cell lung cancer or non-small cell lung cancer), Merkel cell carcinoma, MSI-high cancer, KRAS-mutant tumor, adult T cell leukemia/lymphoma and myelodysplastic syndrome (MDS). In some specific embodiments, the cancer or tumor is selected from the group consisting of the following cancers or combinations thereof: triple negative breast cancer, stomach/gastric cancer, lung cancer (small cell lung cancer or non-small cell lung cancer), Merkel cell carcinoma and MSI-high cancer.

In some embodiments, the subject described above has a condition associated with PVRIG and/or TIGIT. In some embodiments, the condition of the subject includes a cancer that expresses or does not express PVRIG and further includes non-metastatic or non-infiltrative and infiltrative or metastatic cancer, wherein PVRIG expression of immune cells, stromal cells or diseased cells inhibits an anti-tumor response and an anti-infiltration immune response. The methods of the present disclosure are particularly suitable for treating vascularized tumors.

In some embodiments, provided is a method for treating or preventing infection or sepsis in a subject, which comprises administering to the subject or the subject the PVRIG binding protein, the anti-PVRIG antibody (e.g., the VHH) or the anti-PVRIG/TIGIT bispecific antibody of the present disclosure. In some embodiments, the infection is a pathogen infection characterized by different degrees of dysfunction of a virus-specific T cell response, such as HIV, HCV or HBV. In some embodiments, the sepsis includes severe sepsis, septic shock, systemic inflammatory response syndrome (SIRS), bacteremia, septicemia, toxemia and septic syndrome.

In some embodiments, provided is the PVRIG binding protein, the PVRIG/TIGIT binding protein, the anti-PVRIG antibody or the antigen-binding fragment thereof, the polynucleotide or the composition of the present disclosure described above for use in treating or delaying a disease, wherein preferably, the disease is a proliferative disease; more preferably, the proliferative disease is cancer;
more preferably, the cancer is selected from the group consisting of lung cancer, prostate cancer, breast cancer, head and neck cancer, esophageal cancer, gastric cancer, colon cancer, colorectal cancer, bladder cancer, cervical cancer, uterine cancer, ovarian cancer, liver cancer, melanoma, renal cancer, squamous cell carcinoma, cancers of blood system, and any other diseases or disorders characterized by uncontrolled cell growth.

In some embodiments, provided is a method for diagnosing a disease, which comprises:
a) contacting a tissue from a subject with the PVRIG binding protein or the anti-PVRIG antibody of the present disclosure; and
b) determining the presence of over-expression of PVRIG in the tissue as an indication of the presence of a disease or disorder.

The tissue may be a blood sample or a solid tumor biopsy sample. The PVRIG binding protein or the anti-PVRIG antibody may be labeled, and further, a second labeled antibody that binds to the PVRIG binding protein or the anti-PVRIG antibody may be contacted with the aforementioned sample. In some specific embodiments, the PVRIG binding protein or the anti-PVRIG antibody is labeled, including a radioisotope, a dye (e.g., with a biotin-streptavidin complex), a contrast agent, a fluorescent compound or molecule, and an enhancer (e.g., a paramagnetic ion) for magnetic resonance imaging (MRI). In some specific embodiments, the disease or disorder is the cancer or tumor, infection or sepsis described above.

In a ninth aspect, the present disclosure provides use of the PVRIG binding protein in detection.

The present disclosure provides a composition for detecting PVRIG, which comprises a PVRIG binding protein or an anti-PVRIG antibody. The present disclosure also provides a method, a system or a device for detecting PVRIG in vivo or in vitro, which comprises the use of a PVRIG binding protein or an anti-PVRIG antibody.

In some embodiments, the in vitro detection method, system or device may, for example, comprise (1) contacting a sample with a PVRIG binding protein or an anti-PVRIG antibody; (2) detecting a complex formed between the PVRIG binding protein or anti-PVRIG antibody and the sample; and/or (3) contacting a reference sample (e.g., a control sample) with the antibody; and (4) determining the extent of complex formation between the antibody and the sample by comparison with the reference sample. A change (e.g., a statistically significant change) in complex formation in the sample or subject as compared to a control sample or subject indicates the presence of PVRIG in the sample. In other embodiments, the in vivo detection method, system or device may comprise: (1) administering a PVRIG binding protein or an anti-PVRIG antibody to a subject; and (2) detecting the formation of a complex between the PVRIG binding protein or anti-PVRIG antibody and the subject. The detection may include determining the location or time at which the complex is formed. The antibody binding to PVRIG may be directly or indirectly labeled with a detectable substance to facilitate detection of bound or unbound antibody. Suitable detectable substances include various enzymes, prosthetic groups, fluorescent materials, luminescent materials and radioactive materials. Complex formation between the PVRIG binding protein or anti-PVRIG antibody and PVRIG can be detected by measuring or visualizing the antibody that binds to or does not bind to PVRIG. Conventional detection assays may be used, such as enzyme-linked immunosorbent assay (ELISA), radioimmunoassay (RIA) or tissue immunohistochemistry. In some embodiments, the sample is analyzed for the presence of PVRIG by a competitive immunoassay that uses a marker labeled with a detectable substance and an unlabeled PVRIG binding protein or anti-PVRIG antibody. The living sample to be detected or assayed may be histocyte, blood, plasma, serum, pancreatic juice, urine, feces, tissue fluid or culture solution.

In some embodiments, the PVRIG binding protein or the anti-PVRIG antibody of the present disclosure may be labeled with a fluorophore and a chromophore for detection purposes.

In some embodiments, further provided is a kit that comprises a protein binding to PVRIG or an anti-PVRIG antibody, and may further comprise instructions for diagnostic use. The kit may also comprise at least one additional reagent, such as a label or an additional diagnostic agent. For in vivo use, the antibody may be formulated into a pharmaceutical composition.

The PVRIG antibody and the anti-PVRIG/TIGIT diabody provided in the embodiments of the present disclosure have high specificity and high affinity for PVRIG and/or TIGIT; features greatly reduced immunogenicity of the humanized antibody while completely retaining excellent in vivo and in vitro activity; has good metabolic dynamic characteristics of rats and human bodies; has long half-life and high bioavailability; has good long-term stability, no significant abnormal chemical modification, no significant aggregation at high concentration, and higher purity and thermal stability; has good effects in enhancing the activity of T cells and NK cells and inhibiting the development and progression of tumors.

DETAILED DESCRIPTION

1. Terminology

Figure 1:
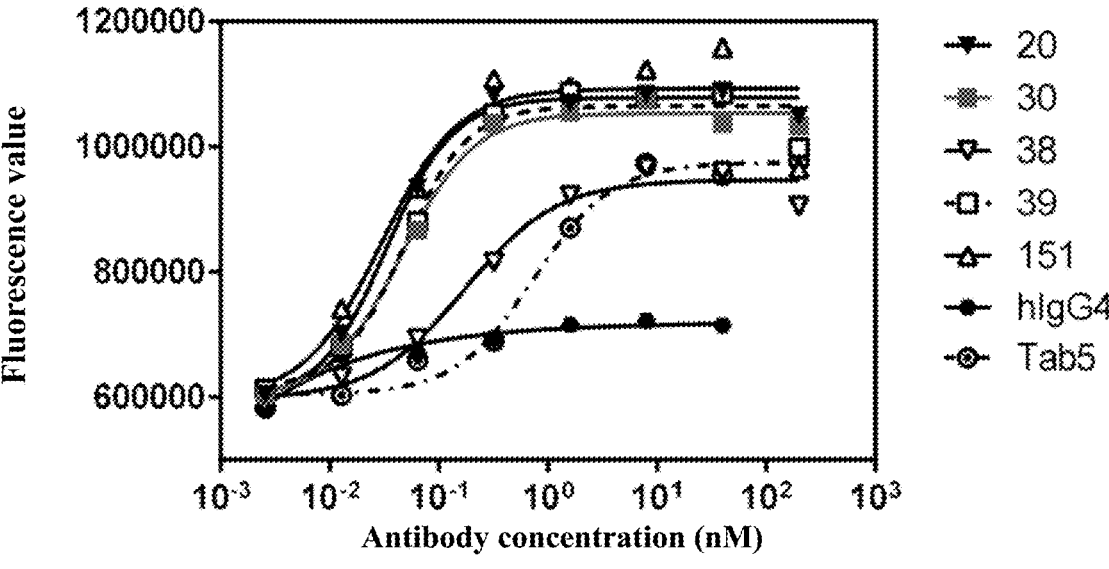
FIG. 1 shows the detection results of the activity of anti-PVRIG antibodies in PVRIG reporter cells.

In order to facilitate the understanding of the present disclosure, some technical and scientific terms are specifically defined below. Unless otherwise specifically defined herein, all other technical and scientific terms used herein have the meanings generally understood by those of ordinary skill in the art to which the present disclosure belongs. The three-letter and single-letter codes for amino acids used in the present disclosure are described as in *J. Biol. Chem*, 243, p 3558 (1968).

"PVRIG", "PVRIG protein" or "PVRIG polypeptide" may optionally include any such protein or a variant, a conjugate or a fragment thereof, including but not limited to known or wild-type PVRIG described herein, as well as any naturally occurring splice variant, amino acid variant or isoform, in particular a soluble extracellular domain (ECD) fragment of PVRIG. ECD is defined herein as in patent application WO2016134333. The complete human PVRIG sequence can be found by GenBank® accession number AAH73861.1.

"PVRIG binding protein" refers to any protein capable of specifically binding to PVRIG or any molecule comprising the protein. The PVRIG binding protein may include an antibody, an antigen-binding fragment thereof or a conjugate thereof defined herein and directed against PVRIG. The PVRIG binding protein also encompasses immunoglobulin superfamily antibodies (IgSF) or CDR-grafted molecules. The "PVRIG binding protein" of the present disclosure may comprise at least one immunoglobulin single variable domain (such as a VHH) that binds to PVRIG. In some embodiments, the "PVRIG binding protein" may comprise 2, 3, 4 or more immunoglobulin single variable domains (such as VHHs) that bind to PVRIG. The PVRIG binding protein of the present disclosure may also comprise, in addition to the immunoglobulin single variable domain of PVRIG, a linker and/or a moiety with effector function, such as a half-life extending moiety (e.g., an immunoglobulin single variable domain that binds to serum albumin), and/or a fusion partner (such as serum albumin) and/or a conjugated polymer (such as PEG) and/or an Fc region. In some embodiments, the "PVRIG binding protein" of the present disclosure also encompasses bispecific/multi-specific antibodies comprising immunoglobulins that bind to different antigens (e.g., a first antibody that binds to a first antigen (e.g., PVRIG) and a second antibody that binds to a second antigen (e.g., TIGIT), optionally a third antibody that binds to a third antigen, and further optionally a fourth antibody that binds to a fourth antigen).

"TIGIT", "TIGIT protein" or "TIGIT polypeptide" may optionally include any such protein or a variant, a conjugate or a fragment thereof, including (but not limited to) known or wild-type TIGIT described herein, as well as any naturally occurring splice variant, amino acid variant or isoform. The complete TIGIT sequence can be found by GenBank® accession number AAI01289.1.

"Binding to PVRIG" refers to the ability to interact with PVRIG or an epitope thereof, wherein the PVRIG or the epitope thereof may be derived from humans. "Binding to TIGIT" refers to the ability to interact with TIGIT or an epitope thereof, wherein the TIGIT or the epitope thereof may be derived from humans. An "antigen-binding site" refers to a discontinuous three-dimensional spatial site on an antigen that is recognized by an antibody or an antigen-binding fragment of the present disclosure.

"Antibody" or "immunoglobulin" broadly encompasses conventional antibodies (antibodies with a tetra-peptide chain structure formed by linking two identical heavy chains and two identical light chains via inter-chain disulfide bonds) and Fab, Fv, sFv, F (ab')$_2$, linear antibodies, single chain antibodies, scFv, sdAb, sdFv, nanobodies, peptibodies, domain antibodies (heavy chain (VH) antibodies and light chain (VL) antibodies) and multi-specific antibodies (bispecific antibodies, diabodies, triabodies, tetrabodies, tandem di-scFvs and tandem tri-scFvs) having antigen binding activity, and thus, the term "antibody" as used herein includes full-length antibodies, individual chains thereof and any portions, domains or fragments thereof having antigen binding activity, and multi-specific antibodies (including but not limited to antigen-binding domains or fragments, such as a VHH domain or a VH/VL domain) comprising the individual chains of the full-length antibody and any portions, domains or fragments of the full-length antibody having antigen binding activity. A conventional antibody or immunoglobulin is usually of a tetrapeptide chain structure formed by linking two identical heavy chains and two identical light chains by inter-chain disulfide bonds. The heavy chain constant regions differ in their amino acid composition and arrangement, and thus in their antigenicity. Accordingly, immunoglobulins can be divided into five classes, otherwise called isotypes of immunoglobulins, namely IgM, IgD, IgG, IgA and IgE, with their corresponding heavy chains being p chain, δ chain, γ chain, α chain and ε chain, respectively. Ig of the same class can be divided into different subclasses according to differences in the amino acid composition of the hinge regions and the number and positions of disulfide bonds of the heavy chains; for example, IgG may be divided into IgG1, IgG2, IgG3 and IgG4. Light chains are classified into κ or λ chains by the differences in the constant regions. Each of the five Ig classes may have a κ (kappa) chain or a λ (lambda) chain. In some embodiments, the antibody of the present disclosure specifically or substantially specifically binds to PVRIG and/or TIGIT.

The "antibodies" of the present disclosure include, but are not limited to: (i) a Fab fragment consisting of VL, VH, CL and CH1 domains; (ii) an Fd fragment consisting of the VH and CH1 domains; (iii) a F(ab')$_2$ fragment, a bivalent fragment comprising two linked Fab fragments; (vii) a single chain Fv molecule (scFv) in which the VH domain and the VL domain are linked by a peptide linker that allows the two domains to bind to form an antigen-binding site; (Bird et al., 1988, *Science* 242: 423-426; Huston et al., 1988, *Proc. Natl. Acad. Sci. U.S.A.* 85:5879-5883) 242, incorporated herein by reference in their entireties); (iv) "bifunctional antibodies" or "trifunctional antibodies", multivalent or multi-specific fragments constructed by gene fusion (Tomlinson et al., 2000, *Methods Enzymol.* 326: 461-479; WO94/13804; Holliger et al., 1993, *Proc. Natl. Acad. Sci. U.S.A.* 90: 6444-6448, all incorporated herein by reference in their entireties); (v) "domain antibodies" or "dAbs" (sometimes referred to as "immunoglobulin single variable domains"), including immunoglobulin single variable domains derived from other species, such as rodents (e.g., as disclosed in WO00/29004), nurse sharks and camelidae V-HH dAbs; (vi) SMIPs (small molecule immunopharmaceuticals), camelid antibodies, nanobodies and IgNARs; (vii) humanized antibodies of the above (i) to (vi).

Unless otherwise stated, antibodies of the present disclosure generally use the Kabat numbering system. EU numbering in Kabat is also generally used for constant domains and/or Fc domains.

The antibodies of the present disclosure may be polyclonal, monoclonal, xenogenic, allogeneic, syngeneic, or modified forms thereof, with monoclonal antibodies being particularly useful in various embodiments. Generally, the antibodies of the disclosure are recombinant antibodies. The "recombinant" used herein generally refers to such products as a cell, a nucleic acid, a protein or a vector, and indicates that the cell, the nucleic acid, the protein or the vector has been modified by the introduction of a heterologous nucleic acid or protein or the alteration of a native nucleic acid or protein, or that the cell is derived from a cell modified in this way. For example, recombinant cells express genes that are not found within the native (non-recombinant) cellular form or express native genes that are abnormally expressed, under expressed or not expressed at all.

"Monoclonal antibody" and "monoclonal antibody composition" refer to a population of antibody molecules that contain only one species of an antigen-binding site capable of immunoreacting with a particular epitope of an antigen, while "polyclonal antibody" and "polyclonal antibody composition" refer to a population of antibody molecules that contain multiple species of antigen-binding sites capable of interacting with a particular antigen. A monoclonal antibody composition typically displays a single binding affinity for a particular antigen with which it immunoreacts.

"Antigen" refers to a molecule used for immunization of an immunocompetent vertebrate to produce an antibody that recognizes the antigen or to screen an expression library (e.g., particularly phage, yeast or ribosome display library). Herein, the antigen is termed more broadly and is generally intended to include target molecules that are specifically recognized by the antibody, and thus includes a portion or a mimic of the molecule used in an immunization process for producing the antibody or in library screening for selecting the antibody.

"Sequence" (e.g., in terms "immunoglobulin sequence", "antibody sequence", "single variable domain sequence", "VHH sequence" or "protein sequence") is generally intended to encompass both related amino acid sequences and nucleic acid or nucleotide sequences encoding the sequences, unless further limited interpretation is required in the present disclosure.

"Polynucleotide" or "nucleic acid" refers to a nucleotide strand of any length, including DNA and RNA. The nucleotides may be deoxyribonucleotides, ribonucleotides, modified nucleotides or bases, and/or analogs thereof, or any substrate that can be incorporated into a strand by a DNA or RNA polymerase. Polynucleotides may comprise modified nucleotides, such as methylated nucleotides and analogs thereof. Modifications to the nucleotide structure, if present, may be imparted before strand assembly or after strand assembly. Polynucleotides may also contain similar forms of ribose or deoxyribose sugars generally known in the art, including, for example, 2'-O-methyl-, 2'-O-allyl, 2'-fluoro- or 2'-azido-ribose, carbocyclic sugar analogs, α- or β-anomeric sugars, epimeric sugars (such as arabinose, xylose or lyxose, pyranose, furanose or sedoheptulose), acyclic analogs and abasic nucleoside analogs such as methyl riboside.

"Homology" or "identity" refers to sequence similarity between two polynucleotide sequences or between two polypeptides. When positions in both compared sequences are occupied by the same base or amino acid monomer subunit, e.g., if each position of two DNA molecules is occupied by adenine, then the molecules are homologous at that position. The homology percentage between two sequences is a function of the number of matched or homologous positions shared by the two sequences divided by the number of positions compared×100%. For example, if 6 out of 10 positions are matched or homologous when two sequences are optimally aligned, the two sequences are 60% homologous. Generally, when two sequences are aligned, comparison is performed to obtain the maximum homology percentage.

"Domain" of a polypeptide or protein refers to a folded protein structure that is capable of maintaining its tertiary structure independently of the rest of the protein. In general, a domain is responsible for a single functional property of a protein, and in many cases may be added, removed or transferred to other proteins without loss of functions of the rest of the protein and/or the domain.

"Immunoglobulin domain" refers to a globular region of an antibody chain (e.g., a chain of a conventional antibody with a tetrapeptide chain structure or of a heavy chain antibody) or a polypeptide essentially consisting of such globular regions. The immunoglobulin domains is characterized in that it retains the immunoglobulin fold characteristic of an antibody molecule, and it consists of a 2-layer sandwich of about 7 antiparallel β-strands arranged in two β-sheets, optionally stabilized by a conserved disulfide bond.

"Immunoglobulin variable domain" refers to an immunoglobulin domain essentially consisting of four "framework regions" referred to in the art and hereinafter as "framework region 1" or "FR1", "framework region 2" or "FR2", "framework region 3" or "FR3", and "framework region 4" or "FR4", wherein the framework regions are interrupted by three "complementarity determining regions" or "CDRs" referred to in the art and hereinafter as "complementarity determining region 1" or "CDR1", "complementarity determining region 2" or "CDR2" and "complementarity determining region 3" or "CDR3". Thus, the general structure or sequence of an immunoglobulin variable domain can be expressed as follows: FR1-CDR1-FR2-CDR2-FR3-CDR3-FR4. Immunoglobulin variable domains possess specificity for an antigen by virtue of having an antigen-binding site.

"Antibody framework (FR)" refers to a portion of a variable domain, which serves as a framework for the antigen-binding loops (CDRs) of the variable domain.

For determination or definition of "CDRs", the deterministic depiction of CDRs and identifying of residues comprising antigen-binding sites of the antibody can be accomplished by resolving the structure of the antibody and/or resolving the structure of the antibody-ligand complex. This can be accomplished by any of a variety of techniques known to those skilled in the art, such as X-ray crystallography. A variety of analysis methods can be used to identify CDRs, including but not limited to Kabat numbering system, Chothia numbering system, AbM numbering system, IMGT numbering system, contact definition, and conformational definition. The Kabat numbering system is a standard for numbering residues in antibodies and is generally used to identify CDRs (see, e.g., Johnson & Wu, 2000, *Nucleic Acids Res.*, 28: 214-8). The Chothia numbering system is similar to the Kabat numbering system, except that it takes into account the location of certain structural loop regions. (see, e.g., Chothia et al., 1986, *J. Mol. Biol.*, 196: 901-17; Chothia et al., 1989, *Nature*, 342: 877-83). The AbM numbering system adopts a computer program integration suite for modeling antibody structures manufactured by Oxford Molecular Group (see, e.g., Martin et al., 1989, *Proc Natl Acad Sci* (USA), 86: 9268-9272; "AbMTM, A Computer Program for Modeling Variable Regions of Antibodies", Oxford, UK; Oxford Molecular, Ltd.). The AbM numbering system adopts a combination of a knowledge database and the de-novo method to model the tertiary structure of antibodies from basic sequences (see those described in Samudrala et al., 1999, "Ab Initio Protein Structure Prediction Using a Combined Hierarchical Approach", *PROTEINS, Structure, Function and Genetics Suppl.,* 3: 194-198). The contact definition is based on the analysis of the available complex crystal structures (see, e.g., MacCallum et al., 1996, *J. Mol. Biol.,* 5: 732-45). In the conformational definition, the positions of the CDRs can be identified as residues that contribute enthalpy to the antigen binding (see, e.g., Makabe et al., 2008, *Journal of Biological Chemistry,* 283: 1156-1166). In addition, other CDR boundary definitions may not strictly follow one of the above methods, but still overlap with at least a portion of the Kabat CDRs, although they may be shortened or lengthened based on predictions or experimental results that a particular residue or a particular group of residues do not significantly affect the antigen binding. As used herein, a CDR may refer to a CDR defined by any method known in the art, including combinations of methods. In the methods used herein, CDRs defined according to any of those methods may be used. For any given embodiment comprising more than one CDR, the CDRs may be defined according to any of Kabat, Chothia, extended, AbM, IMGT, contact, and/or conformational definitions.

"Immunoglobulin single variable domain" is generally used to refer to an immunoglobulin variable domain (which may be a heavy or light chain domain, including a VH, VHH or VL domain) that can form a functional antigen-binding site without interacting with other variable domains (e.g., without VH/VL interactions as are required between the VH and VL domains of conventional four-chain monoclonal antibodies). Examples of "immunoglobulin single variable domains" include nanobodies (including a VHH, humanized VHH and/or camelized VH, e.g. a camelized human VH), IgNAR, domains, (single-domain) antibodies as VH domains or derived from VH domains (such as dAbs™) and (single-domain) antibodies as VL domains or derived from VL domains (such as dAbs™). Immunoglobulin single variable domains based on and/or derived from heavy chain variable domains (such as VH or VHH domains) are generally preferred. A specific example of an immunoglobulin single variable domain is a "VHH domain" (or abbreviated as "VHH") as defined below.

"VHH domain", also known as a heavy chain single-domain antibody, a VHH, a VHH antibody fragment, a VHH antibody or a Nanobody®, is a variable domain of an antigen-binding immunoglobulin known as a "heavy chain antibody" (i.e., "an antibody devoid of light chains") (Hamers-Casterman C, Atarhouch T, Muyldermans S, Robinson G, Hamers C, Songa E B, Bendahman N, Hamers R., "Naturally occurring antibodies devoid of light chains"; *Nature* 363, 446-448 (1993)). The term "VHH domain" is used to distinguish the variable domain from the heavy chain variable domain (which is referred to herein as a "VH domain") and the light chain variable domain (which is referred to herein as a "VL domain") present in conventional antibodies with a tetrapeptide chain structure. VHH domains specifically bind to an epitope without the need for an additional antigen-binding domain (as opposed to the VH or VL domain in conventional antibodies with a tetrapeptide chain structure, in which case the epitope is recognized by the VL domain together with the VH domain). The VHH domain is a small, stable and efficient antigen recognition unit formed by a single immunoglobulin domain. The terms "heavy chain single-domain antibody", "VHH domain", "VHH", "VHH domain", "VHH antibody fragment", "VHH antibody" and "domain" ("Nanobody®" is a registered trademark of Ablynx N. V., Ghent, Belgium) are used interchangeably. "VHH domains" include, but are not limited to, natural antibodies produced by camelids, antibodies produced by camelids and then humanized, or antibodies obtained by screening with phage display techniques.

As is well known in the art for VH domains and for VHH domains, the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Other numbering systems or numbering schemes include Chothia, IMGT and AbM.

The total number of amino acid residues in a VHH domain will usually be in the range of 110 to 120, often between 112 and 115. However, it should be noted that smaller and longer sequences may also be suitable for the purposes described herein.

Compared with conventional VH and VL domains, scFv and conventional antibody fragments (e.g., Fab- or F(ab')$_2$ fragments), VHH domains, either alone or as part of a larger polypeptide, offer a number of superior significant advantages:

only a single domain is required to bind to an antigen with high affinity and high selectivity, so that there is no need to have two separate domains present, nor to assure that these two domains are present in the right spatial conformation and configuration (e.g., the use of specially designed linker is generally required for a scFv);

VHH domains can be expressed from a single gene and do not require post-translational folding or modification;

VHH domains can be easily engineered into multivalent and multi-specific formats;

VHH domains are highly soluble and do not have a tendency to aggregate;

VHH domains are highly stable to heat, pH, proteases and other denaturing agents or conditions and, thus, may be prepared, stored or transported without the use of refrigeration equipment, so that the cost, time and environment can be saved;

VHH domains are easy to prepare and relatively inexpensive, even on a manufacturing scale;

VHH domains are relatively small compared with conventional antibodies with a tetrapeptide chain structure and antigen-binding fragments thereof (about 15 kDa or ¹⁄₁₀ of conventional IgG in size), and therefore show higher tissue permeability and can be administered at higher doses compared with conventional antibodies with a tetrapeptide chain structure and antigen-binding fragments thereof;

VHH domains can show so-called cavity-binding properties (particularly due to their extended CDR3 loop, compared with conventional VH domains) and can therefore also access targets and epitopes not accessible to conventional antibodies with a tetrapeptide chain structure and antigen-binding fragments thereof.

Methods for obtaining VHHs that bind to a particular antigen or epitope have been previously disclosed in the following documents: R. van der Linden et al., *Journal of Immunological Methods,* 240 (2000) 185-195; Li et al., *J Biol Chem.,* 287 (2012)13713-13721; Deffar et al., *African Journal of Biotechnology* Vol. 8 (12), pp. 2645-2652, 17 Jun., 2009 and WO94/04678.

"Fc variant" or "variant Fc" refers to a protein comprising amino acid modifications in the Fc domain. The Fc variants of the present disclosure are defined according to the amino acid modifications that compose them. Thus, for example, S228P or 228P is an Fc variant with the substitution proline at position 228 relative to the parent Fc polypeptide, wherein the numbering is according to the EU index. The identity of the WT amino acid may be unspecified, in which case the aforementioned variant is referred to as 228P. Examples of "humanization" include "humanization" of VHH domains derived from camelidae by replacing one or more amino acid residues in the amino acid sequence of the original VHH sequence with one or more amino acid residues present at the corresponding positions in a VH domain of a human conventional antibody with a tetrapeptide chain structure (also referred to herein as "sequence optimization"; in addition to humanization, "sequence optimization" may also encompass other modifications to the sequence by one or more mutations providing improved properties of the VHH, such as removal of potential post-translational modification sites). The humanized VHH domain may contain one or more fully human framework region sequences, and in some specific embodiments, may contain the human framework region sequence of IGHV3. Another example of "humanization" includes an antibody produced by grafting mouse CDR sequences into a human antibody variable region framework, i.e., a different type of human germline antibody framework sequence. Therefore, the strong antibody variable antibody reaction induced by a large amount of mouse protein components contained in the chimeric antibody can be overcome. Methods for humanization include, e.g., protein surface amino acid humanization (resurfacing) and universal framework grafting method for antibody humanization (CDR grafting to a universal framework), i.e., "grafting" CDRs onto other "frameworks" (including but not limited to human scaffolds or non-immunoglobulin scaffolds). Scaffolds and techniques suitable for such CDR grafting are known in the art. For example, germline DNA sequences of genes of the human heavy and light chain variable regions can be found in the "VBase" human germline sequence database (available at the Internet address www.mrccpe.com.ac.uk/vbase), as well as in Kabat, E. A. et al., 1991 *Sequences of Proteins of Immunological Interest,* 5th edition. The humanized antibody of the present disclosure also includes humanized antibodies which are further subjected to CDR affinity maturation by phage display. In addition, in order to avoid the decrease in activity caused by the decrease in immunogenicity, the FR sequence in human antibody variable region can be subjected to minimum reverse mutation or back mutation to maintain activity.

"Affinity-matured" antibody has one or more changes in one or more CDRs that result in increased affinity for an antigen as compared to respective parent antibody. Affinity-matured antibodies can be prepared, for example, by methods known in the art as described below: Marks et al., 1992, *Biotechnology* 10: 779-783 or Barbas et al., 1994, *Proc. Nat. Acad. Sci, USA* 91: 3809-3813; Shier et al., 1995, *Gene* 169:

147-155; Yelton et al., 1995, *Immunol.* 155: 1994-2004; Jackson et al., 1995, *J. Immunol.* 154(7): 3310-9; Hawkins et al., 1992, *J. Mol. Biol.* 226(3): 889896; KS Johnson and RE Hawkins, "Affinity maturation of antibodies using phage display", Oxford University Press 1996. Typically, the antibody of the present disclosure will bind to an antigen to be bound (i.e., PVRIG) with a dissociation constant (KD) of preferably $10^{-7}$ to $10^{-10}$ mol/L (M), more preferably $10^{-8}$ to $10^{10}$ mol/L, even more preferably $10^{-9}$ to $10^{-10}$ or less, and/or with an association constant (KA) of at least $10^{-7}$ M, preferably at least $10^{-8}$ M, more preferably at least $10^{-9}$ M or more preferably at least $10^{-10}$ M, as measured in a Biacore®, KinExA® or ForteBio® assay. Any KD value greater than $10^{-4}$ M is generally considered to indicate non-specific binding. Specific binding of an antigen-binding protein to an antigen or epitope can be determined in any suitable manner known, including, for example, surface plasmon resonance (SPR) assays, Scatchard assay, and/or competitive binding assay (e.g., radioimmunoassay (RIA), enzyme immunoassay (EIA), and sandwich competitive assay) described herein.

"Epitope" or "antigenic determinant" used interchangeably herein refers to any antigenic determinant on an antigen to which the paratope of an antibody binds. The antigenic determinant generally comprises chemically active surface groups of molecules such as amino acids or sugar side chains, and usually has specific three-dimensional structural characteristics and specific charge characteristics. For example, an epitope typically comprises at least 3, 4, 5, 6, 7, 8, 9, 10, 11, 12, 13, 14 or 15 contiguous or non-contiguous amino acids in a unique spatial conformation, and it may be a "linear" epitope or a "conformational" epitope. In a linear epitope, all points of interaction between a protein and an interacting molecule (e.g., an antibody) exist linearly along the primary amino acid sequence of the protein. In a conformational epitope, the points of interaction exist across amino acid residues on the protein that are separated from one another. Epitopes of a given antigen can be identified using a number of epitope mapping techniques well known in the art (e.g., *Epitope Mapping Protocols in Methods in Molecular Biology*, vol 66, G. E. Morris, Ed. (1996), U.S. Pat. No. 4,708,871). Antibodies can be competitively screened for binding to the same epitope using conventional techniques known to those skilled in the art. For example, competition and cross-competition studies can be performed to obtain antibodies that compete or cross-compete with one another for binding to an antigen (see, e.g., WO03/48731 for high throughput screening methods). Therefore, an antibody and an antigen-binding fragment thereof that competes with the antibody molecule of the present disclosure for binding to the same epitope on PVRIG can be obtained using conventional techniques known to those skilled in the art.

"Specific binding" or "selective binding" refers to binding of an antibody to an epitope on a predetermined antigen. Typically, an antibody binds to a predetermined antigen or epitope thereof with an equilibrium dissociation constant ($K_D$) of about less than $10^{-7}$ M or even less and with an affinity that is at least twice as high as its affinity for binding to a non-specific antigen (e.g., BSA) other than the predetermined antigen (or epitope thereof) or a closely related antigen, when determined by surface plasmon resonance (SPR) technique in an instrument using recombinant human PVRIG, TIGIT or an epitope thereof as the analyte and an antibody as the ligand. "Antigen-recognizing antibody" is used interchangeably herein with "specifically bound antibody".

"Binding affinity" is used herein as a measure of the strength of a non-covalent interaction between two molecules (e.g., an antibody or a portion thereof and an antigen) and is used to describe monovalent interaction (intrinsic activity). The binding affinity between two molecules can be quantified by determining the dissociation constant ($K_D$). $K_D$ can be determined by measuring the kinetics of complex formation and dissociation by using, for example, the surface plasmon resonance (SPR) method (Biacore®). The rate constants corresponding to the association and dissociation of a monovalent complex are referred to as the association rate constant ka (or kon) and the dissociation rate constant kd (or koff), respectively. $K_D$ is related to ka and kd by the equation $K_D=kd/ka$. The value of the dissociation constant can be determined directly by well-known methods (see Caceci et al., 1984, Byte 9: 340-362; Wong&Lohman, 1993, PNAS 90: 5428-5432). Other standard assays for evaluating the binding ability of an antibody to a target antigen are known in the art and include, for example, ELISA, western blot, RIA and flow cytometry, as well as other assays exemplified elsewhere herein. Similarly, the specificity of an interaction can be evaluated by determining and comparing the $K_D$ value for the interaction of interest (e.g., a specific interaction between an antibody and an antigen) with the $K_D$ value for a interaction not of interest (e.g., a control antibody known not to bind to PVRIG). In some embodiments, the anti-PVRIG antibody of the present disclosure is capable of binding to its target with an affinity at least 2-fold, 10-fold, 50-fold, 100-fold, 200-fold, 500-fold, 1,000-fold, or 10,000-fold greater than its affinity for binding to another non-PVRIG molecule, and these amounts here are not meant to be limiting.

"Conservative modifications" are applicable to amino acid and nucleotide sequences. For particular nucleotide sequences, conservative modifications refer to mutual replacement of those nucleic acids encoding identical or substantially identical amino acid sequences, or, in the case of nucleotides not encoding amino acid sequences, to substantially identical nucleotide sequences. For amino acid sequences, "conservative modifications" refer to the replacement of amino acids in a protein with other amino acids having similar characteristics (e.g., charge, side chain size, hydrophobicity/hydrophilicity, backbone conformation, and rigidity) such that changes can be made frequently without altering the biological activity of the protein. Those skilled in the art know that, generally speaking, a single amino acid replacement in a non-essential region of a polypeptide does not substantially change the biological activity (see, e.g., Watson et al. (1987) *Molecular Biology of the Gene*, The Benjamin/Cummings Pub. Co., p 224, (4th edition)).

"Amino acid mutations" include amino acid substitutions, deletions, insertions, modifications, and any combination thereof, to obtain a final construct that possesses desired properties, such as enhanced stability and increased activity. Amino acid sequence deletions and insertions include amino-terminal and/or carboxyl-terminal deletions and amino acid insertions. Preferred amino acid mutations are amino acid substitutions. To alter the binding properties of, for example, an anti-PVRIG antibody, non-conservative amino acid substitutions may be made, i.e., one amino acid is replaced with another amino acid having different structural and/or chemical properties. Preferred amino acid substitutions include the replacement of hydrophobic amino acids with hydrophilic amino acids. Amino acid substitutions include the replacement with non-naturally occurring amino acids or with naturally occurring amino acid derivatives of the 20 standard amino acids (e.g., 4-hydroxyproline, 3-methylhistidine, ornithine, homoserine and 5-hydroxyly-sine). Amino acid mutations can be generated using genetic or chemical methods well known in the art, including site-directed mutagenesis, PCR, gene synthesis, chemical modification, and the like. The amino acid mutations may occur in the CDRs, FRs or Fc regions of an antibody.

For amino acid mutations in the Fc regions, mutations can be introduced to the wild-type Fc sequence of the antibody of the present disclosure for altering Fc-mediated related activity, and the mutations include, but are not limited to: a) a mutation that alters Fc-mediated CDC activity; b) a mutation that alters Fc-mediated ADCC activity; or c) a mutation that alters FcRn-mediated half-life in vivo (see Leonard G Presta, *Current Opinion in Immunology* 2008, 20: 460-470; Esohe E. Idusogie et al., *J Immunol* 2000, 164: 4178-4184; RAPHAEL A. CLYNES et al., *Nature Medicine*, 2000, Volume 6, Number 4: 443-446; Paul R. Hinton et al., *J Immunol*, 2006, 176: 346-356). Specifically, the mutations include a mutation that modifies the hinge region of CH1 such that the number of cysteine residues in the hinge region is altered, e.g., increased or decreased (see U.S. Pat. No. 5,677,425, incorporated herein by reference in its entirety). Mutations that enhances binding to FcγRIIIa (to result in enhanced ADCC) and mutations that attenuate binding to FcγRIIb are introduced, such as 236A, 239D, 239E, 332E, 332D, 239D/332E, 267D, 267E, 328F, 267E/328F, 236A/332E, 239D/332E/330Y, 239D, 332E/330L, 299T and 297N (see U.S. Ser. No. 11/124,620 and U.S. Pat. No. 6,737,056, incorporated herein by reference in their entireties). In the case of performing Fc modification to increase its biological half-life, for example, one or more of the following muta-tions may be introduced: T252L, T254S and T256F (see U.S. Pat. No. 6,277,375); to increase biological half-life, antibodies can be altered within the CH1 or CL region to contain a salvage receptor binding epitope taken from two loops of a CH2 domain of an Fc region of an IgG (see U.S. Pat. Nos. 5,869,046 and 6,121,022); additional mutations for increasing serum half-life include 428L, 434A, 434S and 428L/434S (see U.S. Pat. Nos. 8,883,973, 6,737,056 and 7,371,826, incorporated herein by reference in their entire-ties). The effector function of an antibody is altered by replacing at least one amino acid residue in the Fc region. For example, one or more amino acids selected from the group consisting of amino acid residues 234, 235, 236, 237, 297, 318, 320 and 322 may be replaced such that the affinity of the antibody for the effector ligand is altered but the antigen binding capacity of the parent antibody is retained. The affinity-altered effector ligand may be, for example, the Fc receptor or C1 component of complement (see U.S. Pat. Nos. 5,624,821 and 5,648,260, incorporated herein in their entireties). One or more amino acid residues within amino acid positions 231 and 239 are altered to thereby alter the ability of the antibody to fix complement (see WO 94/29351, incorporated herein by reference in its entirety). The Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 and 439. (see WO00/42072, incorporated by reference in its entirety). Moreover, the binding sites on human IgG1 for FcγRI, FcγRII, FcγRIII and FcRn have been mapped, and variants with improved binding have been described (see Shields, R. L. et al. (2001) *J. Biol. Chem.* 276:6591-6604). Specific mutations at positions 256, 290, 298, 333, 334 and 339 are shown to improve binding to FcγRIII. In addition, the following combination mutants are shown to improve FcγRIII binding: T256A/S298A, S298A/E333A, S298A/K224A and S298A/E333A/K334A. Moreover, mutations such as M252Y/S254T/T256E or M428L/N434S improve binding to FcRn and increase antibody circulation half-life (see Chan C A and Carter P J (2010) *Nature Rev Immunol* 10: 301-316).

Modifications of the antibody of the present disclosure include pegylation (PEGylation) or addition of other water-soluble moieties, for example, to enhance half-life. The "PEGylation" refers to linking of at least one PEG molecule to another molecule (e.g., a therapeutic protein). For example, PEG is a linear or branched polyether linked at one end to a hydroxyl group and has the following general structure: $HO—(CH_2CH_2O)_n—CH_2CH_2—OH$. To couple PEG to a molecule (polypeptides, polysaccharides, poly-nucleotides and small organic molecules), the PEG can be activated by preparing a derivative of the PEG having a functional group at some or both terminals. A common route for PEG conjugation of proteins is to activate the PEG with functional groups suitable for reaction with lysine and N-terminal amino acid groups. In particular, common reac-tive groups involved in conjugation are the α or ε amino groups of lysine. The reaction of a pegylation linking group with a protein leads to the attachment of the PEG moiety predominantly at the following sites: the α amino group at the N-terminal of the protein, the ε amino group on the side chain of lysine residues, and the imidazole group on the side chain of histidine residues. Since most recombinant proteins possess a single a and a number of ε amino and imidazole groups, numerous positional isomers can be generated depending on the chemical properties of linking groups.

The engineered antibody or the antigen-binding fragment of the present disclosure can be prepared and purified using conventional methods. For example, cDNA sequences encoding the heavy and light chains can be cloned and recombined into an expression vector. Recombinant immu-noglobulin expression vectors can be stably transfected into CHO cells. Mammalian expression systems may result in glycosylation of antibodies, particularly at the highly con-served N-terminal of the Fc region. Stable clones are obtained by expression of antibodies specifically binding to the human-derived antigen. Positive clones are expanded in a serum-free medium of a bioreactor to produce antibodies. The culture solution with the secreted antibody can be purified and collected by a conventional technique. The antibody can be filtered and concentrated using conventional methods. Soluble mixtures and polymers can also be removed using conventional methods, such as a molecular sieve and ion exchange. The resulting product needs to be immediately frozen, e.g., at −70° C., or lyophilized.

"Giving", "administering" and "treating", when applied to animals, humans, experimental subjects, cells, tissues, organs or biological fluid, refer to contact of an exogenous drug, a therapeutic agent, a diagnostic agent or a composi-tion with the animals, humans, subjects, cells, tissues, organs or biological fluid, e.g., therapeutic, pharmacokinetic, diag-nostic, research, and experimental methods. The treatment of the cells comprises contacting the reagent with the cells and contacting the reagent with fluid, wherein the fluid is in contact with the cells. "Giving", "administering" and "treat-ing" also refer to treating, e.g., a cell, by a reagent, diagnosis, a binding composition, or by another cell in vitro and ex vivo. When applied to humans, veterinary or research subjects, they refer to therapeutic treatment, preventive or prophylactic measures, and research and diagnostic applications.

"Treating" or "treatment" refers to administering a therapeutic agent, such as a therapeutic agent comprising any antibody of the present disclosure or a pharmaceutical composition thereof, either internally or externally, to a subject who has had, is suspected of having, or is predisposed to having one or more proliferative diseases or symptoms thereof on which the therapeutic agent is known to have a therapeutic effect. Typically, the therapeutic agent is administered in an amount effective to alleviate one or more symptoms of the disease in the subject or population being treated, whether by inducing regression of such symptoms or inhibiting the development of such symptoms into any clinically measurable degree. The amount of therapeutic agent effective to alleviate any particular symptom of the disease (also referred to as the "therapeutically effective amount") may vary depending on factors such as the disease state, age and weight of the subject, and the ability of the drug to produce a desired therapeutic effect in the subject. Whether a symptom of a disease has been alleviated can be evaluated by any clinical testing methods commonly used by doctors or other health care professionals to evaluate the severity or progression of the symptom. Although embodiments of the present disclosure (e.g., treatment methods or articles of manufacture) may be ineffective in alleviating symptoms of a disease of interest in a certain subject, they shall alleviate the symptoms of the disease of interest in a statistically significant number of subjects as determined by any statistical test method known in the art, such as the Student's t-test, Chi-square test, U-test by Mann and Whitney, Kruskal-Wallis test (H-test), Jonckheere-Terpstra test and Wilcoxon test.

"Effective amount" comprises an amount sufficient to ameliorate or prevent a symptom or sign of a medical condition. An effective amount also refers to an amount sufficient to allow or facilitate diagnosis. The effective amount for a subject may vary depending on the factors such as the condition to be treated, the general health of the subject, the method and dose of administration, and the severity of side effects. An effective amount can be the maximum dose or administration regimen to avoid significant side effects or toxic effects. The subject of the present disclosure may be an animal or a human subject.

"Host cell" includes individual cells or cell cultures which may be or have been the recipient of a vector for incorporation of a polynucleotide insert. The host cell includes progeny of a single host cell, and the progeny may not necessarily be completely identical (in morphology or genomic DNA complement) to the original parent cell due to natural, accidental or deliberate mutations. The host cell includes cells transfected and/or transformed in vivo with polynucleotides of the present disclosure. "Cell", "cell line" and "cell culture" are used interchangeably, and all such designations include their progenies. It should also be understood that all progenies may not be precisely identical in DNA content due to deliberate or unintentional mutations. Mutant progeny with the same function or biological activity as screened in the original transformed cells is included.

"Vector" refers to a construct capable of delivering and, in some embodiments, expressing one or more genes or sequences of interest in a host cell. Examples of vectors include, but are not limited to, viral vectors, naked DNA or RNA expression vectors, plasmid, cosmid or phage vectors, DNA or RNA expression vectors bound to cationic condensing agents, DNA or RNA expression vectors encapsulated in liposomes, and certain eukaryotic cells such as producer cells.

"Optional" or "optionally" means that the event or circumstance subsequently described may, but not necessarily, occur, and that the description includes instances where the event or circumstance occurs or does not occur. For example, "optionally comprising 1-3 antibody heavy chain variable regions" means that the antibody heavy chain variable region of a particular sequence may, but not necessarily, be present.

"Pharmaceutical composition" refers to a mixture containing one or more of the antibodies and the antigen-binding fragments described herein or a physiologically/pharmaceutically acceptable salt or pro-drug thereof, and other chemical components such as physiologically/pharmaceutically acceptable carriers and excipients. The purpose of the pharmaceutical composition is to promote the administration to an organism, which facilitates the absorption of the active ingredient, thereby exerting biological activity.

"Pharmaceutically acceptable carrier" or "pharmaceutically acceptable excipient" includes any material that, when combined with an active ingredient, allows the ingredient to retain biological activity and is non-reactive with the immune system of a subject. Examples include, but are not limited to, any standard pharmaceutical carrier, such as a phosphate buffered saline solution, water, an emulsion such as an oil/water emulsion, and various types of wetting agents. In some embodiments, the diluent for aerosol or parenteral administration is phosphate buffered saline (PBS) or normal (0.9%) saline. Compositions containing such carriers are formulated by well-known conventional methods (see, e.g., *Remington's Pharmaceutical Sciences,* 18th edition, A. Gennaro, eds., Mack Publishing Co., Easton, PA, 1990; and R Remington, *The Science and Practice of Pharmacy,* 20th edition, Mack Publishing, 2000).

"PVRIG binding protein" or "PVRIG antibody" of the present disclosure may comprise one or more effector molecules, for example, in a conjugated manner. The "effector molecules" include, for example, antineoplastic agents, drugs, toxins, biologically active proteins such as enzymes, other antibody or antibody fragments, synthetic or naturally occurring polymers, nucleic acids and fragments thereof such as DNA, RNA and fragments thereof, radionuclides, particularly radioiodide, radioisotopes, chelated metals, nanoparticles and reporter groups such as fluorescent compounds or compounds which may be detected by NMR or ESR spectroscopy. When the effector molecule is a polymer, it may generally be a synthetic or naturally occurring polymer, for example, an optionally substituted straight or branched chain polyalkylene, polyalkenylene or polyoxyalkylene polymer or a branched or unbranched polysaccharide, such as a homo-polysaccharide or a hetero-polysaccharide. Specific optional substituents that may be present on the synthetic polymers described above include one or more hydroxyl, methyl or methoxy groups. Specific examples of synthetic polymers include optionally substituted linear or branched poly(ethylene glycol), poly(propylene glycol), poly(vinyl alcohol) or derivatives thereof, in particular optionally substituted poly(ethylene glycol), such as methoxy poly(ethylene glycol) or derivatives thereof. Specific naturally occurring polymers include lactose, amylose, dextran, glycogen or derivatives thereof. In one embodiment, the polymer is albumin or a fragment thereof, such as human serum albumin or a fragment thereof. Conjugation of the polymer to the PVRIG binding protein or PVRIG antibody can be achieved by conventional methods.

The present disclosure is further described below with reference to examples, which, however, are not intended to limit the scope of the present disclosure.

Experimental procedures without specific conditions indicated in the examples or test examples are generally conducted according to conventional conditions, or according to conditions recommended by the manufacturer of the starting materials or commercial products, see Sambrook et al., *Molecular Cloning: A Laboratory Manual*, Cold Spring Harbor Laboratory Press; *Current Protocols in Molecular Biology*, Ausubel et al., Greene Publishing Association, Wiley Interscience, NY Reagents without specific origins indicated are commercially available conventional reagents.

Example 1: Sequence and Preparation of PVRIG Protein

A his-tagged human PVRIG (h-PVRIG-his) recombinant protein, a mouse IgG2a Fc-tagged human PVRIG (h-PVRIG-mIgG2a Fc) recombinant protein and a human IgG1 Fc-tagged mouse PVRIG (m-PVRIG-hIgG1 Fc) were purified commercial protein reagents purchased from Acrobiosystems, the sequences of which are shown in Table 1.

TABLE 1

Amino acid sequences of recombinant proteins

| Name | Start and end of amino acid sequence | Genbank accession No. |
|---|---|---|
| h-PVRIG-his | Thr41-Asp171 | Q6DKI7-1 |
| h-PVRIG-mIgG2a Fc | Thr41-Asp171 | Q6DKI7-1 |
| m-PVRIG-hIgG1 Fc | Ser35-Asp165 | A0A1B0GS01-1 |

The sequence of the his-tagged cynomolgus monkey PVRIG (cyno-PVRIG-his) recombinant protein is as follows:

(SEQ ID NO: 1)
TPEVWVQVQMEATELSSFTVHCGFLGPGSISLVTVSWGGPDGAGGTKLA

VLHPELGTRQWAPARQARWETQSSISLALEDSGASSPFANTTFCCKFAS

FPEGSWESCGSLPPSSDPGLSAPPTPVPILRADHHHHHH

The recombinant protein was expressed in HEK293 cells by transient transfection by conventional methods, and the supernatant was collected and purified by Ni-NTA. Detection was performed, and cyno-PVRIG-his was obtained.

Example 2: Production of Anti-Human PVRIG Single-Domain Antibodies

Anti-human PVRIG monoclonal single-domain antibodies were produced by immunizing camels. The immune antigen is his-tagged human PVRIG recombinant protein (h-PVRIG-his). Freund's adjuvant (Sigma, Lot No.: F5881/F5506) was used for emulsification, where Freund's complete adjuvant (CFA) CFA was used for primary immunization, and Freund's incomplete adjuvant (IFA) was used for remaining boost immunizations. The immunization injection time was on day 0, day 14, day 28 and day 42. Blood was collected on day 56 for a blood test, and camel serum was tested by the ELISA method to determine the antibody titer in the camel serum.

200 mL of camel peripheral blood was taken, PBMC were isolated therefrom, and RNA was extracted from the cells using Trizol and reverse-transcribed into cDNA. The genes of the variable region of the single-domain antibodies were amplified by the PCR method and cloned into a phage vector, thereby establishing a phage library of the anti-human PVRIG single-domain antibodies.

The phage library was diluted and blocked with BSA, and incubated with magnetic bead Dynabeads® (M-280, Invitrogen). The phages were collected after negative screening and incubation. Dynabeads® were coated and blocked by biotinylated his-tagged human PVRIG and incubated with a phage suspension collected after negative screening, and then the phages were eluted with pancreatin. After 3 rounds of screening, 400 clones obtained from the 3rd round of screening were selected and sequenced, where the heavy chain sequences of 5 single-domain antibodies are shown in Table 2, and the CDRs of different numbering schemes are shown in Table 3.

TABLE 2

Sequences of heavy chain variable regions (HCVRs) of anti-PVRIG antibodies

| Antibody No. | | Amino acid sequence of heavy chain variable region | Sequence No. |
|---|---|---|---|
| 20 | HCVR | DVQLVESGGGSVQAGGSLRLSCVASRYTSRTDCMG WFRQAPGKEHEGVAHIDSDGIPRYVDSVKGRFTISQD HAKNTLYLQMNSLKPEDSATYYCVVGFKFDDDYCA PNDWGQGTQVTVSS | SEQ ID NO: 2 |
| 30 | HCVR | HVQLVESGGGSVQAGGSLRLSCEASGYSYSGDCMG WFRRAPGKERDEGVATIDNAGRIKYADSVKGRFTISH GNGKYILYLQMNSLKPEDTDMYYCAAGWTFGGNCS PADWGQGTQVTVSS | SEQ ID NO: 3 |
| 38 | HCVR | QVQLVESGGGSVQAGGSLRLSCAASPSTYGPSDMA WFRQAPGKQREGVATISAAGRLTYYTDSVRGRFTISR DNAKNTMYLQMNSLKPEDTAMYYCAADFAGGSSLF ADYKYWGQGTQVTVSS | SEQ ID NO: 4 |

TABLE 2-continued

| Sequences of heavy chain variable regions (HCVRs) of anti-PVRIG antibodies | | |
|---|---|---|
| Antibody No. | Amino acid sequence of heavy chain variable region | Sequence No. |
| 39 | HCVR QVQLVESGGGSVQAGGSLRLSCAASRYTSRTDCMG WFRQAPGKEREGVAHIDSDGIPRYVESVKGRFTISQD HAKNTLYLQMNSLKPEDSATYYCVVGFKFGDYCAP NDWGQGTQVTVSS | SEQ ID NO: 5 |
| 151 | HCVR HVQLVESGGGSVQAGGSLRLSCVASASGFTYRPYCM AWFRQAPGKEREAVAGIDIFGGTTYADSVKGRFTASR DNAGFSLFLQMNDLKPEDTAMYYCAAGDSPDGRCP PLGQGLNYWGQGTQVTVSS | SEQ ID NO: 6 |

TABLE 3

| Sequences of heavy chain complementarity determining regions (CDRs) of anti-PVRIG antibodies | | | | |
|---|---|---|---|---|
| Antibody No. | CDR Kabat numbering scheme | Chothia numbering scheme | IMGT numbering scheme | AbM numbering scheme |
| 20 | HCDR1 TDCMG (SEQ ID NO: 7) | RYTSRTD (SEQ ID NO: 22) | RYTSRTDC (SEQ ID NO: 37) | RYTSRTDCMG (SEQ ID NO: 52) |
| | HCDR2 HIDSDGIPRYVDSVK G (SEQ ID NO: 8) | DSDGI (SEQ ID NO: 23) | IDSDGIP (SEQ ID NO: 38) | HIDSDGIPR (SEQ ID NO: 53) |
| | HCDR3 GFKFDDDYCAPND (SEQ ID NO: 9) | GFKFDDDYCAPND (SEQ ID NO: 24) | VVGFKFDDDYCAPN D (SEQ ID NO: 39) | GFKFDDDYCAPN D (SEQ ID NO: 54) |
| 30 | HCDR1 GDCMG (SEQ ID NO: 10) | GYSYSGD (SEQ ID NO: 25) | GYSYSGDC (SEQ ID NO: 40) | GYSYSGDCMG (SEQ ID NO: 55) |
| | HCDR2 TIDNAGRIKYADSVK G (SEQ ID NO: 11) | DNAGR (SEQ ID NO: 26) | IDNAGRI (SEQ ID NO: 41) | TIDNAGRIK (SEQ ID NO: 56) |
| | HCDR3 GWTFGGNCSPAD (SEQ ID NO: 12) | GWTFGGNCSPAD (SEQ ID NO: 27) | AAGWTFGGNCSPAD (SEQ ID NO: 42) | GWTFGGNCSPAD (SEQ ID NO: 57) |
| 38 | HCDR1 PSDMA (SEQ ID NO: 13) | PSTYGPS (SEQ ID NO: 28) | PSTYGPSD (SEQ ID NO: 43) | PSTYGPSDMA (SEQ ID NO: 58) |
| | HCDR2 TISAAGRLTYYTDSV RG (SEQ ID NO: 14) | SAAGRL (SEQ ID NO: 29) | ISAAGRLT (SEQ ID NO: 44) | TISAAGRLTY SEQ ID NO: 59) |
| | HCDR3 DFAGGSSLFADYKY (SEQ ID NO: 15) | DFAGGSSLFADYKY (SEQ ID NO: 30) | AADFAGGSSLFADYK Y(SEQ ID NO: 45) | DFAGGSSLFADYKY (SEQ ID NO: 60) |
| 39 | HCDR1 TDCMG (SEQ ID NO: 16) | RYTSRTD (SEQ ID NO: 31) | RYTSRTDC (SEQ ID NO: 46) | RYTSRTDCMG (SEQ ID NO: 61) |
| | HCDR2 HIDSDGIPRYVESVK G (SEQ ID NO: 17) | DSDGI (SEQ ID NO: 32) | IDSDGIP (SEQ ID NO: 47) | HIDSDGIPR (SEQ ID NO: 62) |
| | HCDR3 GFKFGDYCAPND (SEQ ID NO: 18) | GFKFGDYCAPND (SEQ ID NO: 33) | VVGFKFGDYCAPND (SEQ ID NO: 48) | GFKFGDYCAPND (SEQ ID NO: 63) |
| 151 | HCDR1 YRPYCMA (SEQ ID NO: 19) | ASGFTYRPY (SEQ ID NO: 34) | ASGFTYRPYC (SEQ ID NO: 49) | ASGFTYRPYCMA (SEQ ID NO: 64) |
| | HCDR2 GIDIFGGTTYADSVK G (SEQ ID NO: 20) | DIFGG (SEQ ID NO: 35) | IDIFGGT (SEQ ID NO: 50) | GIDIFGGTT (SEQ ID NO: 65) |
| | HCDR3 GDSPDGRCPPLGQGL NY(SEQ ID NO: 21) | GDSPDGRCPPLGQG LNY(SEQ ID NO: 36) | AAGDSPDGRCPPLGQ GLNY(SEQ ID NO: 51) | GDSPDGRCPPLG QGLNY (SEQ ID NO: 66) |

Example 3: Preparation of Full-Length Anti-PVRIG Antibodies

The heavy chain variable regions of the 5 antibodies of Example 2 were each linked to the Fc region of the human IgG4 heavy chain to construct full-length anti-PVRIG antibodies. The Fc region of the heavy chain comprised a hinge region and carried S228P, F234A, L235A and K447A muta-tions (Eu nomenclature system). The anti-PVRIG antibody CPA.7.021 shown in WO2016134333 was screened from a phage library of antibodies, and it was of a IgG1 subtype and was able to well bind to human PVRIG, but it didn't bind to cynomolgus monkey PVRIG. The heavy chain and light chain variable regions of CPA.7.021 were linked to the heavy chain constant region of human IgG4 (with the S228P, F234A, L235A and K447A mutations) and the light chain constant region of human Kappa to construct a positive antibody Tab5.

The full-length sequences of the 5 antibodies and the positive antibody are shown in Table 4.

TABLE 4

| | | Full-length sequences of heavy and light chains of fully human anti-PVRIG antibodies | |
|---|---|---|---|
| Antibody No. | | Full-length amino acid sequences of heavy/light chains | Sequence No. |
| 20 | HC | DVQLVESGGGSVQAGGSLRLSCVASRYTSRTDCMGWFR QAPGKEHEGVAHIDSDGIPRYVDSVKGRFTISQDHAKNT LYLQMNSLKPEDSATYYCVVGFKFDDDYCAPNDWGQG TQVTVSSESKYGPPCPPCPAPEAAGGPSVFLFPPKPKDTL MISRTPEVTCVVVDVSQEDPEVQFNWYVDGVEVHNAK TKPREEQFNSTYRVVSVLTVLHQDWLNGKEYKCKVSN KGLPSSIEKTISKAKGQPREPQVYTLPPSQEEMTKNQVS LTCLVKGFYPSDIAVEWESNGQPENNYKTTPPVLDSDGS FFLYSRLTVDKSRWQEGNVFSCSVMHEALHNHYTQKSL SLSLGA | SEQ ID NO: 67 |
| 30 | HC | HVQLVESGGGSVQAGGSLRLSCEASGYSYSGDCMGWF RRAPGKERDEGVATIDNAGRIKYADSVKGRFTISHGNGK YILYLQMNSLKPEDTDMYYCAAGWTFGGNCSPADWGQ GTQVTVSSESKYGPPCPPCPAPEAAGGPSVFLFPPKPKDT LMISRTPEVTCVVVDVSQEDPEVQFNWYVDGVEVHNA KTKPREEQFNSTYRVVSVLTVLHQDWLNGKEYKCKVS NKGLPSSIEKTISKAKGQPREPQVYTLPPSQEEMTKNQV SLTCLVKGFYPSDIAVEWESNGQPENNYKTTPPVLDSDG SFFLYSRLTVDKSRWQEGNVFSCSVMHEALHNHYTQKS LSLSLGA | SEQ ID NO: 68 |
| 38 | HC | QVQLVESGGGSVQAGGSLRLSCAASPSTYGPSDMAWFR QAPGKQREGVATISAAGRLTYYTDSVRGRFTISRDNAKN TMYLQMNSLKPEDTAMYYCAADFAGGSSLFADYKYW GQGTQVTVSSESKYGPPCPPCPAPEAAGGPSVFLFPPKP KDTLMISRTPEVTCVVVDVSQEDPEVQFNWYVDGVEV HNAKTKPREEQFNSTYRVVSVLTVLHQDWLNGKEYKC KVSNKGLPSSIEKTISKAKGQPREPQVYTLPPSQEEMTK NQVSLTCLVKGFYPSDIAVEWESNGQPENNYKTTPPVLD SDGSFFLYSRLTVDKSRWQEGNVFSCSVMHEALHNHYT QKSLSLSLGA | SEQ ID NO: 69 |
| 39 | HC | QVQLVESGGGSVQAGGSLRLSCAASRYTSRTDCMGWF RQAPGKEREGVAHIDSDGIPRYVESVKGRFTISQDHAKN TLYLQMNSLKPEDSATYYCVVGFKFGDYCAPNDWGQG TQVTVSSESKYGPPCPPCPAPEAAGGPSVFLFPPKPKDTL MISRTPEVTCVVVDVSQEDPEVQFNWYVDGVEVHNAK TKPREEQFNSTYRVVSVLTVLHQDWLNGKEYKCKVSN KGLPSSIEKTISKAKGQPREPQVYTLPPSQEEMTKNQVS LTCLVKGFYPSDIAVEWESNGQPENNYKTTPPVLDSDGS FFLYSRLTVDKSRWQEGNVFSCSVMHEALHNHYTQKSL SLSLGA | SEQ ID NO: 70 |
| 151 | HC | HVQLVESGGGSVQAGGSLRLSCVASASGFTYRPYCMA WFRQAPGKEREAVAGIDIFGGTTYADSVKGRFTASRDN AGFSLFLQMNDLKPEDTAMYYCAAGDSPDGRCPPLGQ GLNYWGQGTQVTVSSESKYGPPCPPCPAPEAAGGPSVF LFPPKPKDTLMISRTPEVTCVVVDVSQEDPEVQFNWYV DGVEVHNAKTKPREEQFNSTYRVVSVLTVLHQDWLNG KEYKCKVSNKGLPSSIEKTISKAKGQPREPQVYTLPPSQ EEMTKNQVSLTCLVKGFYPSDIAVEWESNGQPENNYKT TPPVLDSDGSFFLYSRLTVDKSRWQEGNVFSCSVMHEA LHNHYTQKSLSLSLGA | SEQ ID NO: 71 |
| Tab5 | HC | EVQLVESGGGVVKPGGSLRLSCAASGFTFGTSSMNWVR QAPGKGLEWVAVISFDGTEIHYADSVKGRFTISRDNSKS TVFLQMNSLRPDDTALYYCAKGSGNIYFYSGMDVWGQ GTTVTVSSASTKGPSVFPLAPCSRSTSESTAALGCLVKD YFPEPVTVSWNSGALTSGVHTFPAVLQSSGLYSLSSVVT VPSSSLGTKTYTCNVDHKPSNTKVDKRVESKYGPPCPPC PAPEAAGGPSVFLFPPKPKDTLMISRTPEVTCVVVDVSQ EDPEVQFNWYVDGVEVHNAKTKPREEQFNSTYRVVSV LTVLHQDWLNGKEYKCKVSNKGLPSSIEKTISKAKGQP REPQVYTLPPSQEEMTKNQVSLTCLVKGFYPSDIAVEWE SNGQPENNYKTTPPVLDSDGSFFLYSRLTVDKSRWQEG NVFSCSVMHEALHNHYTQKSLSLSLGA | SEQ ID NO: 72 |

TABLE 4-continued

Full-length sequences of heavy and light chains of fully
human anti-PVRIG antibodies

| Antibody No. | | Full-length amino acid sequences of heavy/light chains | Sequence No. |
|---|---|---|---|
| | LC | DIQMTQSPSTLSASVGDRVTITCRAGQSISGWLAWFQQK PGKAPNLLIYETSTLESGVPSRFSGSGSGTEYTLTISSLQP DDFATYYCQQYYSYPLTFGQGTKVEIKRTVAAPSVFIFPP SDEQLKSGTASVVCLLNNFYPREAKVQWKVDNALQSG NSQESVTEQDSKDSTYSLSSTLTLSKADYEKHKVYACEV THQGLSSPVTKSFNRGEC | SEQ ID NO: 73 |

(Note: the underlined part is the Fc domain of the heavy chain)

The above sequences were synthesized, digested with BamHI and XhoI, and inserted into a pcDNA3.1 expression vector (Life Technologies Cat. No. V790-20) through the BamHI/XhoI enzymatic digestion site. The expression vector and transfection reagent PEI (Polysciences, Inc. Cat. No. 23966) were transfected into HEK293 cells (Life Technologies Cat. No. 11625019) in a 1:2 ratio, and the cells were placed in a C02 incubator and incubated for 4-5 days. The expressed antibodies were isolated by centrifugation and purified by a conventional method. Detection was performed and the antibodies of interest were obtained.

Example 4: Experiment on Binding of Anti-PVRIG Antibodies to PVRIG Recombinant Proteins ELISA assay was used to detect binding properties of anti-PVRIG antibodies. A microplate was coated with his-tagged PVRIG recombinant protein. After the antibody was added, the activity of the binding of the antibody to the antigen was detected by adding a secondary antibody (HRP-conjugated anti-primary antibody Fe antibody) and HRP substrate TMB.

Human, cynomolgus monkey or mouse PVRIG protein (at a concentration of 1 μg/mL) was coated on a 96-well microplate at 100 μL per well, and incubated overnight at 4° C. The plate was washed three times with a washing solution at 250 μL per well. For each wash, the plate was shaken for 10 s to ensure adequate cleaning. A blocking solution (PBS+0.05% Tween® 20+1% BSA) was added at 300 μL per well and the plate was incubated at room temperature for 1 h. The plate was washed three times with a washing solution at 250 μL per well. For each wash, the plate was shaken for 10 s to ensure adequate cleaning. The test anti-PVRIG antibody diluted in diluent was added at 100 μL per well. The mixture was incubated at 37° C. for 1 h. The plate was washed three times with a washing solution at 250 μL per well. HRP-labeled anti-human IgG secondary antibody (Sigma, A8667) was added at 100 μL per well. The mixture was incubated at 37° C. for 1 h. The plate was washed three times with a washing solution at 250 μL per well. TMB was added at 100 μL per well, and the mixture was reacted for 15 min in the dark. 0.16 M/L sulfuric acid was added at 50 μL per well. The OD values at 450 nm were read by using a Thermo Multiskan® Fc microplate reader, and the $EC_{50}$ values of the binding of the anti-PVRIG antibodies to PVRIG were calculated. All antibodies had a relatively strong binding capacity to human or cynomolgus monkey PVRIG recombinant protein, but they did not bind to mouse PVRIG recombinant protein.

TABLE 5

Results of experiment on binding of anti-PVRIG antibodies to PVRIG recombinant proteins of different species

| Antibody No. | Human PVRIG-his ELISA $EC_{50}$ (nM) | Cynomolgus monkey PVRIG-his ELISA $EC_{50}$ (nM) | Mouse PVRIG-Fc ELISA $EC_{50}$ |
|---|---|---|---|
| 20 | 0.40 | 0.14 | No binding |
| 30 | 0.26 | 0.16 | No binding |
| 38 | 0.26 | 0.40 | No binding |
| 39 | 0.27 | 0.16 | No binding |
| 151 | 2.15 | 2.43 | No binding |
| Tab5 | 2.86 | No binding | No binding |
| IgG4 | No binding | No binding | No binding |

Example 5: Experiment on Binding of Anti-PVRIG Antibodies to Cells Expressing PVRIG A flow cytometer (FACS®) was used to detect binding properties of anti-PVRIG antibodies. A cell strain overexpressing human or cynomolgus monkey PVRIG was constructed, and after the addition of the antibody, the activity of the binding of the antibody to the antigen was detected by the addition of a secondary antibody.

The expression plasmid carries human or cynomolgus monkey PVRIG gene sequence was transfected into HEK293 cells, and the over-expressing stable transfection monoclonal cell strain was obtained by antibiotic screening and infinite dilution. Overexpressing cells were seeded into a 96-well plate at $2 \times 10^5$ cells/per well. The cells were centrifuged at 300 g for 5 min, the supernatant was then removed, 100 μL of the test antibody was added, and the mixture was incubated at 4° C. for 1 h. The mixture was centrifuged, the supernatant was removed, the plate was washed 3 times with 200 μL of a washing solution (PBS+2% FBS), and then 100 μL of an anti-human IgG secondary antibody (Invitrogen, A-11013) labeled with Alexa Fluor® 488 diluted at 1:500 was added. The mixture was incubated at 4° C. for 1 h. The mixture was centrifuged, the supernatant was removed, and the plate was washed 3 times with 200 μL of a washing solution (PBS+2% FBS). Cells were resuspended in 100 μL of PBS and detected by a flow cytometer (BD FACSCalibur™ or BD FACSCanto™ II). All antibodies had a relatively strong binding capacity to human or cynomolgus monkey PVRIG expressed on the cell surface, and the binding capability was significantly stronger than that of the positive antibody Tab5, and Tab5 even did not bind to cynomolgus monkey PVRIG at all.

TABLE 6

Results of experiment on binding of anti-PVRIG antibodies to cells expressing PVRIG of different species

| Antibody No. | Human PVRIG FACS $EC_{50}$ (nM) | Monkey PVRIG FACS $EC_{50}$ (nM) |
|---|---|---|
| 20 | N.A. | N.A. |
| 30 | N.A. | 0.02 |
| 38 | 0.24 | 0.34 |
| 39 | 0.004 | 6.97 |
| 151 | 0.01 | 2.23 |
| Tab5 | 2.13 | No binding |
| IgG4 | No binding | No binding |

Note:
(N.A., not available, means that the binding is too strong, no dissociation of antibody is present even at low concentrations, and it is impossible to fit to get accurate $EC_{50}$.)

Example 6: Experiment on Blocking the Binding of PVRIG to PVRL2 by Anti-PVRIG Antibodies In this experiment, by in vitro blocking experiment, the ability of the selected anti-PVRIG antibodies to block the binding of PVRIG to its ligand PVRL2 was detected. Specifically, a mouse IgG2a Fc-tagged human PVRIG recombinant protein (h-PVRIG-mIgG2a Fc) was coated on a 96-well microplate, an anti-PVRIG antibody was added to fully bind to and occupy an epitope, then his-tagged PVRL2 (PV2-H52E2, AcroBiosystem) was added, and then the binding amount of PVRIG and PVRL2 was calculated by detecting the his tag, and the $IC_{50}$ value of the anti-PVRIG antibody for blocking the PVRIG active site was calculated.

The h-PVRIG-mIgG2a Fc protein (at a concentration of 1 µg/mL) was coated on a 96-well microplate at 100 µL per well, and incubated overnight at 4° C. The plate was washed three times with a washing solution at 250 µL per well. For each wash, the plate was shaken for 10 s to ensure adequate cleaning. A blocking solution was added at 300 µL per well and the plate was incubated at room temperature for 1 h. The plate was washed three times with a washing solution at 250 µL per well. For each wash, the plate was shaken for 10 s to ensure adequate cleaning. 50 µL of diluted test anti-PVRIG antibody and 50 µL of his-tagged ligand PVRL2 were added to each well, and the mixture was incubated at 37° C. for 1 h. The plate was washed three times with a washing solution at 250 µL per well. HRP-labeled anti-his-tagged secondary antibody (Genscrpit) diluted at 1:2000 was added at 100 µL per well. The mixture was incubated at 37° C. for 1 h. The plate was washed three times with a washing solution at 250 µL per well. TMB was added at 100 µL per well, and the mixture was reacted for 15 min in the dark. 0.16 M/L sulfuric acid was added at 50 µL per well. The OD value at 450 nm was read by Thermo Multiskan® Fc microplate reader and the $IC_{50}$ value of the blocking of the binding of PVRIG to PVRL2 by the anti-PVRIG antibody was calculated.

The results showed that all the antibodies tested had a strong effect in inhibiting the binding of human PVRIG to human PVRL2.

TABLE 7

Experiment on blocking of human PVRIG/PVRL2 binding by antibodies

| Antibody No. | ELISA $IC_{50}$ (nM) |
|---|---|
| 20 | 1.18 |
| 30 | 1.11 |

TABLE 7-continued

Experiment on blocking of human PVRIG/PVRL2 binding by antibodies

| Antibody No. | ELISA $IC_{50}$ (nM) |
|---|---|
| 38 | 0.93 |
| 39 | 0.76 |
| 151 | 0.37 |
| Tab5 | 1.16 |
| IgG4 | No blocking |

Example 7: Determination of Affinity of Anti-PVRIG Antibodies for PVRIG

A Protein A biosensor (ForteBio®, #18-5010) was immersed in 200 µL of KB buffer (PBS, pH 7.4, 0.02% Tween® 20, 0.1% BSA) for 60 s for the wetting treatment. Then, the anti-PVRIG antibody was diluted to 10 µg/mL with the KB buffer, and the sensor was immersed in 200 µL of the solution until the reading was 1.2 nm. The sensor was immersed in the KB buffer for 100 s to elute excess antibody. The His-tagged human PVRIG was diluted in a 2-fold gradient to 64-4 nM with the KB buffer. The sensor was immersed in the solution for 300 s for binding. The sensor was immersed in the KB buffer for 600 s for dissociation. The data were fitted in a dynamic 1:1 binding mode. The affinity of anti-PVRIG antibodies to human PVRIG is shown in Table 8.

The results showed that all the antibodies tested had high affinity for human PVRIG.

TABLE 8

Affinity of anti-PVRIG antibodies for human PVRIG

| Antibody No. | Kon (1/Ms) | Koff (1/s) | KD (M) |
|---|---|---|---|
| 20 | 3.43E+05 | 8.07E−05 | 2.36E−10 |
| 30 | 2.84E+05 | 2.05E−04 | 7.23E−10 |
| 38 | 1.32E+05 | 2.87E−04 | 2.17E−09 |
| 39 | 2.42E+05 | 1.69E−04 | 6.96E−10 |
| 151 | 2.61E+05 | 5.22E−05 | 2.00E−10 |
| Tab5 | 7.37E+05 | 1.61E−05 | 2.19E−10 |

Example 8: Experiment on Activity of Anti-PVRIG Antibodies in Reporter Cells

Firstly, a plvx-OS8 ($G_{418}$ resistance) plasmid was constructed and transfected into 293F cells, $G_{418}$ screening was performed, the expression of clone cells OS8 and the activation of Jurkat cells by OS8 was detected by using a flow cytometer at the same time, and the clone with moderate activation degree was screened out, thereby obtaining a 293F-OS8 cell strain; a plvx-PVRL2 plasmid was constructed and used to infect 293F-OS8 cells, and the clone with the highest expression level of PVRL2 was screened out by using a flow cytometer, thereby obtaining a 293F-OS8-PVRL2 cell strain.

Secondly, a plvx-NFAT-Luc (Hygromycin resistance) was constructed and packaged into a lentivirus to infect Jurkat E6.1 cells, Hygromycin was added to screen out resistant clones, OKT3 was used to stimulate the clones, and the clone with moderate Luciferase signals was screened out, thereby obtaining a Jurkat-NFAT-Luc cell line; a plvx-PVRIG (Puromycin resistance) vector was constructed and packaged into a lentivirus to infect Jurkat-NFAT-Luc cells, and the clone with the highest PVRIG expression level was screened out by using a flow cytometer, thus obtaining a Jurkat-NFAT-Luc-PVRIG cell strain.

1E4 Jurkat-NFAT-Luc-PVRIG cells were incubated with the test antibody at 37° C. for 20 min. 1E5 293F-OS8-PVRL2 cells were added, and the mixture was incubated at 37° C. for 5 h. The mixture was then centrifuged, the supernatant was removed, the Luciferase buffer (Promega, E6130) was added to lyse the cells, and the fluorescence value was detected. $EC_{50}$ values were calculated to evaluate the in vitro cell activity of the anti-PVRIG antibodies. The results of the experiment are shown in FIG. 1 and Table 9.

The results showed that all the antibodies tested had relatively strong ability to activate Luciferase in Jurkat cells, and the activity was 3.7-18.5 times of that of the positive antibody, which show that the antibodies can bind to PVRIG and block the binding of PVRL2 to PVRIG.

TABLE 9

| Results of experiment on activity of anti-PVRIG antibodies in reporter cells | |
| --- | --- |
| Antibody strain No. | Experiment on activity in PVRIG reporter cells $EC_{50}$ (nM) |
| 20 | 0.04 |
| 30 | 0.06 |
| 38 | 0.20 |
| 39 | 0.06 |
| 151 | 0.04 |
| Tab5 | 0.74 |
| IgG4 | No binding |

Example 9: NK Cell Killing Experiment of Anti-PVRIG Antibodies

PVRIG is expressed on NK cells, while PVRL2 is expressed in many tumor cells, including K562 cells. The anti-PVRIG antibodies can relieve the inhibition of the NK cell activity by tumor cells by blocking the binding of PVRL2 to PVRIG.

The cultured NK92 cell line (NK cells of a patient with human malignant non-Hodgkin's lymphoma) was washed twice with a washing solution (comprising RPMI 1640, 5% FBS and 10 ng/mL IL-2) and resuspended to a density of $2\times10^6$ cells/mL. NK92 cells were added to a 96-well plate at 50 µL ($1\times10^5$ cells in total) per well. 50 µL of 20 nM or 100 nM test antibody was added, and the mixture was incubated at 37° C. for 30 min. The mixture was washed twice with a washing solution, and the cells were resuspended to a density of $2\times10^5$/mL. Human chronic myelogenous leukemia K562 cells were added at 50 µL ($1\times10^4$ cells in total) per well, so that the ratio of the number of NK92 cells to the number of K562 cells was 10:1. The mixture was incubated at 37° C. for 4 h. The killing activity was measured using the CytoTox-Glo™ cytotoxicity system (Promega, $G_{9292}$). First, 50 µL of AAF-Glo™ reagent was added, the mixture was incubated at room temperature for 15 min, and then the fluorescence of K562 cells killed by NK92 cells was measured. 50 µL of a lysis buffer was added, the mixture was incubated at room temperature for 15 min to lyse all cells in the well, and then the fluorescence of all the cells was measured. Three control groups were prepared, including a sample containing only the culture solution (control group 1), a sample containing only NK92 cells (control group 2), and 150 µL of a sample containing only K562 cells (control group 3), and they were subjected to the same procedure.

The killing activity was calculated according to the following formula:

$$\text{killing activity (\%)} = \{[(R-BG)-(T-BG)-(E-BG)]/[(TL-BGL)-(T-BG)]\}\times100$$

where R is the fluorescence value after AAF-Glo™ is added, BG is the fluorescence value of the control group 1 after AAF-Glo™ is added, E is the fluorescence value of the control group 2 after AAF-Glo™ is added, and T is the fluorescence value of the control group 3 after AAF-Glo™ is added; TL is the fluorescence value of the control group 3 after the lysis buffer is added, and BGL is the fluorescence value of the control group 1 after the lysis buffer is added.

Figure 2:
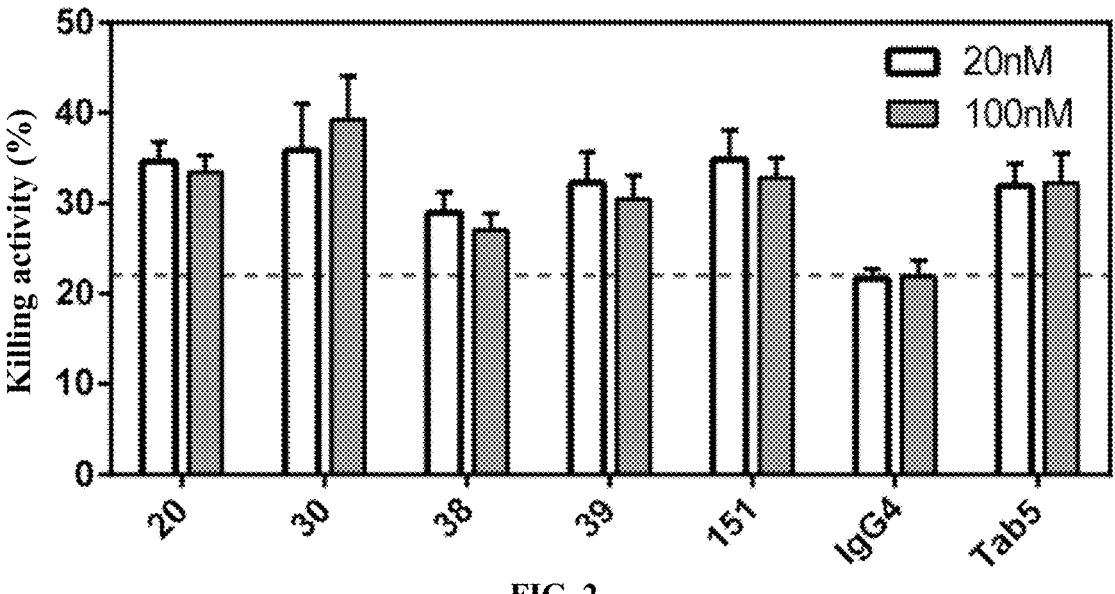
FIG. 2 shows the detection results of the activity of anti-PVRIG antibodies in activating NK cells in NK cell killing experiment.

The results of the experiment are shown in FIG. 2 and Table 10, which show that all the anti-PVRIG antibodies tested can significantly activate NK92 cells and kill K562 cells.

TABLE 10

| NK cell killing experiment of anti-PVRIG antibodies | | |
| --- | --- | --- |
| | Killing activity (%) (mean ± standard deviation) | |
| Antibody No. | 20 nM antibody | 100 nM antibody |
| 20 | 35 ± 2 | 33 ± 2 |
| 30 | 36 ± 5 | 39 ± 5 |
| 38 | 29 ± 2 | 27 ± 2 |
| 39 | 32 ± 3 | 30 ± 3 |
| 151 | 35 ± 3 | 33 ± 2 |
| Tab5 | 32 ± 2 | 32 ± 3 |
| IgG4 | 22 ± 1 | 22 ± 2 |

Example 10: Mixed Lymphocyte Reaction (MLR) Experiment of Anti-PVRIG Antibodies PVRIG is expressed on T cells, while PVRL2 is expressed in dendritic cells (DC cells). By blocking the binding of PVRL2 to PVRIG, the anti-PVRIG antibodies can relieve the inhibition of T cells by dendritic cells and thus activate the T cells.

Figure 3:
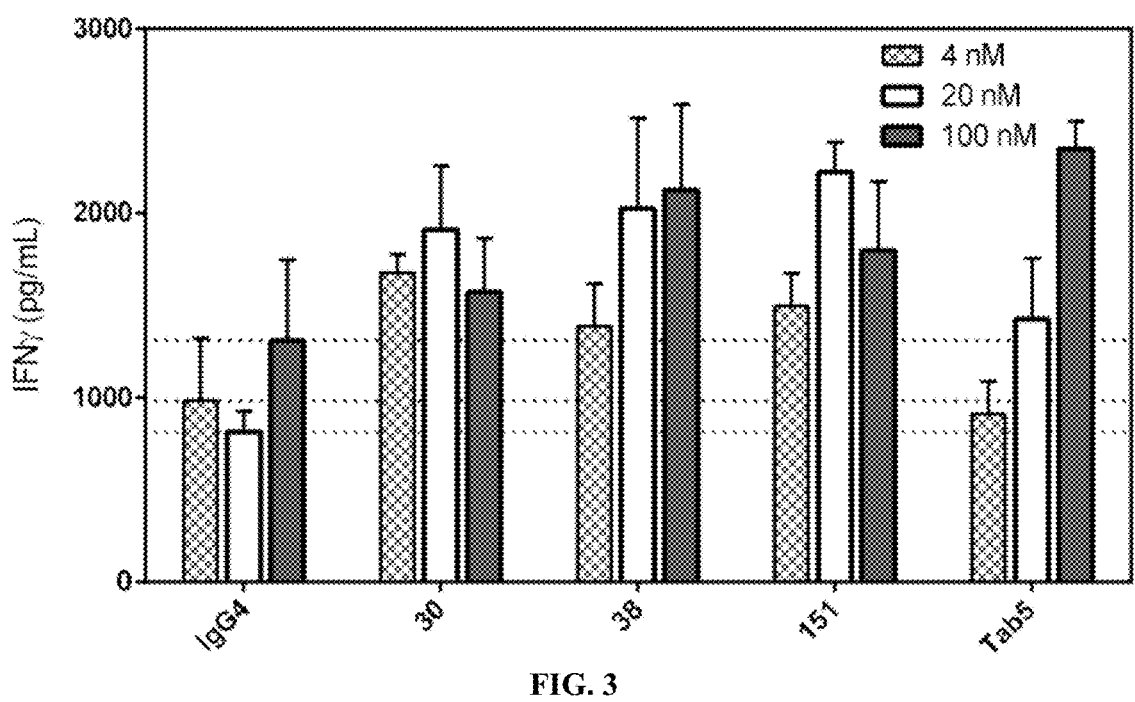
FIG. 3 shows the detection results of the activity of anti-PVRIG antibodies in activating T cells in MLR experiment.

The mixed lymphocyte reaction means that when two unrelated individual lymphocytes with normal functions are co-cultured in vitro, the two lymphocytes can mutually stimulate the T cells of each other to proliferate due to different major histocompatibility antigens. PBMCs were isolated from peripheral blood derived from a first individual and cultured in RPMI 1640 medium containing 10% FBS, cytokines were added at a final concentration of 50 ng/mL GM-CSF (Peprotech, 300-03-100UG) and 50 ng/mL IL-4 (Peprotech, 200-04-100UG), and fresh medium containing the cytokines was added every 2-3 days; after 6 days of culturing, 1 µg/mL LPS (Sigma, L2880-25MG) was added, the mixture was incubated for 24 h, and DC cells obtained by differentiation and maturation were collected. PBMCs were isolated from peripheral blood of a second source, and then CD3$^+$ T cells were isolated from the cells using the EasySep human CD3$^+$ T cell isolation kit (Stemcell, 17952). The density of the CD3$^+$ T cells and DC cells was adjusted, so that $1\times10^5$ CD3$^+$ T cells and $2\times10^{-4}$ DC cells were added per well. The test antibody was added, the mixture was incubated at 37° C. for 120 h, the supernatant was taken, and then the IFNγ content in the supernatant was detected by using an ELISA kit (R&D, DY202). The results of the experiment are shown in FIG. 3 and Table 11, which show that compared with the control antibody IgG4, all the anti-PVRIG antibodies tested can significantly activate T cells to secrete IFNγ. Meanwhile, at low doses (such as 4 nM and 20 nM), the antibodies of the present disclosure outperforms the positive control Tab5.

TABLE 11

IFN γ secretion level in mixed lymphocyte
reaction of anti-PVRIG antibodies

| Antibody No. | IFNYγ (pg/mL) (mean ± standard deviation) | | |
|---|---|---|---|
| | 4 nM antibody | 20 nM antibody | 100 nM antibody |
| 30 | 1675 ± 101 | 1911 ± 347 | 1576 ± 288 |
| 38 | 1388 ± 232 | 2024 ± 491 | 2126 ± 465 |
| 151 | 1498 ± 175 | 2224 ± 162 | 1798 ± 373 |
| Tab5 | 912 ± 173 | 1425 ± 330 | 2349 ± 148 |
| IgG4 | 984 ± 335 | 814 ± 112 | 1309 ± 437 |

Example 11: Humanization of Anti-PVRIG
Antibodies

Based on the VH typical structure of the camel single-domain antibodies 20, 30, 38, 39 and 151 obtained, the heavy chain variable region sequence was compared with an antibody GermLine database to obtain a human germline template with high homology. The framework regions of the camel single-domain antibodies were replaced with the heavy chain framework regions of the human germline template and the CDRs (according to the Kabat numbering system) were retained, and then they were recombined with the Fc region of human IgG (IgG4 Fc with S228P, F234A, L235A and K447A mutations). Based on the three-dimensional structure of the camel single-domain antibody, the embedded residues, the residues directly interacting with the CDRs and the residues that had important influence on the conformation of the variable region were subjected to back mutation, and the chemically unstable amino acid residues in the CDRs were optimized to generate a series of humanized single-domain antibodies. The human germline templates and humanized antibody heavy chain variable region sequences for each single-domain antibody are shown in Tables 12-16.

TABLE 12

Human germline template and humanized
antibody sequences for antibody 20

| Antibody No. | | Amino acid sequence of heavy chain variable region | Sequence No. |
|---|---|---|---|
| Template IGHV3-7*01 | HCVR | EVQLVESGGGLVQPGGSLRLSCAASGFTFSSYWMSW VRQAPGKGLEWVANIKQDGSEKYYVDSVKGRFTISR DNAKNSLYLQMNSLRAEDTAVYYCAR | SEQ ID NO: 74 |
| 20H1 | HCVR | EVQLVESGGGLVQPGGSLRLSCAASGFTFSTDCMGW FRQAPGKGLEGVAHIDSDGIPRYVDSVKGRFTISRDN AKNSLYLQMNSLRAEDTAVYYCVVGFKFDEDYCAP NDWGQGTMVTVSS | SEQ ID NO: 75 |
| 20H2 | HCVR | EVQLVESGGGLVQPGGSLRLSCAASGFTSRTDCMGW FRQAPGKGLEGVAHIDSDGIPRYVDSVKGRFTISRDN AKNSLYLQMNSLRAEDTAVYYCVVGFKFDEDYCAP NDWGQGTMVTVSS | SEQ ID NO: 76 |
| 20H3 | HCVR | EVQLVESGGGLVQPGGSLRLSCAASGYTFSTDCMGW FRQAPGKGLEGVAHIDSDGIPRYVDSVKGRFTISQDH AKNSLYLQMNSLRAEDTAVYYCVVGFKFDEDYCAP NDWGQGTMVTVSS | SEQ ID NO: 77 |
| 20H4 | HCVR | EVQLVESGGGLVQPGGSLRLSCAASGYTSRTDCMG WFRQAPGKGLEGVAHIDSDGIPRYVDSVKGRFTISQD HAKNSLYLQMNSLRAEDTAVYYCVVGFKFDEDYCA PNDWGQGTMVTVSS | SEQ ID NO: 78 |
| 20H5 | HCVR | EVQLVESGGGLVQPGGSLRLSCAASGYTSRTDCMG WFRQAPGKEHEGVAHIDSDGIPRYVDSVKGRFTISQD HAKNSLYLQMNSLRAEDTAVYYCVVGFKFDEDYCA PNDWGQGTMVTVSS | SEQ ID NO: 79 |

According to Table 12, antibodies 20H1-20H5 comprises a CDR1 shown as TDCMG (SEQ ID NO: 7), a CDR2 shown as HIDSDGIPRYVDSVKG (SEQ ID NO: 8) and a CDR3 shown as GFKFDEDYCAPND (SEQ ID NO: 150).

TABLE 13

| Antibody No. | | Amino acid sequence of heavy chain variable region | Sequence No. |
|---|---|---|---|
| Template IGHV3-7*01 | HCVR | EVQLVESGGGLVQPGGSLRLSCAASGFTFSSYWMSW VRQAPGKGLEWVANIKQDGSEKYYVDSVKGRFTISR DNAKNSLYLQMNSLRAEDTAVYYCAR | SEQ ID NO: 74 |
| 30H1 | HCVR | EVQLVESGGGLVQPGGSLRLSCAASGFTFSGDCMGW FRQAPGKGLEGVATIDNAGRIKYADSVKGRFTISRDN AKNSLYLQMNSLRAEDTAVYYCAAGWTFGGQCSPA DWGQGTQVTVSS | SEQ ID NO: 80 |
| 30H2 | HCVR | EVQLVESGGGLVQPGGSLRLSCAASGFTFSGDCMGW FRQAPGKGLDEGVATIDNAGRIKYADSVKGRFTISRD NAKNSLYLQMNSLRAEDTAVYYCAAGWTFGGQCSP ADWGQGTQVTVSS | SEQ ID NO: 81 |
| 30H3 | HCVR | EVQLVESGGGLVQPGGSLRLSCAASGYSYSGDCMG WFRQAPGKGLDEGVATIDNAGRIKYADSVKGRFTISR DNAKNSLYLQMNSLRAEDTAVYYCAAGWTFGGQCS PADWGQGTQVTVSS | SEQ ID NO: 82 |
| 30H4 | HCVR | EVQLVESGGGLVQPGGSLRLSCAASGFTFSGDCMGW FRQAPGKGLDEGVATIDNAGRIKYADSVKGRFTISHG NAKYILYLQMNSLRAEDTAVYYCAAGWTFGGQCSP ADWGQGTQVTVSS | SEQ ID NO: 83 |
| 30H5 | HCVR | EVQLVESGGGLVQPGGSLRLSCAASGYSYSGDCMG WFRQAPGKGLDEGVATIDNAGRIKYADSVKGRFTISH GNAKYILYLQMNSLRAEDTAVYYCAAGWTFGGQCS PADWGQGTQVTVSS | SEQ ID NO: 84 |

According to Table 13, antibodies 30H1-30H5 comprise a CDR1 shown as GDCMG (SEQ ID NO: 10), a CDR2 shown as TIDNAGRIIKYADSVKG (SEQ ID NO: 11) and a CDR3 shown as GWTFGGQCSPAD (SEQ ID NO: 151).

TABLE 14

| Antibody No. | | Amino acid sequence of heavy chain variable region | Sequence No. |
|---|---|---|---|
| Template IGHV3-30*02 | HCVR | QVQLVESGGGVVQPGGSLRLSCAASGFTFSSYGMH WVRQAPGKGLEWVAFIRYDGSNKYYADSVKGRFTIS RDNSKNTLYLQMNSLRAEDTAVYYCAK | SEQ ID NO: 85 |
| 38H2 | HCVR | EVQLVESGGGVVQPGGSLRLSCAASGFTFSPSDMAW FRQAPGKGLEGVATISAAGRLTYYTDSVRGRFTISRD NSKNTLYLQMNSLRAEDTAVYYCAADFAGGSSLFAD YKYWGQGTMVTVSS | SEQ ID NO: 86 |
| 38H4 | HCVR | EVQLVESGGGVVQPGGSLRLSCAASPFTYGPSDMAW FRQAPGKGLEGVATISAAGRLTYYTDSVRGRFTISRD NSKNTLYLQMNSLRAEDTAVYYCAADFAGGSSLFAD YKYWGQGTMVTVSS | SEQ ID NO: 87 |
| 38H7 | HCVR | EVQLVESGGGVVQPGGSLRLSCAASPSTYGPSDMAW FRQAPGKQREGVATISAAGRLTYYTDSVRGRFTISRD NSKNTMYLQMNSLRAEDTAVYYCAADFAGGSSLFA DYKYWGQGTMVTVSS | SEQ ID NO: 88 |
| 38H8 | HCVR | EVQLVESGGGVVQPGGSLRLSCAASPSTYGPSDMAW FRQAPGKGLEGVATISAAGRLTYYTDSVRGRFTISRD NSKNTLYLQMNSLRAEDTAVYYCAADFAGGSSLFAD YKYWGQGTMVTVSS | SEQ ID NO: 89 |

TABLE 14-continued

| | | Human germline template and humanized antibody sequences for antibody 38 | | |
|---|---|---|---|---|
| Antibody No. | | Amino acid sequence of heavy chain variable region | | Sequence No. |
| 38H9 | HCVR | EVQLVESGGGVVQPGGSLRLSCAASPSTYGPSDMAW FRQAPGKGLEGVATISAAGRLTYYTDSVRGRFTISRD NSKNTMYLQMNSLRAEDTAVYYCAADFAGGSSLFA DYKYWGQGTMVTVSS | | SEQ ID NO: 90 |

TABLE 15

| | | Human germline template and humanized antibody sequences for antibody 39 | | |
|---|---|---|---|---|
| Antibody No. | | Amino acid sequence of heavy chain variable region | | Sequence No. |
| Template IGHV3-7*01 | HCVR | EVQLVESGGGLVQPGGSLRLSCAASGFTFSSYWMSW VRQAPGKGLEWVANIKQDGSEKYYVDSVKGRFTISR DNAKNSLYLQMNSLRAEDTAVYYCAR | | SEQ ID NO: 74 |
| 39H1 | HCVR | EVQLVESGGGLVQPGGSLRLSCAASGFTFSTDCMGW FRQAPGKGLEGVAHIDSDGIPRYVESVKGRFTISRDN AKNSLYLQMNSLRAEDTAVYYCVVGFKFGDYCAPN DWGQGTMVTVSS | | SEQ ID NO: 91 |
| 39H2 | HCVR | EVQLVESGGGLVQPGGSLRLSCAASGFTSRTDCMGW FRQAPGKGLEGVAHIDSDGIPRYVESVKGRFTISRDN AKNSLYLQMNSLRAEDTAVYYCVVGFKFGDYCAPN DWGQGTMVTVSS | | SEQ ID NO: 92 |
| 39H3 | HCVR | EVQLVESGGGLVQPGGSLRLSCAASGYTFSTDCMGW FRQAPGKGLEGVAHIDSDGIPRYVESVKGRFTISQDH AKNSLYLQMNSLRAEDTAVYYCVVGFKFGDYCAPN DWGQGTMVTVSS | | SEQ ID NO: 93 |
| 39H4 | HCVR | EVQLVESGGGLVQPGGSLRLSCAASGYTSRTDCMG WFRQAPGKGLEGVAHIDSDGIPRYVESVKGRFTISQD HAKNSLYLQMNSLRAEDTAVYYCVVGFKFGDYCAP NDWGQGTMVTVSS | | SEQ ID NO: 94 |
| 39H5 | HCVR | EVQLVESGGGLVQPGGSLRLSCAASGYTSRTDCMG WFRQAPGKEREGVAHIDSDGIPRYVESVKGRFTISQD HAKNSLYLQMNSLRAEDTAVYYCVVGFKFGDYCAP NDWGQGTMVTVSS | | SEQ ID NO: 95 |

TABLE 16

| | | Human germline template and humanized antibody sequences for antibody 151 | | |
|---|---|---|---|---|
| Antibody No. | | Amino acid sequence of heavy chain variable region | | Sequence No. |
| Template IGHV3-7*01 | HCVR | EVQLVESGGGLVQPGGSLRLSCAASGFTFSSYWMSW VRQAPGKGLEWVANIKQDGSEKYYVDSVKGRFTISR DNAKNSLYLQMNSLRAEDTAVYYCAR | | SEQ ID NO: 74 |
| 151H2 | HCVR | EVQLVESGGGLVQPGGSLRLSCAASGFTYRPYCMAW FRQAPGKGLEAVAGIDIFGGTTYADSVKGRFTISRDN AKNSLYLQMNSLRAEDTAVYYCAAGDSPDGRCPPLG QGLNYWGQGTMVTVSS | | SEQ ID NO: 96 |
| 151H4 | HCVR | EVQLVESGGGLVQPGGSLRLSCVASASGFTYRPYCM AWFRQAPGKGLEAVAGIDIFGGTTYADSVKGRFTISR DNAKNSLYLQMNSLRAEDTAVYYCAAGDSPDGRCP PLGQGLNYWGQGTMVTVSS | | SEQ ID NO: 97 |

TABLE 16-continued

| Human germline template and humanized antibody sequences for antibody 151 | | |
|---|---|---|
| Antibody No. | Amino acid sequence of heavy chain variable region | Sequence No. |
| 151H7 | HCVR HVQLVESGGGLVQPGGSLRLSCVASASGFTYRPYCM AWFRQAPGKEREAVAGIDIFGGTTYADSVKGRFTASR DNAGFSLYLQMNSLRAEDTAVYYCAAGDSPDGRCPP LGQGLNYWGQGTMVTVSS | SEQ ID NO: 98 |
| 151H8 | HCVR EVQLVESGGGLVQPGGSLRLSCVASASGFTYRPYCM AWFRQAPGKGLEAVAGIDIFGGTTYADSVKGRFTISR DNAGFSLYLQMNSLRAEDTAVYYCAAGDSPDGRCPP LGQGLNYWGQGTMVTVSS | SEQ ID NO: 99 |
| 151H9 | HCVR HVQLVESGGGLVQPGGSLRLSCVASASGFTYRPYCM AWFRQAPGKGLEAVAGIDIFGGTTYADSVKGRFTASR DNAGFSLYLQMNSLRAEDTAVYYCAAGDSPDGRCPP LGQGLNYWGQGTMVTVSS | SEQ ID NO: 100 |

The heavy chain variable region of the humanized antibody described above was linked to the Fc region of the human IgG4 heavy chain to construct a full-length anti-PVRIG antibody. The Fc region of the heavy chain comprised a hinge region and carried S228P, F234A, L235A and K447A mutations.

```
>Fc region of human IgG4 heavy chain (S228P/F234A/L235A/K447A)
                                        (SEQ ID NO: 101)
ESKYGPPCPPCPAPEAAGGPSVFLFPPKPKDTLMISRTPEVTCVVVDVSQEDPEVQFNWY

VDGVEVHNAKTKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQPENNYKTTPP

VLDSDGSFFLYSRLTVDKSRWQEGNVFSCSVMHEALHNHYTQKSLSLSLGA

>Fc region of human IgG4 heavy chain (S228P/K447A)
                                        (SEQ ID NO: 153)
ESKYGPPCPPCPAPEFLGGPSVFLFPPKPKDTLMISRTPEVTCVVVDVSQEDPEVQFNWY

VDGVEVHNAKTKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQPENNYKTTPP

VLDSDGSFFLYSRLTVDKSRWQEGNVFSCSVMHEALHNHYTQKSLSLSLGK
```

The antibodies were expressed and purified by conventional methods. Detection was performed and the antibodies of interest were obtained.

Example 12: Experiment on Binding of Humanized Anti-PVRIG Antibodies to Cells Expressing PVRIG Binding of the humanized anti-PVRIG antibodies to human or cynomolgus monkey PVRIG was detected by using a flow cytometer according to the method of Example 5. The results of the experiment are shown in Table 17.

TABLE 17

| Results of FACS experiment on binding of humanized anti-PVRIG single-domain antibodies to PVRIG of different species | | |
|---|---|---|
| Antibody No. | Human PVRIG FACS $EC_{50}$ (nM) | Monkey PVRIG FACS $EC_{50}$ (nM) |
| 20H1 | 0.019 | 0.658 |
| 20H2 | 0.006 | 0.338 |

TABLE 17-continued

| Results of FACS experiment on binding of humanized anti-PVRIG single-domain antibodies to PVRIG of different species | | |
|---|---|---|
| Antibody No. | Human PVRIG FACS $EC_{50}$ (nM) | Monkey PVRIG FACS $EC_{50}$ (nM) |
| 20H3 | 0.006 | 1.500 |
| 20H4 | 0.008 | 0.591 |
| 20H5 | 0.005 | 0.007 |
| 30H1 | 0.024 | 0.374 |
| 30H2 | 0.003 | 0.005 |
| 30H3 | 0.004 | 0.003 |
| 38H2 | 0.088 | 0.137 |
| 38H4 | 0.062 | 0.095 |
| 38H7 | 0.040 | 0.049 |
| 38H8 | 0.065 | N.T. |
| 38H9 | 0.068 | N.T. |
| 39H1 | 0.004 | 0.251 |
| 39H2 | 0.006 | 0.019 |
| 39H3 | 0.005 | 0.348 |
| 39H4 | 0.005 | 0.006 |
| 39H5 | 0.006 | 0.208 |

TABLE 17-continued

Results of FACS experiment on binding of humanized anti-PVRIG
single-domain antibodies to PVRIG of different species

| Antibody No. | Human PVRIG FACS EC$_{50}$ (nM) | Monkey PVRIG FACS EC$_{50}$ (nM) |
|---|---|---|
| 151H4 | 0.240 | 0.035 |
| 151H7 | 0.002 | 0.467 |
| 151H8 | 0.006 | N.T. |
| 151H9 | 0.004 | 3.942 |
| Tab5 | 0.160 | No binding |
| IgG4 | No binding | No binding |

Note:
(N.T., not tested.)

Example 13: Determination of Affinity of Humanized Anti-PVRIG Antibodies for PVRIG The affinity of the humanized anti-PVRIG antibodies for human PVRIG was detected according to the method of Example 7. The results are shown in Table 18. All the antibodies listed in the Table have high affinity for human PVRIG.

TABLE 18

Affinity of humanized anti-PVRIG antibodies for human PVRIG

| Antibody No. | Kon (1/Ms) | Koff (1/s) | KD (M) |
|---|---|---|---|
| 20H5 | 1.93E+05 | 1.35E−05 | 6.98E−11 |
| 30H2 | 1.69E+05 | 3.25E−04 | 1.92E−09 |
| 30H3 | 1.48E+05 | 3.58E−04 | 2.41E−09 |
| 39H1 | 2.64E+05 | 8.65E−04 | 3.28E−09 |
| 39H2 | 1.80E+05 | 1.24E−04 | 6.92E−10 |
| 39H4 | 1.89E+05 | 9.11E−05 | 4.82E−10 |
| 151H7 | 1.57E+05 | 1.88E−04 | 1.20E−09 |

Figure 4A:
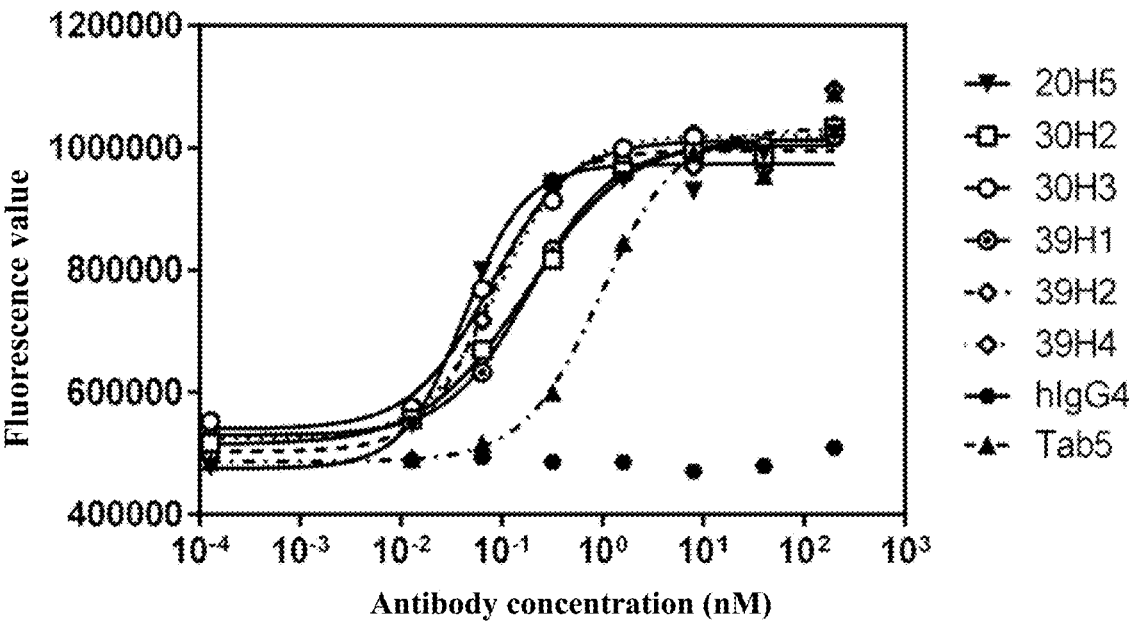
FIGS. 4A-4B show the detection results of the activity of humanized anti-PVRIG antibodies in PVRIG reporter cells.
Figure 4B:
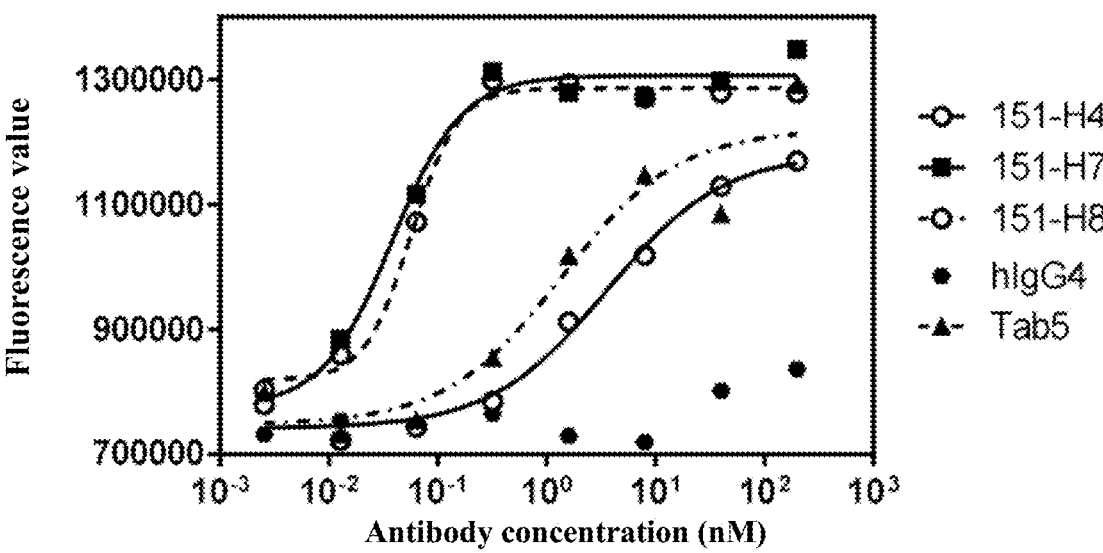

Example 14: Experiment on Activity of Humanized Anti-PVRIG Antibodies in Reporter Cells The activity of the humanized anti-PVRIG antibodies in reporter cells was detected according to the method of Example 8. The results of the experiment are shown in FIGS. 4A-4B and Table 19. All the antibodies listed in the Table have the ability to activate Jurkat cells.

TABLE 19

Experiment on activity of humanized anti-
PVRIG antibodies in reporter cells

| Antibody No. | Experiment on activity in PVRIG reporter cells EC$_{50}$ (nM) |
|---|---|
| 20H5 | 0.042 |
| 30H2 | 0.176 |
| 30H3 | 0.078 |
| 39H1 | 0.191 |
| 39H2 | 0.074 |
| 39H4 | 0.094 |
| 151H4 | 3.549 |
| 151H7 | 0.038 |
| 151H8 | 0.058 |
| Tab5 | 1.380 |
| IgG4 | No activation |

Figure 5A:
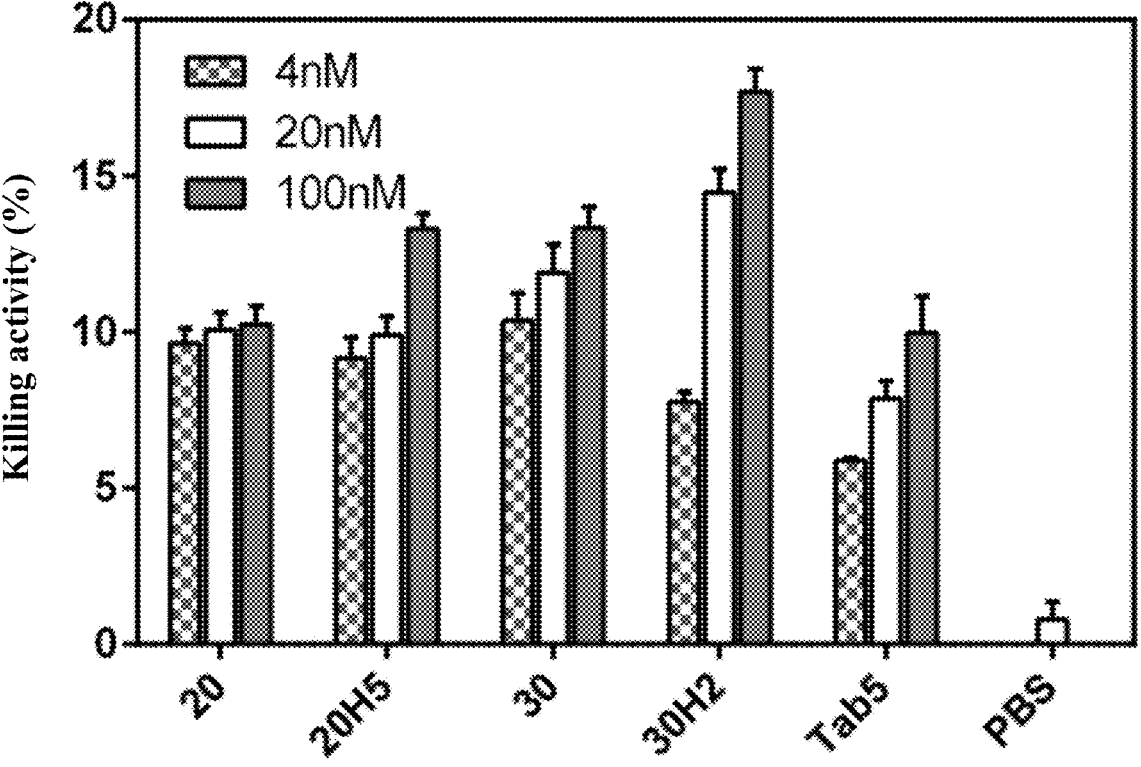
FIGS. 5A-5B show the detection results of activating the NK cell activity by humanized anti-PVRIG antibodies in NK cell killing experiment.
Figure 5B:
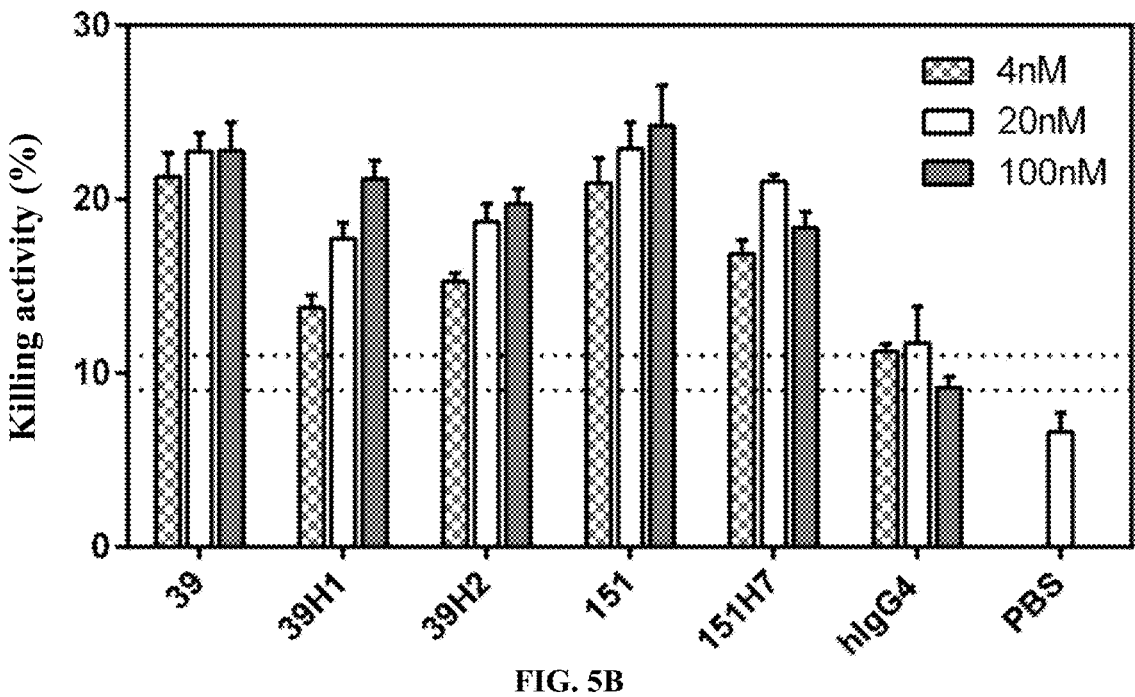
Figure 6A:
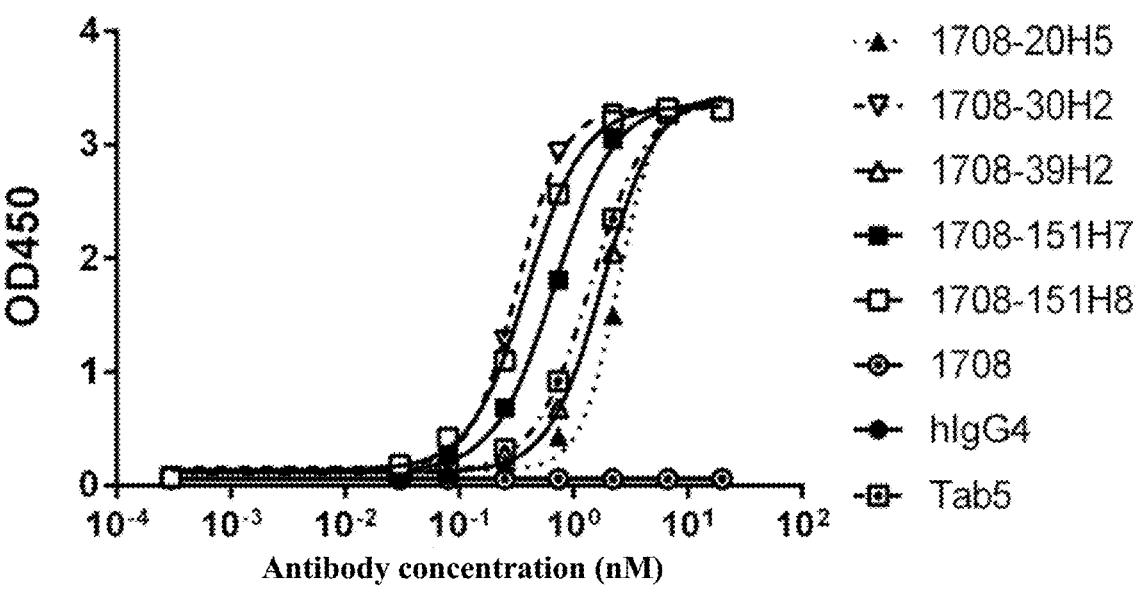
FIGS. 6A-6E show the detection results of the binding activities of the humanized anti-PVRIG/TIGIT bispecific antibodies to human PVRIG recombinant protein, cells overexpressing human PVRIG, cynomolgus monkey PVRIG recombinant protein and cells overexpressing cynomolgus monkey PVRIG, and the activity thereof in blocking the binding of human PVRIG to human PVRL2, respectively.
Figure 6B:
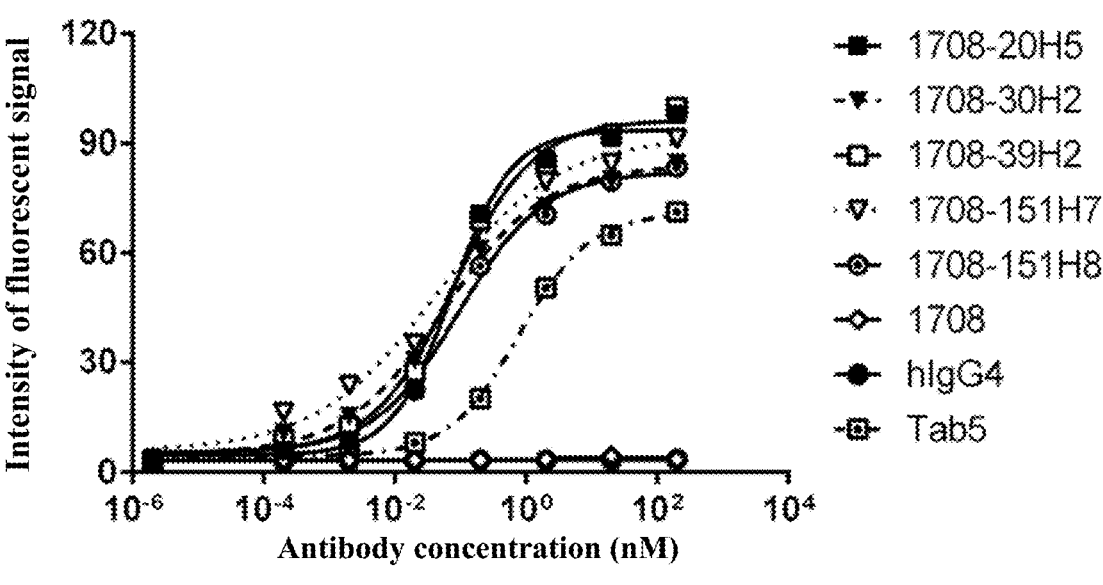
Figure 6C:
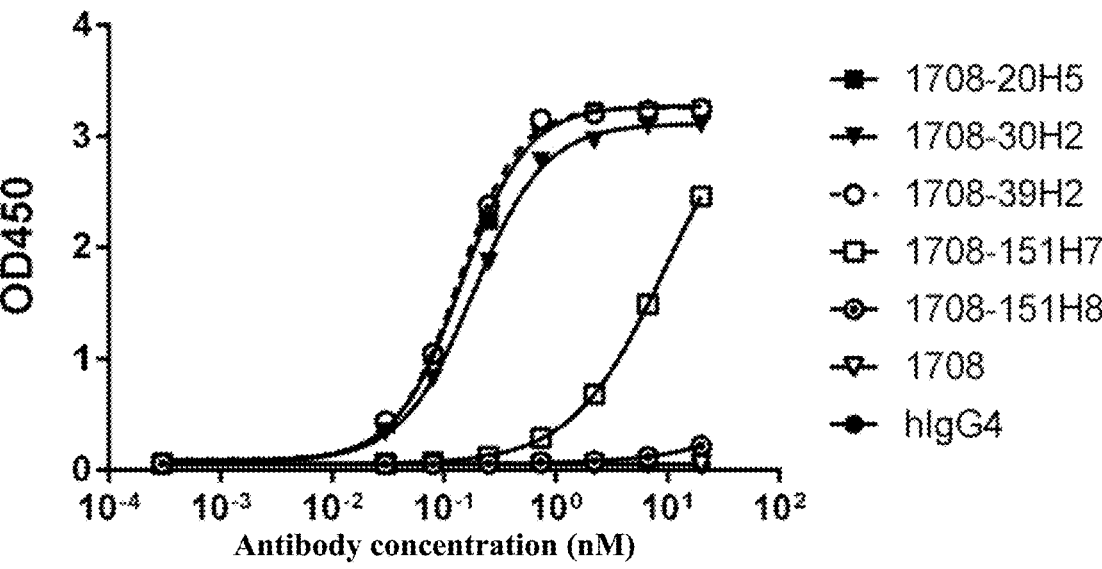
Figure 6D:
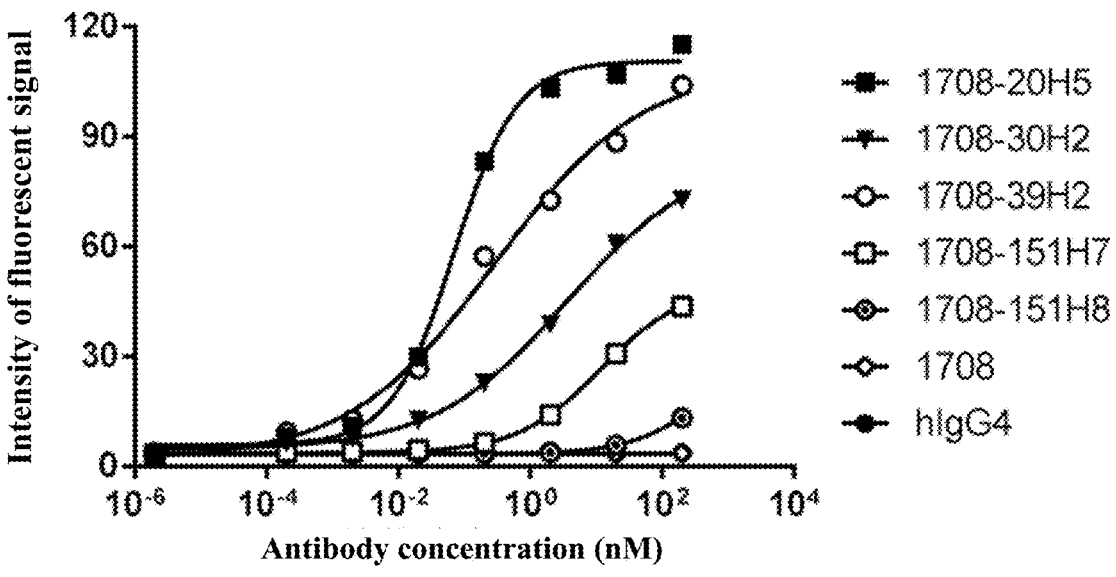
Figure 6E:
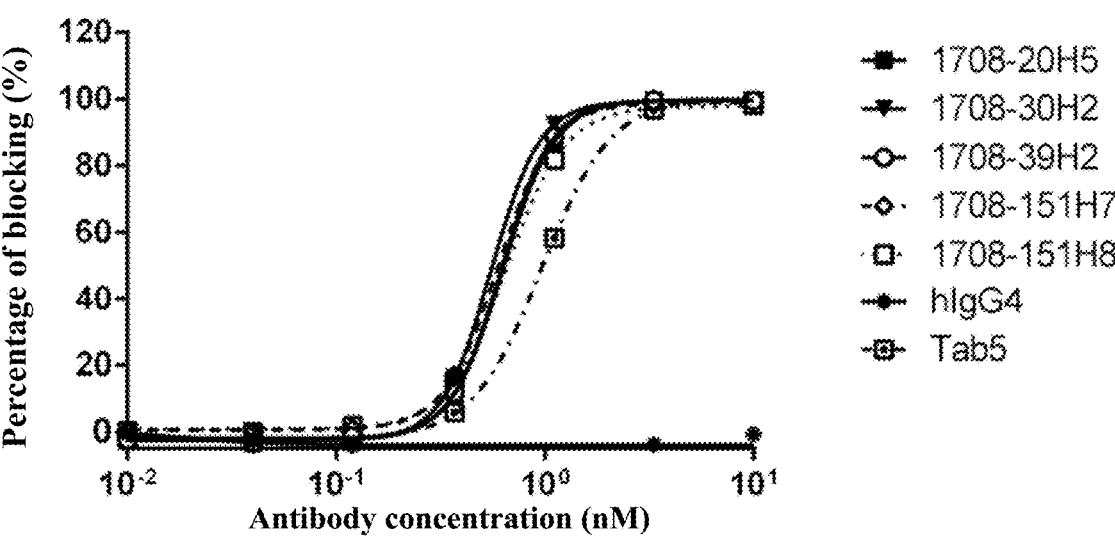
Figure 7A:
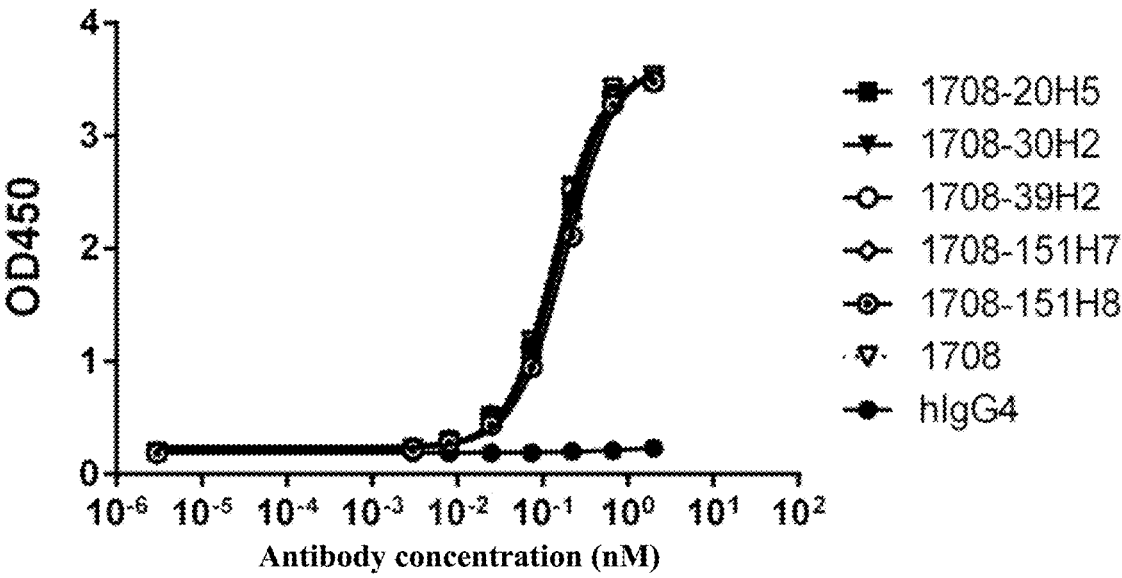
FIGS. 7A-7E show the detection results of the binding activities of the humanized anti-PVRIG/TIGIT bispecific antibodies to human TIGIT recombinant protein, cells overexpressing human TIGIT, cynomolgus monkey TIGIT recombinant protein and cells overexpressing cynomolgus monkey TIGIT, and the activity thereof in blocking the binding of human TIGIT to human PVR, respectively.
Figure 7B:
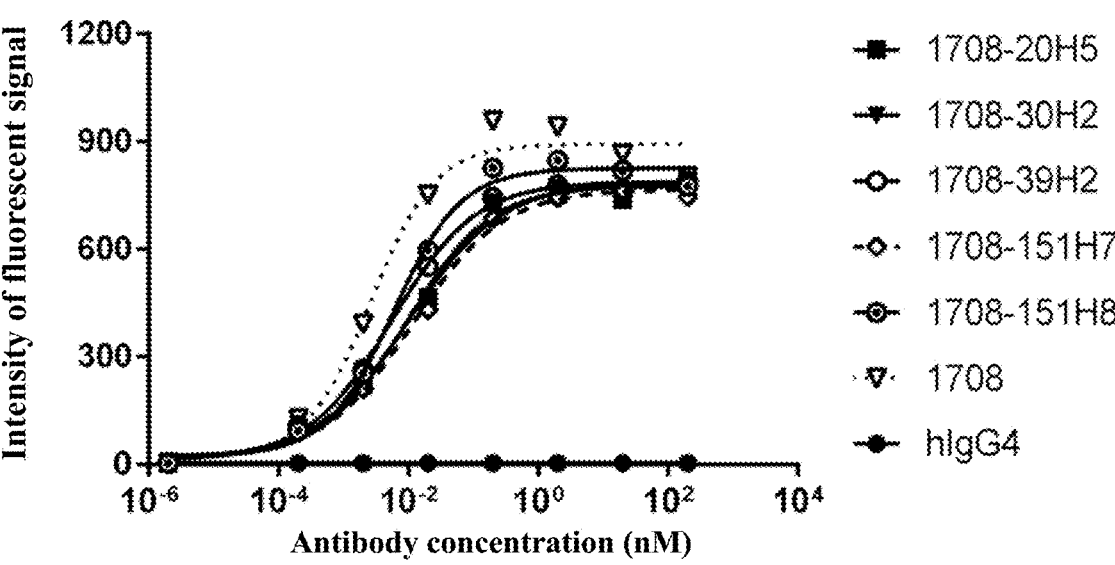
Figure 7C:
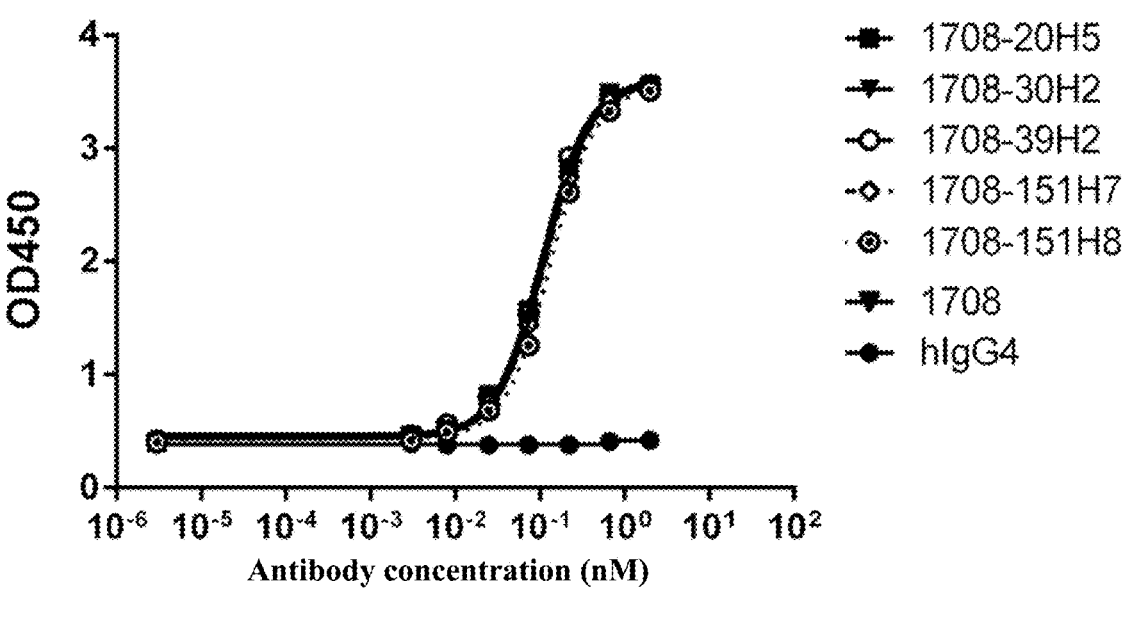
Figure 7D:
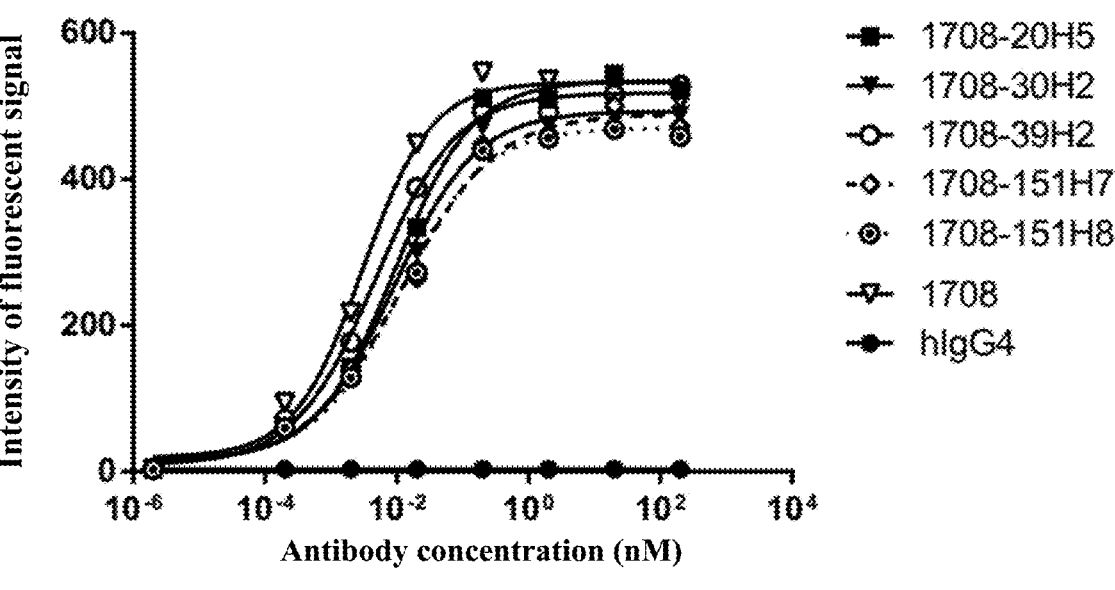
Figure 7E:
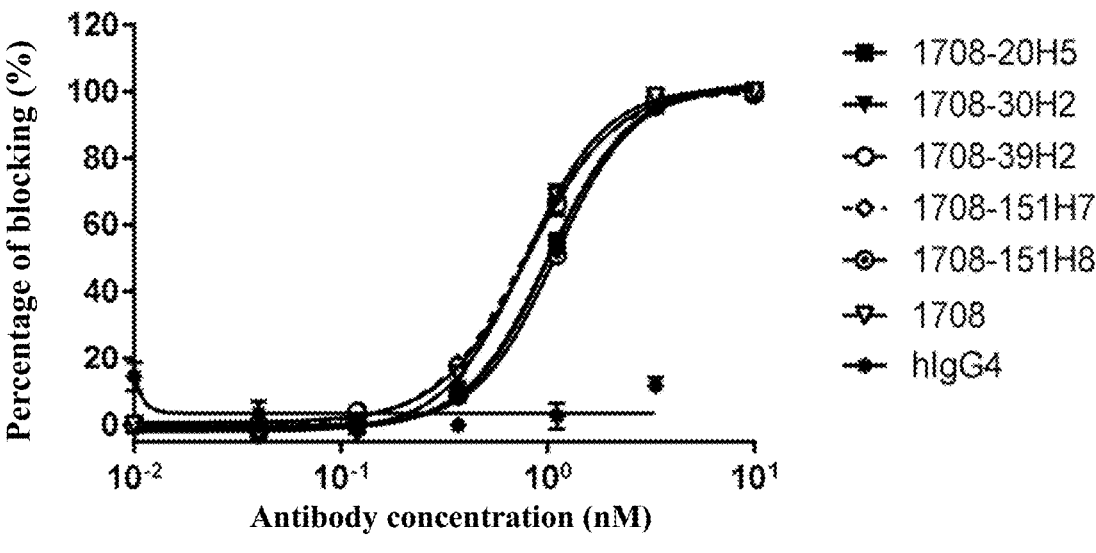

Example 15: Experiment on Activation of NK Cell Killing Ability by Humanized Anti-PVRIG Antibodies The ability of the humanized anti-PVRIG antibodies to activate NK cells was detected according to the method of Example 9. The results of the experiment are shown in FIGS. 5A-5B and Tables 20-21. The results show that the humanized anti-PVRIG antibodies of the present disclosure can significantly activate NK cells and promote the killing of target cells K562 by the NK cells.

TABLE 20

NK cell killing experiment of humanized anti-PVRIG antibodies

| Antibody No. | Killing activity (%) (mean ± standard deviation) | | |
|---|---|---|---|
| | 4 nM antibody | 20 nM antibody | 100 nM antibody |
| 20 | 9.6 ± 0.5 | 10.1 ± 0.5 | 10.2 ± 0.6 |
| 20H5 | 9.2 ± 0.7 | 9.9 ± 0.6 | 13.3 ± 0.5 |
| 30 | 10.4 ± 0.9 | 11.9 ± 0.9 | 13.3 ± 0.7 |
| 30H2 | 7.7 ± 0.3 | 14.5 ± 0.8 | 17.7 ± 0.7 |
| Tab5 | 5.9 ± 0.1 | 7.9 ± 0.6 | 10.0 ± 1.2 |
| PBS | | 0.8 ± 0.6 | |

TABLE 21

NK cell killing experiment of humanized anti-PVRIG antibodies

| Antibody No. | Killing activity (%) (mean ± standard deviation) | | |
|---|---|---|---|
| | 4 nM antibody | 20 nM antibody | 100 nM antibody |
| 39 | 21.3 ± 1.4 | 22.7 ± 1.1 | 22.8 ± 1.6 |
| 39H1 | 13.7 ± 0.7 | 17.7 ± 0.9 | 21.2 ± 1.1 |
| 39H2 | 15.3 ± 0.5 | 18.7 ± 1.0 | 19.7 ± 0.9 |
| 151 | 20.9 ± 1.5 | 22.9 ± 1.5 | 24.2 ± 2.3 |
| 151H7 | 16.9 ± 0.8 | 21.0 ± 0.4 | 18.4 ± 0.9 |
| IgG4 | 11.2 ± 0.4 | 11.7 ± 2.1 | 9.2 ± 0.6 |
| PBS | | 6.6 ± 1.1 | |

Example 16: Preparation of Anti-PVRIG/TIGIT Bispecific Antibodies

To explore the effect of differently configured anti-PVRIG/TIGIT bispecific antibodies on antibody functions, the anti-PVRIG single-domain antibody 151 was linked to the N-terminal or C-terminal of the heavy or light chain of the anti-TIGIT antibody 1708 via the linker GGGGSGGGGS (SEQ ID NO: 152). Four anti-PVRIG/TIGIT bispecific antibodies were formed and named 1708-151-1, 1708-151-2, 1708-151-3 and 1708-151-4, which corresponded to the cases where 151 was linked to the heavy chain N-terminal, heavy chain C-terminal, light chain N-terminal and light chain C-terminal of 1708, respectively. The anti-TIGIT antibody 1708 was of a human IgG4 subtype and had an S228P (Eu nomenclature system) mutation. Sequences of the anti-TIGIT antibody 1708 and the bispecific antibodies formed thereby together with 151 are shown in Table 22 below. Sequence information of anti-TIGIT antibodies is shown in Tables 23-24. The TIGIT antibody in WO2019062832A is incorporated herein by reference in its entirety.

TABLE 22

| Antibody No. | | Full-length amino acid sequences of heavy/light chains | Sequence No. |
|---|---|---|---|
| | | Sequences of first and second polypeptide chains of anti-PVRIG/TIGIT bispecific antibodies | |
| 1708 (anti-TIGIT antibody) | First polypeptide chain | EVQLVQSGAEVKKPGASVKVSCKASGYTFTNYW MHWVRQAPGQGLEWMGRIDPDSTGSKYNEKFK TRVTMTRDTSTSTVYMELSSLRSEDTAVYYCARE GAYGYYFDYWGQGTLVTVSSASTKGPSVFPLAP CSRSTSESTAALGCLVKDYFPEPVTVSWNSGALTS GVHTFPAVLQSSGLYSLSSVVTVPSSSLGTKTYTC NVDHKPSNTKVDKRVESKYGPPCPPCPAPEFLGG PSVFLFPPKPKDTLMISRTPEVTCVVVDVSQEDPE VQFNWYVDGVEVHNAKTKPREEQFNSTYRVVS VLTVLHQDWLNGKEYKCKVSNKGLPSSIEKTISK AKGQPREPQVYTLPPSQEEMTKNQVSLTCLVKGF YPSDIAVEWESNGQPENNYKTTPPVLDSDGSFFL YSRLTVDKSRWQEGNVFSCSVMHEALHNHYTQK SLSLSLGK | SEQ ID NO: 102 |
| | Second polypeptide chain | DIQMTQSPSSLSASVGDRVTITCRASENIYSYLAW YQQKPGKSPKLLIYNARTLAEGVPSRFSGSGSGT DFTLTISSLQPEDFATYYCQYHSGSPLPFGGGTKV EIKRTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVTK SFNRGEC | SEQ ID NO: 103 |
| 1708-151-1 (antibody 151 linked to N-terminal of heavy chain of 1708) | First polypeptide chain | HVQLVESGGGSVQAGGSLRLSCVASASGFTYRPY CMAWFRQAPGKEREAVAGIDIFGGTTYADSVKGR FTASRDNAGFSLFLQMNDLKPEDTAMYYCAAGD SPDGRCPPLGQGLNYWGQGTQVTVSSGGGGSGG GGSEVQLVQSGAEVKKPGASVKVSCKASGYTFT NYWMHWVRQAPGQGLEWMGRIDPDSTGSKYNE KFKTRVTMTRDTSTSTVYMELSSLRSEDTAVYYC AREGAYGYYFDYWGQGTLVTVSSASTKGPSVFPL APCSRSTSESTAALGCLVKDYFPEPVTVSWNSGAL TSGVHTFPAVLQSSGLYSLSSVVTVPSSSLGTKTYT CNVDHKPSNTKVDKRVESKYGPPCPPCPAPEFLG GPSVFLFPPKPKDTLMISRTPEVTCVVVDVSQEDP EVQFNWYVDGVEVHNAKTKPREEQFNSTYRVVS VLTVLHQDWLNGKEYKCKVSNKGLPSSIEKTISK AKGQPREPQVYTLPPSQEEMTKNQVSLTCLVKGF YPSDIAVEWESNGQPENNYKTTPPVLDSDGSFFLY SRLTVDKSRWQEGNVFSCSVMHEALHNHYTQKS LSLSLGK | SEQ ID NO: 104 |
| | Second polypeptide chain | Same as light chain of 1708 | SEQ ID NO: 103 |
| 1708-151-2 (151 linked to C terminal of heavy chain of 1708) | First polypeptide chain | EVQLVQSGAEVKKPGASVKVSCKASGYTFTNYW MHWVRQAPGQGLEWMGRIDPDSTGSKYNEKFK TRVTMTRDTSTSTVYMELSSLRSEDTAVYYCARE GAYGYYFDYWGQGTLVTVSSASTKGPSVFPLAPC SRSTSESTAALGCLVKDYFPEPVTVSWNSGALTSG VHTFPAVLQSSGLYSLSSVVTVPSSSLGTKTYTCN VDHKPSNTKVDKRVESKYGPPCPPCPAPEFLGGPS VFLFPPKPKDTLMISRTPEVTCVVVDVSQEDPEVQ FNWYVDGVEVHNAKTKPREEQFNSTYRVVSVLT VLHQDWLNGKEYKCKVSNKGLPSSIEKTISKAKG QPREPQVYTLPPSQEEMTKNQVSLTCLVKGFYPSD IAVEWESNGQPENNYKTTPPVLDSDGSFFLYSRLT VDKSRWQEGNVFSCSVMHEALHNHYTQKSLSLS LGKGGGGSGGGGSHVQLVESGGGSVQAGGSLRL SCVASASGFTYRPYCMAWFRQAPGKEREAVAGIDI FGGTTYADSVKGRFTASRDNAGFSLFLQMNDLKP EDTAMYYCAAGDSPDGRCPPLGQGLNYWGQGT QVTVSS | SEQ ID NO: 105 |
| | Second polypeptide chain | Same as light chain of 1708 | SEQ ID NO: 103 |
| 1708-151-3 (151 linked to N-terminal of light chain of 1708) | First polypeptide chain | Same as heavy chain of 1708 | SEQ ID NO: 102 |
| | Second polypeptide chain | HVQLVESGGGSVQAGGSLRLSCVASASGFTYRPY CMAWFRQAPGKEREAVAGIDIFGGTTYADSVKGR FTASRDNAGFSLFLQMNDLKPEDTAMYYCAAGD SPDGRCPPLGQGLNYWGQGTQVTVSSGGGGSGG GGSDIQMTQSPSSLSASVGDRVTITCRASENIYSYL AWYQQKPGKSPKLLIYNARTLAEGVPSRFSGSGS | SEQ ID NO: 106 |

TABLE 22-continued

Sequences of first and second polypeptide chains of anti-PVRIG/TIGIT
bispecific antibodies

| Antibody No. | Full-length amino acid sequences of heavy/light chains | Sequence No. |
|---|---|---|
| | GTDFTLTISSLQPEDFATYYCQYHSGSPLPFGGGTK VEIKRTVAAPSVFIFPPSDEQLKSGTASVVCLLNNF YPREAKVQWKVDNALQSGNSQESVTEQDSKDST YSLSSTLTLSKADYEKHKVYACEVTHQGLSSPVT KSFNRGEC | |
| 1708-151-4 (151 linked to C-terminal of light chain of 1708) | First polypeptide chain | Same as heavy chain of 1708 | SEQ ID NO: 102 |
| | Second polypeptide chain | DIQMTQSPSSLSASVGDRVTITCRASENIYSYLAW YQQKPGKSPKLLIYNARTLAEGVPSRFSGSGSGTD FTLTISSLQPEDFATYYCQYHSGSPLPFGGGTKVEI KRTVAAPSVFIFPPSDEQLKSGTASVVCLLNNFYPR EAKVQWKVDNALQSGNSQESVTEQDSKDSTYSL SSTLTLSKADYEKHKVYACEVTHQGLSSPVTKSF NRGEC<u>GGGGSGGGGS</u>HVQLVESGGGSVQAGGSL RLSCVASASGFTYRPYCMAWFRQAPGKEREAVAG IDIFGGTTYADSVKGRFTASRDNAGFSLFLQMNDL KPEDTAMYYCAAGDSPDGRCPPLGQGLNYWGQ GTQVTVSS | SEQ ID NO: 107 |

TABLE 23

Sequences of heavy and light chain CDRs of anti-TIGIT antibodies
(Kabat numbering scheme)

| Antibodies | Heavy chain | | Light chain | |
|---|---|---|---|---|
| 1707 | HCDR1 | DYHMY (SEQ ID NO: 115) | LCDR1 | KASQDVGTSVA (SEQ ID NO: 118) |
| | HCDR2 | YISKGGISTYYPDTVKG (SEQ ID NO: 116) | LCDR2 | WASARHT (SEQ ID NO: 119) |
| | HCDR3 | QSSYDFAMDY (SEQ ID NO: 117) | LCDR3 | QQYSSYPLT (SEQ ID NO: 120) |
| 1708 | HCDR1 | NYWMH (SEQ ID NO: 121) | LCDR1 | RASENIYSYLA (SEQ ID NO: 124) |
| | HCDR2 | RIDPDSTGSKYNEKFKT (SEQ ID NO: 122) | LCDR2 | NARTLAE (SEQ ID NO: 125) |
| | HCDR3 | EGAYGYYFDY (SEQ ID NO: 123) | LCDR3 | QYHSGSPLP (SEQ ID NO: 126) |
| 1709 | HCDR1 | DYYMH (SEQ ID NO: 127) | LCDR1 | KASQNVVTAVA (SEQ ID NO: 130) |
| | HCDR2 | LVYPYNDNTGYNRKFKG (SEQ ID NO: 128) | LCDR2 | SASNRYT (SEQ ID NO: 131) |
| | HCDR3 | GGPSNWNYFDY (SEQ ID NO: 129) | LCDR3 | QQYTLYPLT (SEQ ID NO: 132) |
| 1710 | HCDR1 | NYYMH (SEQ ID NO: 133) | LCDR1 | RTSENIFTYLA (SEQ ID NO: 136) |
| | HCDR2 | RIDPTSGATKYNDNFKG (SEQ ID NO: 134) | LCDR2 | NAKTFAE (SEQ ID NO: 137) |
| | HCDR3 | EGGFGYYFDY (SEQ ID NO: 135) | LCDR3 | QHHYGIPLP (SEQ ID NO: 138) |
| 1711 | HCDR1 | NYWIG (SEQ ID NO: 139) | LCDR1 | KSSQSLLYSRNQMNYLA (SEQ ID NO: 142) |
| | HCDR2 | DIYPGGAYTNYNEKFKD (SEQ ID NO: 140) | LCDR2 | WTSTRES (SEQ ID NO: 143) |
| | HCDR3 | GDYYDSSGRAMDY (SEQ ID NO: 141) | LCDR3 | QQYYSYPYT (SEQ ID NO: 144) |

TABLE 24

| Sequences of heavy chain VH and light chain VL of anti-TIGIT antibodies | |
|---|---|
| Antibodies | Sequences of heavy chain VH and light chain VL |
| 1708-VH1 | EVQLVQSGAEVKKPGASVKVSCKASGYTFTNYWMHWVRQAPGQGLEWMG RIDPDSTGSKYNEKFKTRVTMTRDTSTSTVYMELSSLRSEDTAVYYCAREGAY GYYFDYWGQGTLVTVSS (SEQ ID NO: 145) |
| 1708-VH2 | EVQLVQSGAEVKKPGASVKVSCKASGYTFTNYWMHWVRQAPGQGLEWMG RIDPDSTGSKYNEKFKTRVTMTVDTSTSTVYMELSSLRSEDTAVYYCAREGAY GYYFDYWGQGTLVTVSS (SEQ ID NO: 146) |
| 1708-VH3 | EVQLVQSGAEVKKPGASVKVSCKASGYTFTNYWMHWVRQAPGQGLEWIGRI DPDSTGSKYNEKFKTRVTMTVDTSTSTAYMELSSLRSEDTAVYYCAREGAYGY YFDYWGQGTLVTVSS (SEQ ID NO: 147) |
| 1708-VL1 | DIQMTQSPSSLSASVGDRVTITCRASENIYSYLAWYQQKPGKAPKLLIYNARTL AEGVPSRFSGSGSGTDFTLTISSLQPEDFATYYCQYHSGSPLPFGGGTKVEIK (SEQ ID NO: 148) |
| 1708-VL2 | DIQMTQSPSSLSASVGDRVTITCRASENIYSYLAWYQQKPGKSPKLLIYNARTL AEGVPSRFSGSGSGTDFTLTISSLQPEDFATYYCQYHSGSPLPFGGGTKVEIK (SEQ ID NO: 149) |

Transient transfection, expression and purification of the antibodies were carried out according to conventional methods. Identification was performed, and the full-length anti-PVRIG/TIGIT bispecific antibodies of the present disclosure were obtained. The expression level and purity of the bispecific antibodies are shown in Table 25. Coupling a Nanobody® to a common monoclonal antibody, whether via the N-terminal or the C-terminal of a heavy or light chain, results in good expression level and purity.

TABLE 25

| Expression level and purity of anti-PVRIG/TIGIT bispecific antibodies | | |
|---|---|---|
| Antibody No. | Expression level (mg/L) | SEC purity (%) |
| 1708-151-1 | 140 | 97.6 |
| 1708-151-2 | 108 | 95.7 |
| 1708-151-3 | 160 | 94.7 |
| 1708-151-4 | 158 | 96.2 |

Example 17: Experiment on Binding of Anti-PVRIG/TIGIT Bispecific Antibodies to PVRIG and TIGIT and Blocking of Corresponding Ligands A) Binding of Bispecific Antibodies with Different Configurations to Human PVRIG and Blocking of Ligand PVRL2

The experiments were carried out according to the methods of Example 4, Example 5 and Example 6, and the results are shown in Table 26. The results show that the bispecific antibodies with different configurations are basically the same and have no difference in binding to human PVRIG recombinant protein and cells over-expressing human PVRIG and in blocking the binding of PVRL2 to PVRIG.

TABLE 26

| Binding of bispecific antibodies to PVRIG and blocking of ligand | | | |
|---|---|---|---|
| Antibody No. | Binding to human PVRIG recombinant protein EC$_{50}$ (nM) | Binding to cells overexpressing human PVRIG EC$_{50}$ (nM) | Blocking binding of human PVRIG to human PVRL2 IC$_{50}$ (nM) |
| 1708-151-1 | 1.864 | 0.05 | 0.757 |
| 1708-151-2 | 2.391 | 0.21 | 0.824 |
| 1708-151-3 | 1.579 | 0.06 | 0.712 |
| 1708-151-4 | 1.671 | 0.49 | 0.743 |
| Tab5 | 1.857 | 3.15 | 0.797 |
| IgG4 | No binding | No binding | No blocking |

B) Binding of Bispecific Antibodies with Different Configurations to Human TIGIT and Blocking of Ligand PVR The experiments were carried out according to the methods of Example 4, Example 5 and Example 6 (corresponding receptors and ligands were replaced with human TIGIT and human PVR), and the results are shown in Table 27. The results show that the bispecific antibodies with different configurations and the anti-TIGIT antibody are basically the same and have no difference in binding to human TIGIT recombinant protein and cells over-expressing human TIGIT and in blocking the binding of TIGIT to its ligand PVR. The manner of linkage of the anti-PVRIG antibody 151 almost has no effect on the binding of anti-TIGIT antibody to TIGIT.

TABLE 27

| Binding of bispecific antibodies to TIGIT and blocking of ligand | | | |
|---|---|---|---|
| Antibody No. | Binding to human TIGT recombinant protein EC$_{50}$ (nM) | Binding to cells overexpressing human TIGIT EC$_{50}$ (nM) | Blocking binding of human TIGIT to human PVR IC$_{50}$ (nM) |
| 1708-151-1 | 0.101 | 1.51 | 0.96 |
| 1708-151-2 | 0.090 | 1.27 | 1.04 |
| 1708-151-3 | 0.069 | 1.92 | 0.62 |

TABLE 27-continued

| Binding of bispecific antibodies to TIGIT and blocking of ligand | | | |
|---|---|---|---|
| Antibody No. | Binding to human TIGT recombinant protein $EC_{50}$ (nM) | Binding to cells overexpressing human TIGIT $EC_{50}$ (nM) | Blocking binding of human TIGIT to human PVR $IC_{50}$ (nM) |
| 1708-151-4 | 0.054 | 1.00 | 0.69 |
| 1708 | 0.055 | 0.74 | 0.87 |
| IgG4 | No binding | No binding | No blocking |

With reference to the data in Tables 24-25, it is found that the anti-PVRIG antibody, whether linked to the N-terminal or C-terminal of the heavy or light chain of the anti-TIGIT antibody, maintains its binding to PVRIG and TIGIT and blocking of the ligand, and shows good expression level and purity.

Example 18: Preparation of Humanized Anti-PVRIG/TIGIT Bispecific Antibodies

Different humanized anti-PVRIG antibodies (20H5, 30H2, 39H2, 151H7 and 151H8) were each linked to the N-terminal of the heavy chain of the anti-TIGIT antibody 1708 (i.e., using a bispecific antibody configuration similar to 1708-151-1) to construct diabodies, and the sequences are shown in Table 28.

TABLE 28

| Full-length sequences of first and second polypeptide chains of humanized anti-PVRIG/TIGIT bispecific antibodies | | | |
|---|---|---|---|
| Antibody No. | | Full-length amino acid sequences of first and second polypeptide chains | Sequence No. |
| 1708-20H5 | First polypeptide chain | EVQLVESGGGLVQPGGSLRLSCAASGYTSRTD CMGWFRQAPGKEHEGVAHIDSDGIPRYVDSV KGRFTISQDHAKNSLYLQMNSLRAEDTAVYY CVVGFKFDEDYCAPNDWGQGTMVTVSSGGG GSGGGGSEVQLVQSGAEVKKPGASVKVSCKA SGYTFTNYWMHWVRQAPGQGLEWMGRIDP DSTGSKYNEKFKTRVTMTRDTSTSTVYMELS SLRSEDTAVYYCAREGAYGYYFDYWGQGTLV TVSSASTKGPSVFPLAPCSRSTSESTAALGCLV KDYFPEPVTVSWNSGALTSGVHTFPAVLQSSG LYSLSSVVTVPSSSLGTKTYTCNVDHKPSNTK VDKRVESKYGPPCPPCPAPEFLGGPSVFLFPPK PKDTLMISRTPEVTCVVVDVSQEDPEVQFNW YVDGVEVHNAKTKPREEQFNSTYRVVSVLTV LHQDWLNGKEYKCKVSNKGLPSSIEKTISKA KGQPREPQVYTLPPSQEEMTKNQVSLTCLVK GFYPSDIAVEWESNGQPENNYKTTPPVLDSDG SFFLYSRLTVDKSRWQEGNVFSCSVMHEALH NHYTQKSLSLSLGK | SEQ ID NO: 108 |
| | Second polypeptide chain | Same as light chain of 1708 | SEQ ID NO: 103 |
| 1708-30H2 | First polypeptide chain | EVQLVESGGGLVQPGGSLRLSCAASGFTFSGD CMGWFRQAPGKGLDEGVATIDNAGRIKYADS VKGRFTISRDNAKNSLYLQMNSLRAEDTAVY YCAAGWTFGGQCSPADWGQGTQVTVSSGGG GSGGGGSEVQLVQSGAEVKKPGASVKVSCKA SGYTFTNYWMHWVRQAPGQGLEWMGRIDP DSTGSKYNEKFKTRVTMTRDTSTSTVYMELS SLRSEDTAVYYCAREGAYGYYFDYWGQGTLV TVSSASTKGPSVFPLAPCSRSTSESTAALGCLV KDYFPEPVTVSWNSGALTSGVHTFPAVLQSSG LYSLSSVVTVPSSSLGTKTYTCNVDHKPSNTK VDKRVESKYGPPCPPCPAPEFLGGPSVFLFPPK PKDTLMISRTPEVTCVVVDVSQEDPEVQFNW YVDGVEVHNAKTKPREEQFNSTYRVVSVLTV LHQDWLNGKEYKCKVSNKGLPSSIEKTISKA KGQPREPQVYTLPPSQEEMTKNQVSLTCLVK GFYPSDIAVEWESNGQPENNYKTTPPVLDSDG SFFLYSRLTVDKSRWQEGNVFSCSVMHEALH NHYTQKSLSLSLGK | SEQ ID NO: 109 |
| | Second polypeptide chain | Same as light chain of 1708 | SEQ ID NO: 103 |
| 1708-39H2 | First polypeptide chain | EVQLVESGGGLVQPGGSLRLSCAASGFTSRTD CMGWFRQAPGKGLEGVAHIDSDGIPRYVESV KGRFTISRDNAKNSLYLQMNSLRAEDTAVYY CVVGFKFGDYCAPNDWGQGTMVTVSSGGGG SGGGGSEVQLVQSGAEVKKPGASVKVSCKAS GYTFTNYWMHWVRQAPGQGLEWMGRIDPD STGSKYNEKFKTRVTMTRDTSTSTVYMELSSL RSEDTAVYYCAREGAYGYYFDYWGQGTLVT VSSASTKGPSVFPLAPCSRSTSESTAALGCLVK | SEQ ID NO: 110 |

TABLE 28-continued

Full-length sequences of first and second polypeptide chains of
humanized anti-PVRIG/TIGIT bispecific antibodies

| Antibody No. | Full-length amino acid sequences of first and second polypeptide chains | | Sequence No. |
|---|---|---|---|
| | | DYFPEPVTVSWNSGALTSGVHTFPAVLQSSGL YSLSSVVTVPSSSLGTKTYTCNVDHKPSNTKV DKRVESKYGPPCPPCPAPEFLGGPSVFLFPPKP KDTLMISRTPEVTCVVVDVSQEDPEVQFNWY VDGVEVHNAKTKPREEQFNSTYRVVSVLTVL HQDWLNGKEYKCKVSNKGLPSSIEKTISKAK GQPREPQVYTLPPSQEEMTKNQVSLTCLVKGF YPSDIAVEWESNGQPENNYKTTPPVLDSDGSF FLYSRLTVDKSRWQEGNVFSCSVMHEALHNH YTQKSLSLSLGK | |
| | Second polypeptide chain | Same as light chain of 1708 | SEQ ID NO: 103 |
| 1708-151H7 | First polypeptide chain | HVQLVESGGGLVQPGGSLRLSCVASASGFTYR PYCMAWFRQAPGKEREAVAGIDIFGGTTYADS VKGRFTASRDNAGFSLYLQMNSLRAEDTAVY YCAAGDSPDGRCPPLGQGLNYWGQGTMVTV SSGGGGSGGGGSEVQLVQSGAEVKKPGASVK VSCKASGYTFTNYWMHWVRQAPGQGLEWM GRIDPDSTGSKYNEKFKTRVTMTRDTSTSTVY MELSSLRSEDTAVYYCAREGAYGYYFDYWG QGTLVTVSSASTKGPSVFPLAPCSRSTSESTAA LGCLVKDYFPEPVTVSWNSGALTSGVHTFPAV LQSSGLYSLSSVVTVPSSSLGTKTYTCNVDHK PSNTKVDKRVESKYGPPCPPCPAPEFLGGPSVF LFPPKPKDTLMISRTPEVTCVVVDVSQEDPEV QFNWYVDGVEVHNAKTKPREEQFNSTYRVV SVLTVLHQDWLNGKEYKCKVSNKGLPSSIEK TISKAKGQPREPQVYTLPPSQEEMTKNQVSLT CLVKGFYPSDIAVEWESNGQPENNYKTTPPVL DSDGSFFLYSRLTVDKSRWQEGNVFSCSVMH EALHNHYTQKSLSLSLGK | SEQ ID NO: 111 |
| | Second polypeptide chain | Same as light chain of 1708 | SEQ ID NO: 103 |
| 1708-151H8 | First polypeptide chain | EVQLVESGGGLVQPGGSLRLSCVASASGFTYR PYCMAWFRQAPGKGLEAVAGIDIFGGTTYADS VKGRFTISRDNAGFSLYLQMNSLRAEDTAVYY CAAGDSPDGRCPPLGQGLNYWGQGTMVTVS SGGGGSGGGGSEVQLVQSGAEVKKPGASVK VSCKASGYTFTNYWMHWVRQAPGQGLEWM GRIDPDSTGSKYNEKFKTRVTMTRDTSTSTVY MELSSLRSEDTAVYYCAREGAYGYYFDYWG QGTLVTVSSASTKGPSVFPLAPCSRSTSESTAA LGCLVKDYFPEPVTVSWNSGALTSGVHTFPAV LQSSGLYSLSSVVTVPSSSLGTKTYTCNVDHK PSNTKVDKRVESKYGPPCPPCPAPEFLGGPSVF LFPPKPKDTLMISRTPEVTCVVVDVSQEDPEV QFNWYVDGVEVHNAKTKPREEQFNSTYRVV SVLTVLHQDWLNGKEYKCKVSNKGLPSSIEK TISKAKGQPREPQVYTLPPSQEEMTKNQVSLT CLVKGFYPSDIAVEWESNGQPENNYKTTPPVL DSDGSFFLYSRLTVDKSRWQEGNVFSCSVMH EALHNHYTQKSLSLSLGK | SEQ ID NO: 112 |
| | Second polypeptide chain | Same as light chain of 1708 | SEQ ID NO: 103 |

Transient transfection, expression and purification of the antibodies were carried out according to conventional methods. Identification was performed, and the diabodies of interest were obtained.

Example 19: Binding of Humanized Anti-PVRIG/TIGIT Bispecific Antibodies to PVRIG and TIGIT and Blocking of Corresponding Ligands Binding of the humanized anti-PVRIG/TIGIT bispecific antibodies to human and cynomolgus monkey PVRIG and their blocking of the ligand of human PVRIG were detected according to the methods of Examples 4, 5 and 6. The results are shown in Table 29 and FIGS. 6A-6E. The results show that each humanized bispecific antibody can bind to human PVRIG and block the binding of PVRIG to PVRL2. 1708-151H8 shows weak binding to cynomolgus monkey PVRIG.

TABLE 29

| | Binding of humanized bispecific antibodies to PVRIG and blocking of ligand | | | | |
|---|---|---|---|---|---|
| Antibody No. | Binding to human PVRIG recombinant protein $EC_{50}$ (nM) | Binding to cells overexpressing human PVRIG $EC_{50}$ (nM) | Binding to cynomolgus monkey PVRIG recombinant protein $EC_{50}$ (nM) | Binding to cells overexpressing cynomolgus monkey PVRIG $EC_{50}$ (nM) | Blocking binding of human PVRIG to human PVRL2 $IC_{50}$ (nM) |
| 1708-20H5 | 2.466 | 0.075 | 0.144 | 0.070 | 0.628 |
| 1708-30H2 | 0.320 | 0.056 | 0.184 | 3.540 | 0.552 |
| 1708-39H2 | 1.805 | 0.079 | 0.133 | 0.293 | 0.619 |
| 1708-151H7 | 0.679 | 0.043 | 9.442 | 11.470 | 0.598 |
| 1708-151H8 | 0.390 | 0.094 | N.A. | N.A. | 0.654 |
| 1708 | No binding | No binding | No binding | No binding | Not tested |
| Tab5 | 1.407 | 0.789 | No binding | No binding | 0.964 |
| IgG4 | No binding | No binding | No binding | No binding | No blocking |

Similar to Examples 4, 5 and 6, the binding of humanized anti-PVRIG/TIGIT bispecific antibodies to human and cynomolgus monkey TIGIT and blocking of binding of human TIGIT to ligand were detected, where PVRIG protein was replaced with TIGIT and PVRL2 was replaced with PVR. The results are shown in Table 30 and FIGS. 7A-7E. The results show that each diabody can bind to human and cynomolgus monkey TIGIT to block the binding of TIGIT to PVR.

TABLE 30

| | Binding of humanized bispecific antibodies to TIGIT and blocking of ligand | | | | |
|---|---|---|---|---|---|
| Antibody No. | Binding to human TIGIT recombinant protein $EC_{50}$ (nM) | Binding to cells overexpressing human TIGIT $EC_{50}$ (nM) | Binding to cynomolgus monkey TIGIT recombinant protein $EC_{50}$ (nM) | Binding to cells overexpressing cynomolgus monkey TIGIT $EC_{50}$ (nM) | Blocking binding of human TIGIT to human PVR $IC_{50}$ (nM) |
| 1708-20H5 | 0.145 | 0.010 | 0.112 | 0.009 | 1.018 |
| 1708-30H2 | 0.153 | 0.010 | 0.114 | 0.009 | 1.014 |
| 1708-39H2 | 0.135 | 0.005 | 0.105 | 0.005 | 0.812 |
| 1708-151H7 | 0.160 | 0.012 | 0.119 | 0.012 | 0.773 |
| 1708-151H8 | 0.184 | 0.006 | 0.135 | 0.011 | 1.087 |
| 1708 | 0.133 | 0.0027 | 0.104 | 0.003 | 0.779 |
| Tab5 | No binding | No binding | No binding | No binding | Not tested |
| IgG4 | No binding | No binding | No binding | No binding | No blocking |

The affinity of the humanized bispecific antibodies for human PVRIG, cynomolgus monkey PVRIG and human TIGIT was detected using Biacore®. Humanized bispecific antibodies were each captured on a Protein A biosensor chip (GE lifesciences, 29127557) of a Biacore® instrument (Biacore® X100, GE), and then human PVRIG antigen (Acro-Biosystem, PVG-H52H4), cynomolgus monkey PVRIG antigen (SEQ ID NO: 1) or human TIGIT antigen (Acro-Biosystem, TIT-H52H3) at a series of concentration gradients each flowed over the chip surface. The reaction signals were detected in real time using a Biacore® instrument (Biacore® X100, GE) to obtain association and dissociation curves. The data obtained from the experiment were fitted using the (1:1) Binding model with the Biacore® X100 evaluation software 2.0 GE to obtain affinity values (see Table 31).

TABLE 31

| | Affinity of humanized bispecific antibodies for human PVRIG, cynomolgus monkey PVRIG and human TIGIT | | | |
|---|---|---|---|---|
| Antibody No. | Antigens | kon (1/Ms) | koff (1/s) | KD (M) |
| 1708-20H5 | Human PVRIG | 1.67E+07 | 1.30E−04 | 7.82E−12 |
| 1708-30H2 | | 1.29E+07 | 9.12E−03 | 7.06E−10 |

TABLE 31-continued

| | Affinity of humanized bispecific antibodies for human PVRIG, cynomolgus monkey PVRIG and human TIGIT | | | |
|---|---|---|---|---|
| Antibody No. | Antigens | kon (1/Ms) | koff (1/s) | KD (M) |
| 1708-39H2 | | 7.90E+06 | 2.76E−04 | 3.49E−11 |
| 1708-151H7 | | 6.06E+06 | 7.57E−04 | 1.25E−10 |
| 1708-20H5 | Human TIGIT | 1.97E+06 | 1.50E−04 | 7.63E−11 |
| 1708-30H2 | | 3.08E+06 | 1.58E−04 | 5.12E−11 |
| 1708-39H2 | | 1.39E+06 | 1.13E−04 | 8.08E−11 |
| 1708-151H7 | | 1.40E+06 | 1.16E−04 | 8.28E−11 |
| 1708-20H5 | Cynomolgus | 2.56E+07 | 1.81E−01 | 7.05E−09 |
| 1708-30H2 | monkey PVRIG | 1.82E+07 | 5.81E−01 | 3.19E−08 |
| 1708-39H2 | | 8.48E+07 | 2.52E+00 | 2.97E−08 |

Figure 8:
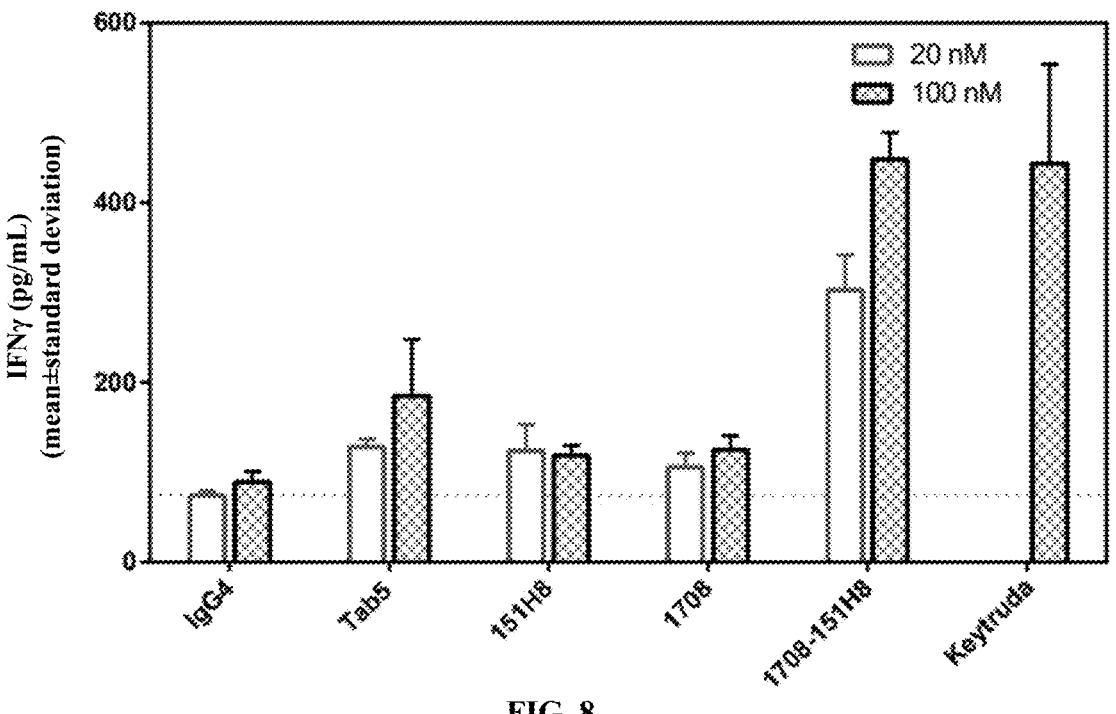
FIG. 8 shows the detection results of the activity of humanized anti-PVRIG/TIGIT bispecific antibodies in activating T cells in MLR experiment.

Example 20: Mixed Lymphocyte Reaction (MLR) Experiment of Humanized Anti-PVRIG/TIGIT Bispecific Antibody The ability of the humanized anti-PVRIG/TGIT bispecific antibody to activate T cells was detected according to the method of Example 10. The results of the experiment are shown in FIG. 8 and Table 32. The results show that the humanized anti-PVRIG/TIGIT bispecific antibody 1708-15118 can significantly activate T cells and promote the secretion of IFNγ by T cells. Importantly, the activity of the bispecific antibody is stronger than that of anti-PVRIG antibody 151H8 alone or ant-TIGIT antibody 1708 alone.

TABLE 32

| IFNγ secretion level in mixed lymphocyte reaction of humanized bispecific antibody | | |
|---|---|---|
| | IFNγ (pg/mL) (mean ± standard deviation) | |
| Antibody No. | 20 nM antibody | 100 nM antibody |
| IgG4 | 74 ± 5 | 89 ± 12 |
| 151H8 | 124 ± 29 | 118 ± 11 |

TABLE 32-continued

| IFNγ secretion level in mixed lymphocyte reaction of humanized bispecific antibody | | |
|---|---|---|
| | IFNγ (pg/mL) (mean ± standard deviation) | |
| Antibody No. | 20 nM antibody | 100 nM antibody |
| 1708 | 106 ± 16 | 125 ± 16 |
| 1708-151H8 | 303 ± 40 | 448 ± 40 |
| Tab5 | 128 ± 8.9 | 185 ± 63 |
| Keytruda | Not tested | 444 ± 111 |

Example 21: Evaluation of Anti-Tumor Effect of Anti-PVRIG/TIGIT Bispecific Antibodies in a Mouse Subcutaneous Xenograft Tumor Model of Human Melanoma A375 Mixed with Human PBMCs To further explore the role of the bispecific antibody subtype in animal efficacy, in addition to the bispecific antibodies of the IgG4 subtype described above, corresponding antibodies of the IgG1 subtype were also synthesized for use in animal efficacy test. Other antibody sequences used in this experiment and not described previously are shown in Table 33.

TABLE 33

| Full-length sequences of first and second polypeptide chains of humanized anti-PVRIG/TIGIT bispecific antibodies of type IgG1 | | | |
|---|---|---|---|
| Antibody No. | | Full-length amino acid sequences of first and second polypeptide chains | Sequence No. |
| 1708-IgG1 (same as 1708, except the heavy chain constant region subtype was changed to IgG1) | HC | EVQLVQSGAEVKKPGASVKVSCKASGYTFTNY WMHWVRQAPGQGLEWMGRIDPDSTGSKYNE KFKTRVTMTRDTSTSTVYMELSSLRSEDTAVY YCAREGAYGYYFDYWGQGTLVTVSSASTKGP SVFPLAPSSKSTSGGTAALGCLVKDYFPEPVTV SWNSGALTSGVHTFPAVLQSSGLYSLSSVVTVP SSSLGTQTYICNVNHKPSNTKVDKKVEPKSCD KTHTCPPCPAPELLGGPSVFLFPPKPKDTLMISR TPEVTCVVVDVSHEDPEVKFNWYVDGVEVHN AKTKPREEQYNSTYRVVSVLTVLHQDWLNGK EYKCKVSNKALPAPIEKTISKAKGQPREPQVYT LPPSREEMTKNQVSLTCLVKGFYPSDIAVEWES NGQPENNYKTTPPVLDSDGSFFLYSKLTVDKSR WQQGNVFSCSVMHEALHNHYTQKSLSLSPGK | SEQ ID NO: 113 |
| | LC | Same as light chain of 1708 | SEQ ID NO: 103 |
| 1708-151-IgG1 (same as 1708-151, except the heavy chain constant region subtype was changed to IgG1) | First polypeptide chain | HVQLVESGGGSVQAGGSLRLSCVASASGFTYR PYCMAWFRQAPGKEREAVAGIDIFGGTTYADS VKGRFTASRDNAGFSLFLQMNDLKPEDTAMY YCAAGDSPDGRCPPLGQGLNYWGQGTQVTVS SGGGGSGGGGSEVQLVQSGAEVKKPGASVKV SCKASGYTFTNYWMHWVRQAPGQGLEWMGR IDPDSTGSKYNEKFKTRVTMTRDTSTSTVYME LSSLRSEDTAVYYCAREGAYGYYFDYWGQGTL VTVSSASTKGPSVFPLAPSSKSTSGGTAALGCL VKDYFPEPVTVSWNSGALTSGVHTFPAVLQSSG LYSLSSVVTVPSSSLGTQTYICNVNHKPSNTKV DKKVEPKSCDKTHTCPPCPAPELLGGPSVFLFP PKPKDTLMISRTPEVTCVVVDVSHEDPEVKFN WYVDGVEVHNAKTKPREEQYNSTYRVVSVLT VLHQDWLNGKEYKCKVSNKALPAPIEKTISKA KGQPREPQVYTLPPSREEMTKNQVSLTCLVKG FYPSDIAVEWESNGQPENNYKTTPPVLDSDGSF FLYSKLTVDKSRWQQGNVFSCSVMHEALHNH YTQKSLSLSPGK | SEQ ID NO: 114 |
| | Second polypeptide chain | Same as light chain of 1708 | SEQ ID NO: 103 |

NCG mice, female, aged 4-8 weeks, weighed about 18-22 g, purchased from Jiangsu GemPharmatech Co., Ltd. All NCG mice were fed in an IVC constant temperature and pressure system in a SPF-grade animal room.

A375 cells were cultured in DMEM medium containing 10% fetal bovine serum (FBS). A375 cells in the exponential phase were collected and resuspended in HBSS to an appropriate concentration for subcutaneous tumor inoculation in NCG mice. The A375 cells used for co-culture were treated with Mitomycin C for 2 h and washed three times with PBS. Peripheral blood of a normal human was taken, and human PBMCs were isolated by density gradient centrifugation and counted. The PBMCs were then resuspended to a concentration of $3 \times 10^6$ cells/mL with RPMI1640 medium (containing IL2 and 10% FBS) and co-cultured with Mitomycin C-treated A375 cells. After 6 days of co-culture, PBMCs were harvested together with freshly digested A375 cells. Each mouse was inoculated with $5 \times 10^5$ PBMCs and $4 \times 10^6$ A375 cells, the inoculation volume was 0.2 mL/mouse (containing 50% Matrigel®), and the cells were inoculated subcutaneously on the right side of female NCG mice. The mice were randomly divided, according to the body weight, into groups for drug administration, the detailed administration method, dose of administration and route of administration are shown in Table 34, and the day of the grouping and administration was day 0. Due to the different molecular weights of the anti-PVRIG antibody and anti-TIGIT antibody, the dose of administration ensured that the anti-PVRIG antibody and anti-TIGIT antibody had the same starting molar concentration.

TABLE 34

Administration regimen

| Groups | Administration group | N | Dose (mg/kg) | Administration regimen | Route of administration |
|---|---|---|---|---|---|
| 1 | hIgG1 | 7 | 30 | Q2D | i.p. |
| 2 | 151-IgG4 | 7 | 16.1 | Q2D | i.p. |
| 3 | 1708-IgG1 | 7 | 30 | Q2D | i.p. |
| 4 | 151-IgG4 + | 7 | 16.1 | Q2D | i.p. |
| | 1708-IgG1 | | 30 | Q2D | i.p. |
| 5 | 1708-151 IgG1 | 7 | 35.8 | Q2D | i.p. |
| 6 | 1708-151 IgG4 | 7 | 35.8 | Q2D | i.p. |

Note:
(N: number of animals used; i.p.: intraperitoneal injection; Q2D: once every two days; volume for administration: adjusted according to body weight of tumor-bearing mouse (0.1 mL/10 g).)

Figures 9A, 9B:
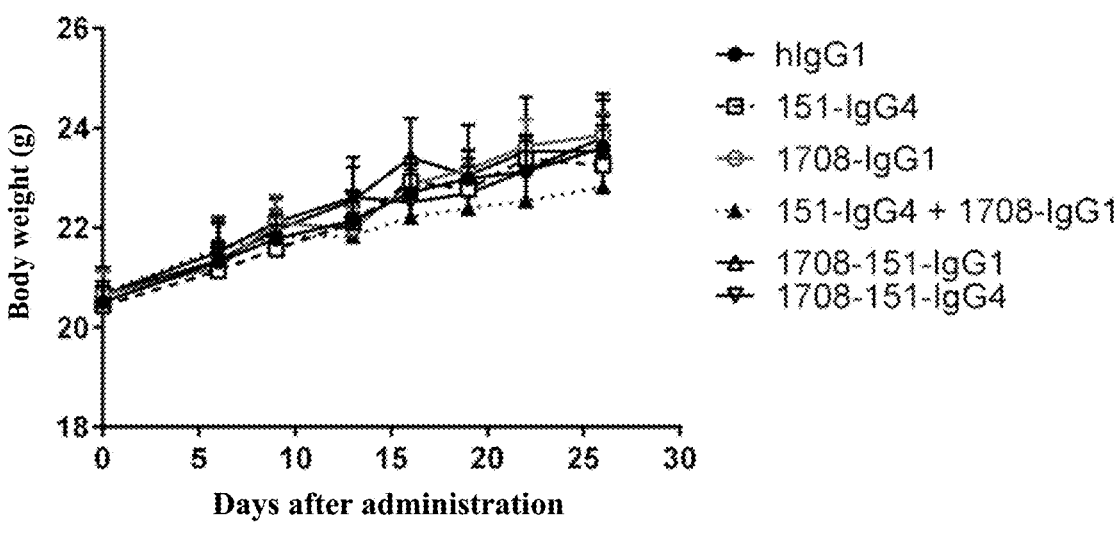
FIGS. 9A-9B show the effect of anti-PVRIG/TIGIT bispecific antibodies on mouse body weight and tumor volume, respectively, in mouse subcutaneous xenograft tumor models of human melanoma A375 mixed with human PBMCs.

After the start of administration, the body weight and tumor volume of the mice were measured twice a week. The results are shown in Tables 35-36 and FIGS. 9A-9B.

TABLE 35

Effect of anti-PVRIG/TIGIT bispecific antibodies on body weight of mice

| Groups | Average body weight on day 0 (g) (mean ± standard deviation) | Average body weight on day 26 (g) (mean ± standard deviation) | Rate of change in body weight (%) (mean ± standard deviation) |
|---|---|---|---|
| 1 | 20.5 ± 0.42 | 23.60 ± 0.64 | 15.21 ± 2.88 |
| 2 | 20.43 ± 0.4 | 23.77 ± 0.74 | 16.54 ± 2.57 |
| 3 | 20.65 ± 0.48 | 23.85 ± 0.45 | 15.71 ± 2.08 |
| 4 | 20.69 ± 0.51 | 22.81 ± 0.78 | 10.14 ± 1.45 |
| 5 | 20.65 ± 0.56 | 23.54 ± 1.14 | 13.77 ± 3.26 |
| 6 | 20.65 ± 0.48 | 23.8 ± 0.76 | 15.28 ± 2.58 |

TABLE 36

Anti-tumor effect of anti-PVRIG/TIGIT bispecific antibodies in mouse human-derived A375 tumor model

| Groups | Tumor volume on day 0 (mm³) | Tumor volume on day 26 (mm³) (mean ± standard deviation) | TGI (%) | T/C (%) | P value |
|---|---|---|---|---|---|
| 1 | 0 ± 0 | 1913.62 ± 188.23 | — | — | — |
| 2 | 0 ± 0 | 1942.70 ± 223.36 | −1.52 | 101.52 | 0.916 |
| 3 | 0 ± 0 | 958.83 ± 204.39 | 49.89 | 50.11 | <0.001xxx |
| 4 | 0 ± 0 | 876.21 ± 243.70 | 54.21 | 45.79 | <0.001xxx |
| 5 | 0 ± 0 | 629.64 ± 163.74 | 67.10 | 32.90 | <0.001xxx |
| 6 | 0 ± 0 | 79.99 ± 36.57 | 95.82 | 4.18 | <0.001xxx |

Note:
($xP < 0.05$, $xxP < 0.01$ and $xxxP < 0.001$ are considered to have significant differences compared with the control group (hIgG1).)

At the end of the experiment (day 26 post-administration), the anti-PVRIG antibody 151 single drug group showed no significant difference compared with the control group. In the anti-TIGIT antibody 1708-IgG1 single drug group, the anti-PVRIG antibody 151 and anti-TIGIT antibody 1708-IgG1 combination group and the 1708-151-IgG1 diabody group, tumor volume was reduced. The 1708-151-IgG4 diabody group could even completely inhibit tumor growth, exhibiting significant difference from the other groups (see FIG. 9B).

The mice were randomly divided, according to the body weight, into groups for drug administration, the detailed administration method, dose of administration and route of administration are shown in Table 37, and the day of the grouping and administration was day 0.

TABLE 37

Administration regimen

| Groups | Administration group | Number | Dose (mg/kg) | Administration regimen | Route of administration |
|---|---|---|---|---|---|
| 1 | hIgG4 | 7 | 35.8 | Q2D | i.p. |
| 2 | 1708-30H2 IgG4 | 7 | 12 | Q2D | i.p. |
| 3 | 1708-151H7 IgG4 | 7 | 12 | Q2D | i.p. |

Note:
(N: number of animals used; i.p.: intraperitoneal injection; Q2D: once every two days; volume for administration: adjusted according to body weight of tumor-bearing mouse (0.1 mL/10 g).)

After the start of administration, the body weight and tumor volume of the mice were measured twice a week. The results are shown in Tables 38-39 and FIGS. 10A-10B.

TABLE 38

Effect of anti-P RIG/TIGIT bispecific antibodies on body weight of mice

| Groups | Average body weight on day 0 (g) (mean ± standard deviation) | Average body weight on day 28 (g) (mean ± standard deviation) | Rate of change in body weight (%) (mean ± standard deviation) |
|---|---|---|---|
| 1 | 21.51 ± 0.53 | 25.38 ± 0.32 | 18.38 ± 3.27 |
| 2 | 21.57 ± 0.55 | 24.82 ± 0.46 | 15.34 ± 2.18 |
| 3 | 21.63 ± 0.47 | 24.87 ± 0.36 | 15.15 ± 1.38 |

TABLE 39

Anti-tumor effect of anti-PVRIG/TIGIT bispecific antibodies
in mouse human-derived A375 tumor model

| Groups | Tumor volume on day 0 (mm$^3$) | Tumor volume on day 28 (mm$^3$) (mean ± standard deviation) | TGI (%) | T/C (%) | P value |
|---|---|---|---|---|---|
| 1 | 0 ± 0 | 2239.26 ± 322.87 | — | — | — |
| 2 | 0 ± 0 | 1435.36 ± 117.61 | 35.90 | 64.10 | <0.05x |
| 3 | 0 ± 0 | 1468.96 ± 67.07 | 34.40 | 65.60 | <0.05x |

Note:
(xP < 0.05, xxP < 0.01 and xxxP < 0.001 are considered to have significant differences compared with the control group (hIgG1).)

Figure 10A:
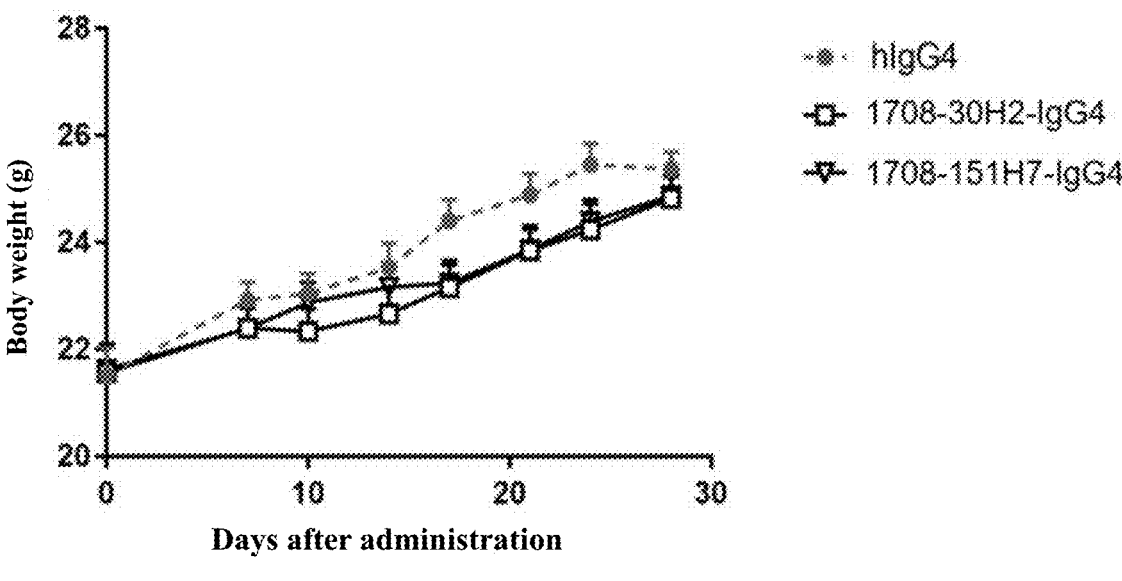
FIGS. 10A-10B show the effect of anti-PVRIG/TIGIT bispecific antibodies on mouse body weight and tumor volume, respectively, in mouse subcutaneous xenograft tumor models of human melanoma A375 mixed with human PBMCs.
Figure 10B:
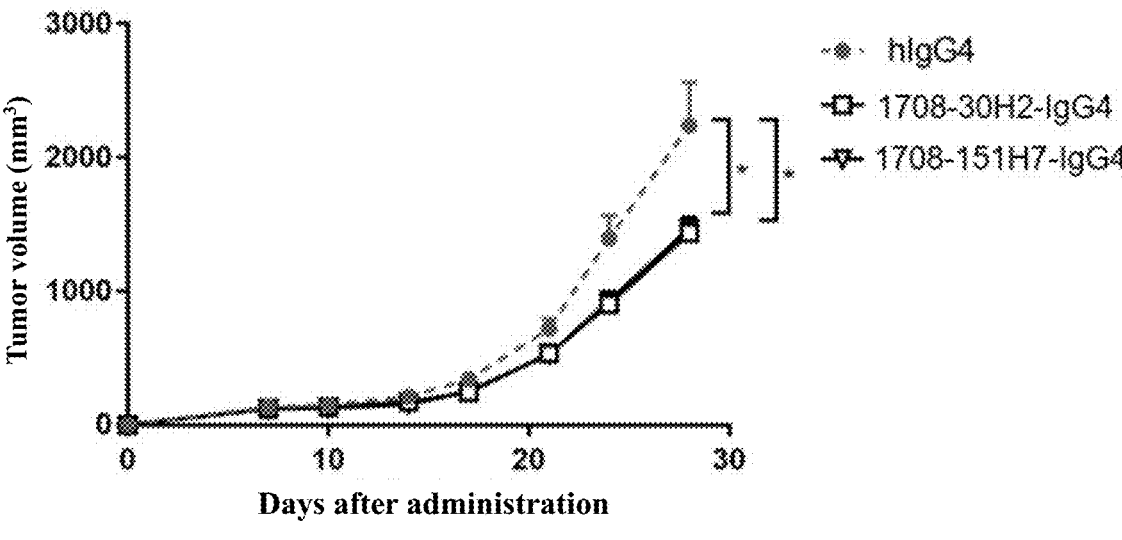

At the end of the experiment (day 28 post administration), both the 1708-30H2 IgG4 and 1708-151H7 IgG4 diabody groups were effective in inhibiting tumor growth at low doses compared with the control group, and exhibited significant difference from the control group (see FIG. 10A and FIG. 10B).

Although specific embodiments of the present disclosure have been described above, it will be appreciated by those skilled in the art that these embodiments are merely illustrative and that many changes or modifications can be made to these embodiments without departing from the principles and spirit of the present disclosure. The scope of protection of the present disclosure is therefore defined by the appended claims.

The invention claimed is:

1. A Poliovirus Receptor-Related Immunoglobulin Domain-Containing Protein (PVRIG) binding protein, comprising at least one immunoglobulin single variable domain comprising:

a CDR1, a CDR2 and a CDR3 having the amino acid sequences of the CDR1, the CDR2, and the CDR3, respectively, of the heavy chain variable region having the amino acid sequence selected from the group consisting of SEQ ID NOs: 3 and 80-84; or a CDR1, a CDR2 and a CDR3 having the amino acid sequences of the CDR1, the CDR2, and the CDR3, respectively, of the heavy chain variable region having the amino acid sequence selected from the group consisting of SEQ ID NOs: 2 and 75-79; or a CDR1, a CDR2 and a CDR3 having the amino acid sequences of the CDR1, the CDR2, and the CDR3, respectively, of the heavy chain variable region having the amino acid sequence selected from the group consisting of SEQ ID NOs: 4 and 86-90; or a CDR1, a CDR2 and a CDR3 having the amino acid sequences of the CDR1, the CDR2, and the CDR3, respectively, of the heavy chain variable region having the amino acid sequence selected from the group consisting of SEQ ID NOs: 5 and 91-95; or a CDR1, a CDR2 and a CDR3 having the amino acid sequences of the CDR1, the CDR2, and the CDR3, respectively, of the heavy chain variable region having the amino acid sequence selected from the group consisting of SEQ ID NOS: 6 and 96-100;

wherein the CDR1, the CDR2 and the CDR3 are defined according to Kabat, IMGT, Chothia, AbM or Contact numbering scheme.

2. The PVRIG binding protein according to claim 1, wherein the immunoglobulin single variable domain is a heavy chain single-domain antibody (VHH).

3. The PVRIG binding protein according to claim 1 wherein the immunoglobulin single variable domain comprises the amino acid sequence of:

any one of SEQ ID NOs: 3 and 80-84; or
any one of SEQ ID NOs: 2 and 75-79; or
any one of SEQ ID NOs: 4 and 86-90; or
any one of SEQ ID NOs: 5 and 91-95; or
any one of SEQ ID NOs: 6 and 96-100; or
has at least 90% sequence identity to any one of the aforementioned sequences.

4. The PVRIG binding protein according to claim 1, further comprising a human immunoglobulin Fc region, wherein the Fc region is an Fc region of human IgG1 or IgG4.

5. A PVRIG/TIGIT binding protein, comprising a first antigen-binding domain specifically binding to PVRIG and a second antigen-binding domain specifically binding to T Cell Immunoreceptor with Ig and ITIM Domains (TIGIT), wherein the first antigen-binding domain comprises the PVRIG binding protein according to claim 1.

6. The PVRIG/TIGIT binding protein according to claim 5, wherein the immunoglobulin single variable domain in the first antigen-binding domain comprises the amino acid sequence of:

any one of SEQ ID NOs: 3 and 80-84; or
any one of SEQ ID NOs: 2 and 75-79; or
any one of SEQ ID NOs: 4 and 86-90; or
any one of SEQ ID NOs: 5 and 91-95; or
any one of SEQ ID NOs: 6 and 96-100; or
has at least 90% sequence identity to any one of the aforementioned sequences.

7. The PVRIG/TIGIT binding protein according to claim 5, wherein the second antigen-binding domain specifically binding to TIGIT comprises a heavy chain variable region (VH) and a light chain variable region (VL), wherein:

the heavy chain variable region comprises an HCDR1, an HCDR2 and an HCDR3 comprising the amino acid sequences of SEQ ID NOs: 121, 122 and 123, respectively, and the light chain variable region comprises an LCDR1, an LCDR2 and an LCDR3 comprising the amino acid sequences of SEQ ID NOs: 124, 125 and 126, respectively; or the heavy chain variable region comprises an HCDR1, an HCDR2 and an HCDR3 comprising the amino acid sequences of SEQ ID NOs: 115, 116 and 117, respectively, and the light chain variable region comprises an LCDR1, an LCDR2 and an LCDR3 comprising the amino acid sequences of SEQ ID NOs: 118, 119 and 120, respectively; or the heavy chain variable region comprises an HCDR1, an HCDR2 and an HCDR3 comprising the amino acid sequences of SEQ ID NOs: 127, 128 and 129, respectively, and the light chain variable region comprises an LCDR1, an LCDR2 and an LCDR3 comprising the amino acid sequences of SEQ ID NOs: 130, 131 and 132, respectively; or the heavy chain variable region comprises an HCDR1, an HCDR2 and an HCDR3 comprising the amino acid sequences of SEQ ID NOs: 133, 134 and 135, respectively, and the light chain variable region comprises an LCDR1, an LCDR2 and an LCDR3 comprising the amino acid sequences of SEQ ID NOs: 136, 137 and 138, respectively; or the heavy chain variable region comprises an HCDR1, an HCDR2 and an HCDR3 comprising the amino acid sequences of SEQ ID NOs: 139, 140 and 141, respectively, and the light chain variable region comprises an LCDR1, an LCDR2 and an LCDR3 comprising the amino acid sequences of SEQ ID NOs: 142, 143 and 144, respectively.

8. The PVRIG/TIGIT binding protein according to claim 7, wherein the heavy chain variable region of the second antigen-binding domain specifically binding to TIGIT comprises the amino acid sequence of any one of SEQ ID NOs: 145-147 or an amino acid sequence having at least 90% sequence identity thereto, and the light chain variable region comprises the amino acid sequence of any one of SEQ ID NOs: 148-149 or an amino acid sequence having at least 90%-sequence identity thereto.

9. The PVRIG/TIGIT binding protein according to claim 8, wherein the second antigen-binding domain specifically binding to TIGIT comprises a heavy chain comprising an amino acid sequence at least 90% identical to the amino acid sequence of SEQ ID NO: 102; and a light chain comprising an amino acid sequence at least 90% identical to the amino acid sequence of SEQ ID NO: 103.

10. The PVRIG/TIGIT binding protein according to claim 7 wherein:

the immunoglobulin single variable domain of the first antigen-binding domain specifically binding to PVRIG is located at N-terminal of the heavy chain variable region of the second antigen-binding domain specifically binding to TIGIT;

the immunoglobulin single variable domain of the first antigen-binding domain specifically binding to PVRIG is located at C-terminal of the heavy chain variable region of the second antigen-binding domain specifically binding to TIGIT;

the immunoglobulin single variable domain of the first antigen-binding domain specifically binding to PVRIG is located at N-terminal of the light chain variable region of the second antigen-binding domain specifically binding to TIGIT; or the immunoglobulin single variable domain of the first antigen-binding domain specifically binding to PVRIG is located at C-terminal of the light chain variable region of the second antigen-binding domain specifically binding to TIGIT.

11. The PVRIG/TIGIT binding protein according to claim 10, wherein the immunoglobulin single variable domain of the first antigen-binding domain is linked, directly or via a linker, to the second antigen-binding domain.

12. The PVRIG/TIGIT binding protein according to claim 5, comprising a first polypeptide chain and a second polypeptide chain, wherein:

the first polypeptide chain comprises the amino acid sequence of any one of SEQ ID NOs: 108-112 and 114, and the second polypeptide chain comprises the amino acid sequence of SEQ ID NO: 103; or the first polypeptide chain comprises the amino acid sequence of SEQ ID NO: 104 or 105, and the second polypeptide chain comprises the amino acid sequence of SEQ ID NO: 103; or the first polypeptide chain comprises the amino acid sequence of SEQ ID NO: 102, and the second polypeptide chain comprises the amino acid sequence of SEQ ID NO: 106 or 107.

13. An anti-PVRIG antibody or an antigen-binding fragment thereof, comprising the immunoglobulin single variable domain according to claim 1.

14. A polynucleotide encoding the PVRIG binding protein according to claim 1.

15. A host cell comprising the polynucleotide according to claim 14.

16. A method for preparing a PVRIG binding protein-comprising expressing the polynucleotide according to claim 14 in a host cell and isolating the expressed PVRIG binding protein from the host cell.

17. A pharmaceutical composition comprising the PVRIG binding protein according to claim 1, and a pharmaceutically acceptable excipient, diluent or carrier.

18. A method for treating a cancer or delaying progression of the cancer, comprising administering to a subject in need thereof, an effective amount of the PVRIG binding protein according to claim 1, wherein the amount is effective to treat or delay the cancer.

19. A method for activating NK cells, γδT cells or Th1 cells, comprising administering to a subject in need thereof, an effective amount of the PVRIG binding protein according claim 1.

20. A method for increasing generation of interferon-γ or secretion of pro-inflammatory cytokine, comprising administering to a subject in need thereof, an effective amount of the PVRIG binding protein according to claim 1.

21. The PVRIG binding protein according to claim 1, wherein the CDR1, CDR2, and CDR3 of the immunoglobulin single variable domain comprise the amino acid sequences of:

SEQ ID NOs: 10, 11 and 12 or 151, respectively;
SEQ ID NOs: 7, 8 and 9 or 150, respectively;
SEQ ID NOs: 13, 14 and 15, respectively;
SEQ ID NOs: 16, 17 and 18, respectively; or
SEQ ID NOs: 19, 20 and 21, respectively.

22. The PVRIG/TIGIT binding protein according to claim 5, wherein the CDR1, CDR2, and CDR3 of the immunoglobulin single variable domain specifically binding to PVRIG comprise the amino acid sequences of:

SEQ ID NOs: 10, 11 and 12 or 151, respectively;
SEQ ID NOs: 7, 8 and 9 or 150, respectively;
SEQ ID NOs: 13, 14 and 15, respectively;
SEQ ID NOs: 16, 17 and 18, respectively; or
SEQ ID NOs: 19, 20 and 21, respectively.

* * * * *

SEQUENCE LISTING

<160> NUMBER OF SEQ ID NOS: 168

<210> SEQ ID NO 1
<211> LENGTH: 137
<212> TYPE: PRT
<213> ORGANISM: Artificial sequence
<220> FEATURE:
<223> OTHER INFORMATION: his1PVRIG (cyno-PVRIG-his)

<400> SEQUENCE: 1

```
Thr Pro Glu Val Trp Val Gln Val Gln Met Glu Ala Thr Glu Leu Ser
1               5                   10                  15

Ser Phe Thr Val His Cys Gly Phe Leu Gly Pro Gly Ser Ile Ser Leu
            20                  25                  30

Val Thr Val Ser Trp Gly Gly Pro Asp Gly Ala Gly Gly Thr Lys Leu
        35                  40                  45

Ala Val Leu His Pro Glu Leu Gly Thr Arg Gln Trp Ala Pro Ala Arg
    50                  55                  60

Gln Ala Arg Trp Glu Thr Gln Ser Ser Ile Ser Leu Ala Leu Glu Asp
65                  70                  75                  80

Ser Gly Ala Ser Ser Pro Phe Ala Asn Thr Thr Phe Cys Cys Lys Phe
                85                  90                  95

Ala Ser Phe Pro Glu Gly Ser Trp Glu Ser Cys Gly Ser Leu Pro Pro
            100                 105                 110

Ser Ser Asp Pro Gly Leu Ser Ala Pro Pro Thr Pro Val Pro Ile Leu
        115                 120                 125

Arg Ala Asp His His His His His His
    130                 135
```

<210> SEQ ID NO 2
<211> LENGTH: 121
<212> TYPE: PRT
<213> ORGANISM: Artificial sequence
<220> FEATURE:
<223> OTHER INFORMATION: 20-HCVR

<400> SEQUENCE: 2

```
Asp Val Gln Leu Val Glu Ser Gly Gly Gly Ser Val Gln Ala Gly Gly
1               5                   10                  15

Ser Leu Arg Leu Ser Cys Val Ala Ser Arg Tyr Thr Ser Arg Thr Asp
            20                  25                  30

Cys Met Gly Trp Phe Arg Gln Ala Pro Gly Lys Glu His Glu Gly Val
            35                  40                  45

Ala His Ile Asp Ser Asp Gly Ile Pro Arg Tyr Val Asp Ser Val Lys
    50                  55                  60
```

```
Gly Arg Phe Thr Ile Ser Gln Asp His Ala Lys Asn Thr Leu Tyr Leu
65                  70                  75                  80

Gln Met Asn Ser Leu Lys Pro Glu Asp Ser Ala Thr Tyr Tyr Cys Val
                    85                  90                  95

Val Gly Phe Lys Phe Asp Asp Asp Tyr Cys Ala Pro Asn Asp Trp Gly
                100                 105                 110

Gln Gly Thr Gln Val Thr Val Ser Ser
            115                 120

<210> SEQ ID NO 3
<211> LENGTH: 121
<212> TYPE: PRT
<213> ORGANISM: Artificial sequence
<220> FEATURE:
<223> OTHER INFORMATION: 30-HCVR

<400> SEQUENCE: 3

His Val Gln Leu Val Glu Ser Gly Gly Gly Ser Val Gln Ala Gly Gly
1               5                   10                  15

Ser Leu Arg Leu Ser Cys Glu Ala Ser Gly Tyr Ser Tyr Ser Gly Asp
                20                  25                  30

Cys Met Gly Trp Phe Arg Arg Ala Pro Gly Lys Glu Arg Asp Glu Gly
            35                  40                  45

Val Ala Thr Ile Asp Asn Ala Gly Arg Ile Lys Tyr Ala Asp Ser Val
        50                  55                  60

Lys Gly Arg Phe Thr Ile Ser His Gly Asn Gly Lys Tyr Ile Leu Tyr
65                  70                  75                  80

Leu Gln Met Asn Ser Leu Lys Pro Glu Asp Thr Asp Met Tyr Tyr Cys
                    85                  90                  95

Ala Ala Gly Trp Thr Phe Gly Gly Asn Cys Ser Pro Ala Asp Trp Gly
                100                 105                 110

Gln Gly Thr Gln Val Thr Val Ser Ser
            115                 120

<210> SEQ ID NO 4
<211> LENGTH: 123
<212> TYPE: PRT
<213> ORGANISM: Artificial sequence
<220> FEATURE:
<223> OTHER INFORMATION: 38-HCVR

<400> SEQUENCE: 4

Gln Val Gln Leu Val Glu Ser Gly Gly Gly Ser Val Gln Ala Gly Gly
1               5                   10                  15

Ser Leu Arg Leu Ser Cys Ala Ala Ser Pro Ser Thr Tyr Gly Pro Ser
                20                  25                  30

Asp Met Ala Trp Phe Arg Gln Ala Pro Gly Lys Gln Arg Glu Gly Val
            35                  40                  45

Ala Thr Ile Ser Ala Ala Gly Arg Leu Thr Tyr Tyr Thr Asp Ser Val
        50                  55                  60

Arg Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Met Tyr Tyr Cys
                    85                  90                  95

Ala Ala Asp Phe Ala Gly Gly Ser Ser Leu Phe Ala Asp Tyr Lys Tyr
                100                 105                 110

Trp Gly Gln Gly Thr Gln Val Thr Val Ser Ser
```

-continued
```
            115                 120

<210> SEQ ID NO 5
<211> LENGTH: 120
<212> TYPE: PRT
<213> ORGANISM: Artificial sequence
<220> FEATURE:
<223> OTHER INFORMATION: 39-HCVR

<400> SEQUENCE: 5

Gln Val Gln Leu Val Glu Ser Gly Gly Gly Ser Val Gln Ala Gly Gly
1               5                   10                  15

Ser Leu Arg Leu Ser Cys Ala Ala Ser Arg Tyr Thr Ser Arg Thr Asp
            20                  25                  30

Cys Met Gly Trp Phe Arg Gln Ala Pro Gly Lys Glu Arg Glu Gly Val
        35                  40                  45

Ala His Ile Asp Ser Asp Gly Ile Pro Arg Tyr Val Glu Ser Val Lys
    50                  55                  60

Gly Arg Phe Thr Ile Ser Gln Asp His Ala Lys Asn Thr Leu Tyr Leu
65                  70                  75                  80

Gln Met Asn Ser Leu Lys Pro Glu Asp Ser Ala Thr Tyr Tyr Cys Val
                85                  90                  95

Val Gly Phe Lys Phe Gly Asp Tyr Cys Ala Pro Asn Asp Trp Gly Gln
            100                 105                 110

Gly Thr Gln Val Thr Val Ser Ser
        115                 120

<210> SEQ ID NO 6
<211> LENGTH: 127
<212> TYPE: PRT
<213> ORGANISM: Artificial sequence
<220> FEATURE:
<223> OTHER INFORMATION: 151-HCVR

<400> SEQUENCE: 6

His Val Gln Leu Val Glu Ser Gly Gly Gly Ser Val Gln Ala Gly Gly
1               5                   10                  15

Ser Leu Arg Leu Ser Cys Val Ala Ser Ala Ser Gly Phe Thr Tyr Arg
            20                  25                  30

Pro Tyr Cys Met Ala Trp Phe Arg Gln Ala Pro Gly Lys Glu Arg Glu
        35                  40                  45

Ala Val Ala Gly Ile Asp Ile Phe Gly Gly Thr Thr Tyr Ala Asp Ser
    50                  55                  60

Val Lys Gly Arg Phe Thr Ala Ser Arg Asp Asn Ala Gly Phe Ser Leu
65                  70                  75                  80

Phe Leu Gln Met Asn Asp Leu Lys Pro Glu Asp Thr Ala Met Tyr Tyr
                85                  90                  95

Cys Ala Ala Gly Asp Ser Pro Asp Gly Arg Cys Pro Pro Leu Gly Gln
            100                 105                 110

Gly Leu Asn Tyr Trp Gly Gln Gly Thr Gln Val Thr Val Ser Ser
        115                 120                 125

<210> SEQ ID NO 7
<211> LENGTH: 5
<212> TYPE: PRT
<213> ORGANISM: Artificial sequence
<220> FEATURE:
<223> OTHER INFORMATION: 20 HCDR1

<400> SEQUENCE: 7
```

```
Thr Asp Cys Met Gly
1               5

<210> SEQ ID NO 8
<211> LENGTH: 16
<212> TYPE: PRT
<213> ORGANISM: Artificial sequence
<220> FEATURE:
<223> OTHER INFORMATION: 20 HCDR2

<400> SEQUENCE: 8

His Ile Asp Ser Asp Gly Ile Pro Arg Tyr Val Asp Ser Val Lys Gly
1               5                   10                  15

<210> SEQ ID NO 9
<211> LENGTH: 13
<212> TYPE: PRT
<213> ORGANISM: Artificial sequence
<220> FEATURE:
<223> OTHER INFORMATION: 20 HCDR3

<400> SEQUENCE: 9

Gly Phe Lys Phe Asp Asp Asp Tyr Cys Ala Pro Asn Asp
1               5                   10

<210> SEQ ID NO 10
<211> LENGTH: 5
<212> TYPE: PRT
<213> ORGANISM: Artificial sequence
<220> FEATURE:
<223> OTHER INFORMATION: 30 HCDR1

<400> SEQUENCE: 10

Gly Asp Cys Met Gly
1               5

<210> SEQ ID NO 11
<211> LENGTH: 16
<212> TYPE: PRT
<213> ORGANISM: Artificial sequence
<220> FEATURE:
<223> OTHER INFORMATION: 30 HCDR2

<400> SEQUENCE: 11

Thr Ile Asp Asn Ala Gly Arg Ile Lys Tyr Ala Asp Ser Val Lys Gly
1               5                   10                  15

<210> SEQ ID NO 12
<211> LENGTH: 12
<212> TYPE: PRT
<213> ORGANISM: Artificial sequence
<220> FEATURE:
<223> OTHER INFORMATION: 30 HCDR3

<400> SEQUENCE: 12

Gly Trp Thr Phe Gly Gly Asn Cys Ser Pro Ala Asp
1               5                   10

<210> SEQ ID NO 13
<211> LENGTH: 5
<212> TYPE: PRT
<213> ORGANISM: Artificial sequence
<220> FEATURE:
<223> OTHER INFORMATION: 38 HCDR1

<400> SEQUENCE: 13
```

-continued

```
Pro Ser Asp Met Ala
1               5

<210> SEQ ID NO 14
<211> LENGTH: 17
<212> TYPE: PRT
<213> ORGANISM: Artificial sequence
<220> FEATURE:
<223> OTHER INFORMATION: 38 HCDR2

<400> SEQUENCE: 14

Thr Ile Ser Ala Ala Gly Arg Leu Thr Tyr Tyr Thr Asp Ser Val Arg
1               5                   10                  15

Gly

<210> SEQ ID NO 15
<211> LENGTH: 14
<212> TYPE: PRT
<213> ORGANISM: Artificial sequence
<220> FEATURE:
<223> OTHER INFORMATION: 38 HCDR3

<400> SEQUENCE: 15

Asp Phe Ala Gly Gly Ser Ser Leu Phe Ala Asp Tyr Lys Tyr
1               5                   10

<210> SEQ ID NO 16
<211> LENGTH: 5
<212> TYPE: PRT
<213> ORGANISM: Artificial sequence
<220> FEATURE:
<223> OTHER INFORMATION: 39 HCDR1

<400> SEQUENCE: 16

Thr Asp Cys Met Gly
1               5

<210> SEQ ID NO 17
<211> LENGTH: 16
<212> TYPE: PRT
<213> ORGANISM: Artificial sequence
<220> FEATURE:
<223> OTHER INFORMATION: 39 HCDR2

<400> SEQUENCE: 17

His Ile Asp Ser Asp Gly Ile Pro Arg Tyr Val Glu Ser Val Lys Gly
1               5                   10                  15

<210> SEQ ID NO 18
<211> LENGTH: 12
<212> TYPE: PRT
<213> ORGANISM: Artificial sequence
<220> FEATURE:
<223> OTHER INFORMATION: 39 HCDR3

<400> SEQUENCE: 18

Gly Phe Lys Phe Gly Asp Tyr Cys Ala Pro Asn Asp
1               5                   10

<210> SEQ ID NO 19
<211> LENGTH: 7
<212> TYPE: PRT
<213> ORGANISM: Artificial sequence
<220> FEATURE:
<223> OTHER INFORMATION: 151 HCDR1

<400> SEQUENCE: 19
```

Tyr Arg Pro Tyr Cys Met Ala
1               5

<210> SEQ ID NO 20
<211> LENGTH: 16
<212> TYPE: PRT
<213> ORGANISM: Artificial sequence
<220> FEATURE:
<223> OTHER INFORMATION: 151 HCDR2

<400> SEQUENCE: 20

Gly Ile Asp Ile Phe Gly Gly Thr Thr Tyr Ala Asp Ser Val Lys Gly
1               5                   10                  15

<210> SEQ ID NO 21
<211> LENGTH: 17
<212> TYPE: PRT
<213> ORGANISM: Artificial sequence
<220> FEATURE:
<223> OTHER INFORMATION: 151 HCDR3

<400> SEQUENCE: 21

Gly Asp Ser Pro Asp Gly Arg Cys Pro Pro Leu Gly Gln Gly Leu Asn
1               5                   10                  15

Tyr

<210> SEQ ID NO 22
<211> LENGTH: 7
<212> TYPE: PRT
<213> ORGANISM: Artificial sequence
<220> FEATURE:
<223> OTHER INFORMATION: 20 HCDR1 CHO

<400> SEQUENCE: 22

Arg Tyr Thr Ser Arg Thr Asp
1               5

<210> SEQ ID NO 23
<211> LENGTH: 5
<212> TYPE: PRT
<213> ORGANISM: Artificial sequence
<220> FEATURE:
<223> OTHER INFORMATION: 20 HCDR2 CHO

<400> SEQUENCE: 23

Asp Ser Asp Gly Ile
1               5

<210> SEQ ID NO 24
<211> LENGTH: 13
<212> TYPE: PRT
<213> ORGANISM: Artificial sequence
<220> FEATURE:
<223> OTHER INFORMATION: 20 HCDR3 CHO

<400> SEQUENCE: 24

Gly Phe Lys Phe Asp Asp Asp Tyr Cys Ala Pro Asn Asp
1               5                   10

<210> SEQ ID NO 25
<211> LENGTH: 7
<212> TYPE: PRT
<213> ORGANISM: Artificial sequence
<220> FEATURE:
<223> OTHER INFORMATION: 30 HCDR1 CHO

```
<400> SEQUENCE: 25

Gly Tyr Ser Tyr Ser Gly Asp
1               5

<210> SEQ ID NO 26
<211> LENGTH: 5
<212> TYPE: PRT
<213> ORGANISM: Artificial sequence
<220> FEATURE:
<223> OTHER INFORMATION: 30 HCDR2 CHO

<400> SEQUENCE: 26

Asp Asn Ala Gly Arg
1               5

<210> SEQ ID NO 27
<211> LENGTH: 12
<212> TYPE: PRT
<213> ORGANISM: Artificial sequence
<220> FEATURE:
<223> OTHER INFORMATION: 30 HCDR3 CHO

<400> SEQUENCE: 27

Gly Trp Thr Phe Gly Gly Asn Cys Ser Pro Ala Asp
1               5                   10

<210> SEQ ID NO 28
<211> LENGTH: 7
<212> TYPE: PRT
<213> ORGANISM: Artificial sequence
<220> FEATURE:
<223> OTHER INFORMATION: 38 HCDR1 CHO

<400> SEQUENCE: 28

Pro Ser Thr Tyr Gly Pro Ser
1               5

<210> SEQ ID NO 29
<211> LENGTH: 6
<212> TYPE: PRT
<213> ORGANISM: Artificial sequence
<220> FEATURE:
<223> OTHER INFORMATION: 38 HCDR2 CHO

<400> SEQUENCE: 29

Ser Ala Ala Gly Arg Leu
1               5

<210> SEQ ID NO 30
<211> LENGTH: 14
<212> TYPE: PRT
<213> ORGANISM: Artificial sequence
<220> FEATURE:
<223> OTHER INFORMATION: 38 HCDR3 CHO

<400> SEQUENCE: 30

Asp Phe Ala Gly Gly Ser Ser Leu Phe Ala Asp Tyr Lys Tyr
1               5                   10

<210> SEQ ID NO 31
<211> LENGTH: 7
<212> TYPE: PRT
<213> ORGANISM: Artificial sequence
<220> FEATURE:
<223> OTHER INFORMATION: 39 HCDR1 CHO

<400> SEQUENCE: 31
```

```
Arg Tyr Thr Ser Arg Thr Asp
1               5

<210> SEQ ID NO 32
<211> LENGTH: 5
<212> TYPE: PRT
<213> ORGANISM: Artificial sequence
<220> FEATURE:
<223> OTHER INFORMATION: 39 HCDR2 CHO

<400> SEQUENCE: 32

Asp Ser Asp Gly Ile
1               5

<210> SEQ ID NO 33
<211> LENGTH: 12
<212> TYPE: PRT
<213> ORGANISM: Artificial sequence
<220> FEATURE:
<223> OTHER INFORMATION: 39 HCDR3 CHO

<400> SEQUENCE: 33

Gly Phe Lys Phe Gly Asp Tyr Cys Ala Pro Asn Asp
1               5                   10

<210> SEQ ID NO 34
<211> LENGTH: 9
<212> TYPE: PRT
<213> ORGANISM: Artificial sequence
<220> FEATURE:
<223> OTHER INFORMATION: 151 HCDR1 CHO

<400> SEQUENCE: 34

Ala Ser Gly Phe Thr Tyr Arg Pro Tyr
1               5

<210> SEQ ID NO 35
<211> LENGTH: 5
<212> TYPE: PRT
<213> ORGANISM: Artificial sequence
<220> FEATURE:
<223> OTHER INFORMATION: 151 HCDR2 CHO

<400> SEQUENCE: 35

Asp Ile Phe Gly Gly
1               5

<210> SEQ ID NO 36
<211> LENGTH: 17
<212> TYPE: PRT
<213> ORGANISM: Artificial sequence
<220> FEATURE:
<223> OTHER INFORMATION: 151 HCDR3 CHO

<400> SEQUENCE: 36

Gly Asp Ser Pro Asp Gly Arg Cys Pro Pro Leu Gly Gln Gly Leu Asn
1               5                   10                  15

Tyr

<210> SEQ ID NO 37
<211> LENGTH: 8
<212> TYPE: PRT
<213> ORGANISM: Artificial sequence
<220> FEATURE:
<223> OTHER INFORMATION: 20 HCDR1 IMGT
```

```
<400> SEQUENCE: 37

Arg Tyr Thr Ser Arg Thr Asp Cys
1               5

<210> SEQ ID NO 38
<211> LENGTH: 7
<212> TYPE: PRT
<213> ORGANISM: Artificial sequence
<220> FEATURE:
<223> OTHER INFORMATION: 20 HCDR2 IMGT

<400> SEQUENCE: 38

Ile Asp Ser Asp Gly Ile Pro
1               5

<210> SEQ ID NO 39
<211> LENGTH: 15
<212> TYPE: PRT
<213> ORGANISM: Artificial sequence
<220> FEATURE:
<223> OTHER INFORMATION: 20 HCDR3 IMGT

<400> SEQUENCE: 39

Val Val Gly Phe Lys Phe Asp Asp Asp Tyr Cys Ala Pro Asn Asp
1               5                   10                  15

<210> SEQ ID NO 40
<211> LENGTH: 8
<212> TYPE: PRT
<213> ORGANISM: Artificial sequence
<220> FEATURE:
<223> OTHER INFORMATION: 30 HCDR1 IMGT

<400> SEQUENCE: 40

Gly Tyr Ser Tyr Ser Gly Asp Cys
1               5

<210> SEQ ID NO 41
<211> LENGTH: 7
<212> TYPE: PRT
<213> ORGANISM: Artificial sequence
<220> FEATURE:
<223> OTHER INFORMATION: 30 HCDR2 IMGT

<400> SEQUENCE: 41

Ile Asp Asn Ala Gly Arg Ile
1               5

<210> SEQ ID NO 42
<211> LENGTH: 14
<212> TYPE: PRT
<213> ORGANISM: Artificial sequence
<220> FEATURE:
<223> OTHER INFORMATION: 30 HCDR3 IMGT

<400> SEQUENCE: 42

Ala Ala Gly Trp Thr Phe Gly Gly Asn Cys Ser Pro Ala Asp
1               5                   10

<210> SEQ ID NO 43
<211> LENGTH: 8
<212> TYPE: PRT
<213> ORGANISM: Artificial sequence
<220> FEATURE:
<223> OTHER INFORMATION: 38 HCDR1 IMGT

<400> SEQUENCE: 43
```

```
Pro Ser Thr Tyr Gly Pro Ser Asp
1               5

<210> SEQ ID NO 44
<211> LENGTH: 8
<212> TYPE: PRT
<213> ORGANISM: Artificial sequence
<220> FEATURE:
<223> OTHER INFORMATION: 38 HCDR2 IMGT

<400> SEQUENCE: 44

Ile Ser Ala Ala Gly Arg Leu Thr
1               5

<210> SEQ ID NO 45
<211> LENGTH: 16
<212> TYPE: PRT
<213> ORGANISM: Artificial sequence
<220> FEATURE:
<223> OTHER INFORMATION: 38 HCDR3 IMGT

<400> SEQUENCE: 45

Ala Ala Asp Phe Ala Gly Gly Ser Ser Leu Phe Ala Asp Tyr Lys Tyr
1               5                   10                  15

<210> SEQ ID NO 46
<211> LENGTH: 8
<212> TYPE: PRT
<213> ORGANISM: Artificial sequence
<220> FEATURE:
<223> OTHER INFORMATION: 39 HCDR1 IMGT

<400> SEQUENCE: 46

Arg Tyr Thr Ser Arg Thr Asp Cys
1               5

<210> SEQ ID NO 47
<211> LENGTH: 7
<212> TYPE: PRT
<213> ORGANISM: Artificial sequence
<220> FEATURE:
<223> OTHER INFORMATION: 39 HCDR2 IMGT

<400> SEQUENCE: 47

Ile Asp Ser Asp Gly Ile Pro
1               5

<210> SEQ ID NO 48
<211> LENGTH: 14
<212> TYPE: PRT
<213> ORGANISM: Artificial sequence
<220> FEATURE:
<223> OTHER INFORMATION: 39 HCDR3 IMGT

<400> SEQUENCE: 48

Val Val Gly Phe Lys Phe Gly Asp Tyr Cys Ala Pro Asn Asp
1               5                   10

<210> SEQ ID NO 49
<211> LENGTH: 10
<212> TYPE: PRT
<213> ORGANISM: Artificial sequence
<220> FEATURE:
<223> OTHER INFORMATION: 151 HCDR1 IMGT

<400> SEQUENCE: 49
```

-continued

```
Ala Ser Gly Phe Thr Tyr Arg Pro Tyr Cys
1               5                   10

<210> SEQ ID NO 50
<211> LENGTH: 7
<212> TYPE: PRT
<213> ORGANISM: Artificial sequence
<220> FEATURE:
<223> OTHER INFORMATION: 151 HCDR2 IMGT

<400> SEQUENCE: 50

Ile Asp Ile Phe Gly Gly Thr
1               5

<210> SEQ ID NO 51
<211> LENGTH: 19
<212> TYPE: PRT
<213> ORGANISM: Artificial sequence
<220> FEATURE:
<223> OTHER INFORMATION: 151 HCDR3 IMGT

<400> SEQUENCE: 51

Ala Ala Gly Asp Ser Pro Asp Gly Arg Cys Pro Pro Leu Gly Gln Gly
1               5                   10                  15

Leu Asn Tyr

<210> SEQ ID NO 52
<211> LENGTH: 10
<212> TYPE: PRT
<213> ORGANISM: Artificial sequence
<220> FEATURE:
<223> OTHER INFORMATION: 20 HCDR1 ABM

<400> SEQUENCE: 52

Arg Tyr Thr Ser Arg Thr Asp Cys Met Gly
1               5                   10

<210> SEQ ID NO 53
<211> LENGTH: 9
<212> TYPE: PRT
<213> ORGANISM: Artificial sequence
<220> FEATURE:
<223> OTHER INFORMATION: 20 HCDR2 ABM

<400> SEQUENCE: 53

His Ile Asp Ser Asp Gly Ile Pro Arg
1               5

<210> SEQ ID NO 54
<211> LENGTH: 13
<212> TYPE: PRT
<213> ORGANISM: Artificial sequence
<220> FEATURE:
<223> OTHER INFORMATION: 20 HCDR3 ABM

<400> SEQUENCE: 54

Gly Phe Lys Phe Asp Asp Asp Tyr Cys Ala Pro Asn Asp
1               5                   10

<210> SEQ ID NO 55
<211> LENGTH: 10
<212> TYPE: PRT
<213> ORGANISM: Artificial sequence
<220> FEATURE:
<223> OTHER INFORMATION: 30 HCDR1 ABM

<400> SEQUENCE: 55
```

-continued

Gly Tyr Ser Tyr Ser Gly Asp Cys Met Gly
1               5                   10

<210> SEQ ID NO 56
<211> LENGTH: 9
<212> TYPE: PRT
<213> ORGANISM: Artificial sequence
<220> FEATURE:
<223> OTHER INFORMATION: 30 HCDR2 ABM

<400> SEQUENCE: 56

Thr Ile Asp Asn Ala Gly Arg Ile Lys
1               5

<210> SEQ ID NO 57
<211> LENGTH: 12
<212> TYPE: PRT
<213> ORGANISM: Artificial sequence
<220> FEATURE:
<223> OTHER INFORMATION: 30 HCDR3 ABM

<400> SEQUENCE: 57

Gly Trp Thr Phe Gly Gly Asn Cys Ser Pro Ala Asp
1               5                   10

<210> SEQ ID NO 58
<211> LENGTH: 10
<212> TYPE: PRT
<213> ORGANISM: Artificial sequence
<220> FEATURE:
<223> OTHER INFORMATION: 38 HCDR1 ABM

<400> SEQUENCE: 58

Pro Ser Thr Tyr Gly Pro Ser Asp Met Ala
1               5                   10

<210> SEQ ID NO 59
<211> LENGTH: 10
<212> TYPE: PRT
<213> ORGANISM: Artificial sequence
<220> FEATURE:
<223> OTHER INFORMATION: 38 HCDR2 ABM

<400> SEQUENCE: 59

Thr Ile Ser Ala Ala Gly Arg Leu Thr Tyr
1               5                   10

<210> SEQ ID NO 60
<211> LENGTH: 14
<212> TYPE: PRT
<213> ORGANISM: Artificial sequence
<220> FEATURE:
<223> OTHER INFORMATION: 38 HCDR3 ABM

<400> SEQUENCE: 60

Asp Phe Ala Gly Gly Ser Ser Leu Phe Ala Asp Tyr Lys Tyr
1               5                   10

<210> SEQ ID NO 61
<211> LENGTH: 10
<212> TYPE: PRT
<213> ORGANISM: Artificial sequence
<220> FEATURE:
<223> OTHER INFORMATION: 39 HCDR1 ABM

<400> SEQUENCE: 61

```
Arg Tyr Thr Ser Arg Thr Asp Cys Met Gly
1               5               10

<210> SEQ ID NO 62
<211> LENGTH: 9
<212> TYPE: PRT
<213> ORGANISM: Artificial sequence
<220> FEATURE:
<223> OTHER INFORMATION: 39 HCDR2 ABM

<400> SEQUENCE: 62

His Ile Asp Ser Asp Gly Ile Pro Arg
1               5

<210> SEQ ID NO 63
<211> LENGTH: 12
<212> TYPE: PRT
<213> ORGANISM: Artificial sequence
<220> FEATURE:
<223> OTHER INFORMATION: 39 HCDR3 ABM

<400> SEQUENCE: 63

Gly Phe Lys Phe Gly Asp Tyr Cys Ala Pro Asn Asp
1               5               10

<210> SEQ ID NO 64
<211> LENGTH: 12
<212> TYPE: PRT
<213> ORGANISM: Artificial sequence
<220> FEATURE:
<223> OTHER INFORMATION: 151 HCDR1 ABM

<400> SEQUENCE: 64

Ala Ser Gly Phe Thr Tyr Arg Pro Tyr Cys Met Ala
1               5               10

<210> SEQ ID NO 65
<211> LENGTH: 9
<212> TYPE: PRT
<213> ORGANISM: Artificial sequence
<220> FEATURE:
<223> OTHER INFORMATION: 151 HCDR2 ABM

<400> SEQUENCE: 65

Gly Ile Asp Ile Phe Gly Gly Thr Thr
1               5

<210> SEQ ID NO 66
<211> LENGTH: 17
<212> TYPE: PRT
<213> ORGANISM: Artificial sequence
<220> FEATURE:
<223> OTHER INFORMATION: 151 HCDR3 ABM

<400> SEQUENCE: 66

Gly Asp Ser Pro Asp Gly Arg Cys Pro Pro Leu Gly Gln Gly Leu Asn
1               5               10                  15

Tyr

<210> SEQ ID NO 67
<211> LENGTH: 350
<212> TYPE: PRT
<213> ORGANISM: Artificial sequence
<220> FEATURE:
<223> OTHER INFORMATION: 20 HC

<400> SEQUENCE: 67
```

-continued

Asp Val Gln Leu Val Glu Ser Gly Gly Gly Ser Val Gln Ala Gly Gly
1               5               10              15

Ser Leu Arg Leu Ser Cys Val Ala Ser Arg Tyr Thr Ser Arg Thr Asp
            20              25              30

Cys Met Gly Trp Phe Arg Gln Ala Pro Gly Lys Glu His Glu Gly Val
        35              40              45

Ala His Ile Asp Ser Asp Gly Ile Pro Arg Tyr Val Asp Ser Val Lys
    50              55              60

Gly Arg Phe Thr Ile Ser Gln Asp His Ala Lys Asn Thr Leu Tyr Leu
65              70              75              80

Gln Met Asn Ser Leu Lys Pro Glu Asp Ser Ala Thr Tyr Tyr Cys Val
            85              90              95

Val Gly Phe Lys Phe Asp Asp Asp Tyr Cys Ala Pro Asn Asp Trp Gly
        100             105             110

Gln Gly Thr Gln Val Thr Val Ser Ser Glu Ser Lys Tyr Gly Pro Pro
        115             120             125

Cys Pro Pro Cys Pro Ala Pro Glu Ala Ala Gly Gly Pro Ser Val Phe
    130             135             140

Leu Phe Pro Pro Lys Pro Lys Asp Thr Leu Met Ile Ser Arg Thr Pro
145             150             155             160

Glu Val Thr Cys Val Val Val Asp Val Ser Gln Glu Asp Pro Glu Val
        165             170             175

Gln Phe Asn Trp Tyr Val Asp Gly Val Glu Val His Asn Ala Lys Thr
        180             185             190

Lys Pro Arg Glu Glu Gln Phe Asn Ser Thr Tyr Arg Val Val Ser Val
        195             200             205

Leu Thr Val Leu His Gln Asp Trp Leu Asn Gly Lys Glu Tyr Lys Cys
    210             215             220

Lys Val Ser Asn Lys Gly Leu Pro Ser Ser Ile Glu Lys Thr Ile Ser
225             230             235             240

Lys Ala Lys Gly Gln Pro Arg Glu Pro Gln Val Tyr Thr Leu Pro Pro
        245             250             255

Ser Gln Glu Glu Met Thr Lys Asn Gln Val Ser Leu Thr Cys Leu Val
        260             265             270

Lys Gly Phe Tyr Pro Ser Asp Ile Ala Val Glu Trp Glu Ser Asn Gly
        275             280             285

Gln Pro Glu Asn Asn Tyr Lys Thr Thr Pro Pro Val Leu Asp Ser Asp
        290             295             300

Gly Ser Phe Phe Leu Tyr Ser Arg Leu Thr Val Asp Lys Ser Arg Trp
305             310             315             320

Gln Glu Gly Asn Val Phe Ser Cys Ser Val Met His Glu Ala Leu His
        325             330             335

Asn His Tyr Thr Gln Lys Ser Leu Ser Leu Ser Leu Gly Ala
        340             345             350

<210> SEQ ID NO 68
<211> LENGTH: 350
<212> TYPE: PRT
<213> ORGANISM: Artificial sequence
<220> FEATURE:
<223> OTHER INFORMATION: 30 HC

<400> SEQUENCE: 68

His Val Gln Leu Val Glu Ser Gly Gly Gly Ser Val Gln Ala Gly Gly
1               5               10              15

-continued

```
Ser Leu Arg Leu Ser Cys Glu Ala Ser Gly Tyr Ser Tyr Ser Gly Asp
            20                  25                  30

Cys Met Gly Trp Phe Arg Arg Ala Pro Gly Lys Glu Arg Asp Glu Gly
            35                  40                  45

Val Ala Thr Ile Asp Asn Ala Gly Arg Ile Lys Tyr Ala Asp Ser Val
        50                  55                  60

Lys Gly Arg Phe Thr Ile Ser His Gly Asn Gly Lys Tyr Ile Leu Tyr
65                  70                  75                  80

Leu Gln Met Asn Ser Leu Lys Pro Glu Asp Thr Asp Met Tyr Tyr Cys
                85                  90                  95

Ala Ala Gly Trp Thr Phe Gly Gly Asn Cys Ser Pro Ala Asp Trp Gly
            100                 105                 110

Gln Gly Thr Gln Val Thr Val Ser Ser Glu Ser Lys Tyr Gly Pro Pro
            115                 120                 125

Cys Pro Pro Cys Pro Ala Pro Glu Ala Ala Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser Gln Glu Asp Pro Glu Val
            165                 170                 175

Gln Phe Asn Trp Tyr Val Asp Gly Val Glu Val His Asn Ala Lys Thr
            180                 185                 190

Lys Pro Arg Glu Glu Gln Phe Asn Ser Thr Tyr Arg Val Val Ser Val
            195                 200                 205

Leu Thr Val Leu His Gln Asp Trp Leu Asn Gly Lys Glu Tyr Lys Cys
    210                 215                 220

Lys Val Ser Asn Lys Gly Leu Pro Ser Ser Ile Glu Lys Thr Ile Ser
225                 230                 235                 240

Lys Ala Lys Gly Gln Pro Arg Glu Pro Gln Val Tyr Thr Leu Pro Pro
            245                 250                 255

Ser Gln Glu Glu Met Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
            275                 280                 285

Gln Pro Glu Asn Asn Tyr Lys Thr Thr Pro Pro Val Leu Asp Ser Asp
    290                 295                 300

Gly Ser Phe Phe Leu Tyr Ser Arg Leu Thr Val Asp Lys Ser Arg Trp
305                 310                 315                 320

Gln Glu Gly Asn Val Phe Ser Cys Ser Val Met His Glu Ala Leu His
            325                 330                 335

Asn His Tyr Thr Gln Lys Ser Leu Ser Leu Ser Leu Gly Ala
            340                 345                 350
```

```
<210> SEQ ID NO 69
<211> LENGTH: 352
<212> TYPE: PRT
<213> ORGANISM: Artificial sequence
<220> FEATURE:
<223> OTHER INFORMATION: 38 HC

<400> SEQUENCE: 69
```

```
Gln Val Gln Leu Val Glu Ser Gly Gly Gly Ser Val Gln Ala Gly Gly
1               5                   10                  15

Ser Leu Arg Leu Ser Cys Ala Ala Ser Pro Ser Thr Tyr Gly Pro Ser
            20                  25                  30
```

-continued

```
Asp Met Ala Trp Phe Arg Gln Ala Pro Gly Lys Gln Arg Glu Gly Val
        35                  40                  45

Ala Thr Ile Ser Ala Ala Gly Arg Leu Thr Tyr Tyr Thr Asp Ser Val
    50                  55                  60

Arg Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Met Tyr Tyr Cys
                85                  90                  95

Ala Ala Asp Phe Ala Gly Gly Ser Ser Leu Phe Ala Asp Tyr Lys Tyr
            100                 105                 110

Trp Gly Gln Gly Thr Gln Val Thr Val Ser Ser Glu Ser Lys Tyr Gly
        115                 120                 125

Pro Pro Cys Pro Pro Cys Pro Ala Pro Glu Ala Ala Gly Gly Pro Ser
        130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser Gln Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Gly Leu Pro Ser Ser Ile Glu Lys Thr
225                 230                 235                 240

Ile Ser Lys Ala Lys Gly Gln Pro Arg Glu Pro Gln Val Tyr Thr Leu
            245                 250                 255

Pro Pro Ser Gln Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Arg Leu Thr Val Asp Lys Ser
305                 310                 315                 320

Arg Trp Gln Glu Gly Asn Val Phe Ser Cys Ser Val Met His Glu Ala
            325                 330                 335

Leu His Asn His Tyr Thr Gln Lys Ser Leu Ser Leu Ser Leu Gly Ala
            340                 345                 350
```

```
<210> SEQ ID NO 70
<211> LENGTH: 349
<212> TYPE: PRT
<213> ORGANISM: Artificial sequence
<220> FEATURE:
<223> OTHER INFORMATION: 39 HC

<400> SEQUENCE: 70
```

```
Gln Val Gln Leu Val Glu Ser Gly Gly Gly Ser Val Gln Ala Gly Gly
1               5                   10                  15

Ser Leu Arg Leu Ser Cys Ala Ala Ser Arg Tyr Thr Ser Arg Thr Asp
            20                  25                  30

Cys Met Gly Trp Phe Arg Gln Ala Pro Gly Lys Glu Arg Glu Gly Val
        35                  40                  45
```

```
Ala His Ile Asp Ser Asp Gly Ile Pro Arg Tyr Val Glu Ser Val Lys
    50              55              60

Gly Arg Phe Thr Ile Ser Gln Asp His Ala Lys Asn Thr Leu Tyr Leu
65              70              75              80

Gln Met Asn Ser Leu Lys Pro Glu Asp Ser Ala Thr Tyr Tyr Cys Val
                85              90              95

Val Gly Phe Lys Phe Gly Asp Tyr Cys Ala Pro Asn Asp Trp Gly Gln
            100             105             110

Gly Thr Gln Val Thr Val Ser Ser Glu Ser Lys Tyr Gly Pro Pro Cys
            115             120             125

Pro Pro Cys Pro Ala Pro Glu Ala Ala Gly Gly Pro Ser Val Phe Leu
    130             135             140

Phe Pro Pro Lys Pro Lys Asp Thr Leu Met Ile Ser Arg Thr Pro Glu
145             150             155             160

Val Thr Cys Val Val Val Asp Val Ser Gln Glu Asp Pro Glu Val Gln
            165             170             175

Phe Asn Trp Tyr Val Asp Gly Val Glu Val His Asn Ala Lys Thr Lys
            180             185             190

Pro Arg Glu Glu Gln Phe Asn Ser Thr Tyr Arg Val Val Ser Val Leu
            195             200             205

Thr Val Leu His Gln Asp Trp Leu Asn Gly Lys Glu Tyr Lys Cys Lys
    210             215             220

Val Ser Asn Lys Gly Leu Pro Ser Ser Ile Glu Lys Thr Ile Ser Lys
225             230             235             240

Ala Lys Gly Gln Pro Arg Glu Pro Gln Val Tyr Thr Leu Pro Pro Ser
            245             250             255

Gln Glu Glu Met Thr Lys Asn Gln Val Ser Leu Thr Cys Leu Val Lys
            260             265             270

Gly Phe Tyr Pro Ser Asp Ile Ala Val Glu Trp Glu Ser Asn Gly Gln
            275             280             285

Pro Glu Asn Asn Tyr Lys Thr Thr Pro Pro Val Leu Asp Ser Asp Gly
    290             295             300

Ser Phe Phe Leu Tyr Ser Arg Leu Thr Val Asp Lys Ser Arg Trp Gln
305             310             315             320

Glu Gly Asn Val Phe Ser Cys Ser Val Met His Glu Ala Leu His Asn
            325             330             335

His Tyr Thr Gln Lys Ser Leu Ser Leu Ser Leu Gly Ala
            340             345
```

```
<210> SEQ ID NO 71
<211> LENGTH: 356
<212> TYPE: PRT
<213> ORGANISM: Artificial sequence
<220> FEATURE:
<223> OTHER INFORMATION: 151 HC

<400> SEQUENCE: 71
```

```
His Val Gln Leu Val Glu Ser Gly Gly Gly Ser Val Gln Ala Gly Gly
1               5               10              15

Ser Leu Arg Leu Ser Cys Val Ala Ser Ala Ser Gly Phe Thr Tyr Arg
            20              25              30

Pro Tyr Cys Met Ala Trp Phe Arg Gln Ala Pro Gly Lys Glu Arg Glu
        35              40              45

Ala Val Ala Gly Ile Asp Ile Phe Gly Gly Thr Thr Tyr Ala Asp Ser
    50              55              60
```

-continued

```
Val Lys Gly Arg Phe Thr Ala Ser Arg Asp Asn Ala Gly Phe Ser Leu
65                  70                  75                  80

Phe Leu Gln Met Asn Asp Leu Lys Pro Glu Asp Thr Ala Met Tyr Tyr
                85                  90                  95

Cys Ala Ala Gly Asp Ser Pro Asp Gly Arg Cys Pro Pro Leu Gly Gln
                100                 105                 110

Gly Leu Asn Tyr Trp Gly Gln Gly Thr Gln Val Thr Val Ser Ser Glu
                115                 120                 125

Ser Lys Tyr Gly Pro Pro Cys Pro Pro Cys Pro Ala Pro Glu Ala Ala
        130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

Gln Glu Asp Pro Glu Val Gln Phe Asn Trp Tyr Val Asp Gly Val Glu
                180                 185                 190

Val His Asn Ala Lys Thr Lys Pro Arg Glu Glu Gln Phe Asn Ser Thr
                195                 200                 205

Tyr Arg Val Val Ser Val Leu Thr Val Leu His Gln Asp Trp Leu Asn
        210                 215                 220

Gly Lys Glu Tyr Lys Cys Lys Val Ser Asn Lys Gly Leu Pro Ser Ser
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Gln Glu Glu Met Thr Lys Asn Gln Val
                260                 265                 270

Ser Leu Thr Cys Leu Val Lys Gly Phe Tyr Pro Ser Asp Ile Ala Val
                275                 280                 285

Glu Trp Glu Ser Asn Gly Gln Pro Glu Asn Asn Tyr Lys Thr Thr Pro
        290                 295                 300

Pro Val Leu Asp Ser Asp Gly Ser Phe Phe Leu Tyr Ser Arg Leu Thr
305                 310                 315                 320

Val Asp Lys Ser Arg Trp Gln Glu Gly Asn Val Phe Ser Cys Ser Val
                325                 330                 335

Met His Glu Ala Leu His Asn His Tyr Thr Gln Lys Ser Leu Ser Leu
                340                 345                 350

Ser Leu Gly Ala
        355
```

```
<210> SEQ ID NO 72
<211> LENGTH: 449
<212> TYPE: PRT
<213> ORGANISM: Artificial sequence
<220> FEATURE:
<223> OTHER INFORMATION: tab5 HC

<400> SEQUENCE: 72
```

```
Glu Val Gln Leu Val Glu Ser Gly Gly Gly Val Val Lys Pro Gly Gly
1               5                   10                  15

Ser Leu Arg Leu Ser Cys Ala Ala Ser Gly Phe Thr Phe Gly Thr Ser
                20                  25                  30

Ser Met Asn Trp Val Arg Gln Ala Pro Gly Lys Gly Leu Glu Trp Val
        35                  40                  45

Ala Val Ile Ser Phe Asp Gly Thr Glu Ile His Tyr Ala Asp Ser Val
        50                  55                  60
```

```
Lys Gly Arg Phe Thr Ile Ser Arg Asp Asn Ser Lys Ser Thr Val Phe
65                  70                  75                  80

Leu Gln Met Asn Ser Leu Arg Pro Asp Asp Thr Ala Leu Tyr Tyr Cys
                85                  90                  95

Ala Lys Gly Ser Gly Asn Ile Tyr Phe Tyr Ser Gly Met Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Ala
```

<210> SEQ ID NO 73
<211> LENGTH: 214
<212> TYPE: PRT

<213> ORGANISM: Artificial sequence
<220> FEATURE:
<223> OTHER INFORMATION: tab5 LC

<400> SEQUENCE: 73

Asp Ile Gln Met Thr Gln Ser Pro Ser Thr Leu Ser Ala Ser Val Gly
1               5                   10                  15

Asp Arg Val Thr Ile Thr Cys Arg Ala Gly Gln Ser Ile Ser Gly Trp
            20                  25                  30

Leu Ala Trp Phe Gln Gln Lys Pro Gly Lys Ala Pro Asn Leu Leu Ile
        35                  40                  45

Tyr Glu Thr Ser Thr Leu Glu Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Tyr Tyr Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 74
<211> LENGTH: 98
<212> TYPE: PRT
<213> ORGANISM: Artificial sequence
<220> FEATURE:
<223> OTHER INFORMATION: IGHV3-7 *01 HCVR

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

-continued

```
<210> SEQ ID NO 75
<211> LENGTH: 121
<212> TYPE: PRT
<213> ORGANISM: Artificial sequence
<220> FEATURE:
<223> OTHER INFORMATION: 20H1 HCVR

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Asp
            20                  25                  30

Cys Met Gly Trp Phe Arg Gln Ala Pro Gly Lys Gly Leu Glu Gly Val
        35                  40                  45

Ala His Ile Asp Ser Asp Gly Ile Pro Arg Tyr Val Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Val
                85                  90                  95

Val Gly Phe Lys Phe Asp Glu Asp Tyr Cys Ala Pro Asn Asp Trp Gly
            100                 105                 110

Gln Gly Thr Met Val Thr Val Ser Ser
        115                 120

<210> SEQ ID NO 76
<211> LENGTH: 121
<212> TYPE: PRT
<213> ORGANISM: Artificial sequence
<220> FEATURE:
<223> OTHER INFORMATION: 20H2 HCVR

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Arg Thr Asp
            20                  25                  30

Cys Met Gly Trp Phe Arg Gln Ala Pro Gly Lys Gly Leu Glu Gly Val
        35                  40                  45

Ala His Ile Asp Ser Asp Gly Ile Pro Arg Tyr Val Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Val
                85                  90                  95

Val Gly Phe Lys Phe Asp Glu Asp Tyr Cys Ala Pro Asn Asp Trp Gly
            100                 105                 110

Gln Gly Thr Met Val Thr Val Ser Ser
        115                 120

<210> SEQ ID NO 77
<211> LENGTH: 121
<212> TYPE: PRT
<213> ORGANISM: Artificial sequence
<220> FEATURE:
<223> OTHER INFORMATION: 20H3 HCVR

<400> SEQUENCE: 77

Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Tyr Thr Phe Ser Thr Asp
            20                  25                  30

Cys Met Gly Trp Phe Arg Gln Ala Pro Gly Lys Gly Leu Glu Gly Val
        35                  40                  45

Ala His Ile Asp Ser Asp Gly Ile Pro Arg Tyr Val Asp Ser Val Lys
    50                  55                  60

Gly Arg Phe Thr Ile Ser Gln Asp His Ala Lys Asn Ser Leu Tyr Leu
65                  70                  75                  80

Gln Met Asn Ser Leu Arg Ala Glu Asp Thr Ala Val Tyr Tyr Cys Val
                85                  90                  95

Val Gly Phe Lys Phe Asp Glu Asp Tyr Cys Ala Pro Asn Asp Trp Gly
            100                 105                 110

Gln Gly Thr Met Val Thr Val Ser Ser
        115                 120

<210> SEQ ID NO 78
<211> LENGTH: 121
<212> TYPE: PRT
<213> ORGANISM: Artificial sequence
<220> FEATURE:
<223> OTHER INFORMATION: 20H4 HCVR

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ser Arg Thr Asp
            20                  25                  30

Cys Met Gly Trp Phe Arg Gln Ala Pro Gly Lys Gly Leu Glu Gly Val
        35                  40                  45

Ala His Ile Asp Ser Asp Gly Ile Pro Arg Tyr Val Asp Ser Val Lys
    50                  55                  60

Gly Arg Phe Thr Ile Ser Gln Asp His Ala Lys Asn Ser Leu Tyr Leu
65                  70                  75                  80

Gln Met Asn Ser Leu Arg Ala Glu Asp Thr Ala Val Tyr Tyr Cys Val
                85                  90                  95

Val Gly Phe Lys Phe Asp Glu Asp Tyr Cys Ala Pro Asn Asp Trp Gly
            100                 105                 110

Gln Gly Thr Met Val Thr Val Ser Ser
        115                 120

<210> SEQ ID NO 79
<211> LENGTH: 121
<212> TYPE: PRT
<213> ORGANISM: Artificial sequence
<220> FEATURE:
<223> OTHER INFORMATION: 20H5 HCVR

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ser Arg Thr Asp
            20                  25                  30

Cys Met Gly Trp Phe Arg Gln Ala Pro Gly Lys Glu His Glu Gly Val
        35                  40                  45

Ala His Ile Asp Ser Asp Gly Ile Pro Arg Tyr Val Asp Ser Val Lys
    50                  55                  60

Gly Arg Phe Thr Ile Ser Gln Asp His Ala Lys Asn Ser Leu Tyr Leu
```

```
65                  70                  75                  80

Gln Met Asn Ser Leu Arg Ala Glu Asp Thr Ala Val Tyr Tyr Cys Val
                85                  90                  95

Val Gly Phe Lys Phe Asp Glu Asp Tyr Cys Ala Pro Asn Asp Trp Gly
                100                 105                 110

Gln Gly Thr Met Val Thr Val Ser Ser
        115                 120
```

```
<210> SEQ ID NO 80
<211> LENGTH: 120
<212> TYPE: PRT
<213> ORGANISM: Artificial sequence
<220> FEATURE:
<223> OTHER INFORMATION: 30H1 HCVR

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Asp
                20                  25                  30

Cys Met Gly Trp Phe Arg Gln Ala Pro Gly Lys Gly Leu Glu Gly Val
        35                  40                  45

Ala Thr Ile Asp Asn Ala Gly Arg Ile Lys Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Gly Trp Thr Phe Gly Gly Gln Cys Ser Pro Ala Asp Trp Gly Gln
        100                 105                 110

Gly Thr Gln Val Thr Val Ser Ser
        115                 120
```

```
<210> SEQ ID NO 81
<211> LENGTH: 121
<212> TYPE: PRT
<213> ORGANISM: Artificial sequence
<220> FEATURE:
<223> OTHER INFORMATION: 30H2 HCVR

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Asp
                20                  25                  30

Cys Met Gly Trp Phe Arg Gln Ala Pro Gly Lys Gly Leu Asp Glu Gly
        35                  40                  45

Val Ala Thr Ile Asp Asn Ala Gly Arg Ile Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ala Gly Trp Thr Phe Gly Gly Gln Cys Ser Pro Ala Asp Trp Gly
        100                 105                 110

Gln Gly Thr Gln Val Thr Val Ser Ser
        115                 120
```

<210> SEQ ID NO 82
<211> LENGTH: 121
<212> TYPE: PRT
<213> ORGANISM: Artificial sequence
<220> FEATURE:
<223> OTHER INFORMATION: 30H3 HCVR

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Tyr Ser Gly Asp
            20                  25                  30

Cys Met Gly Trp Phe Arg Gln Ala Pro Gly Lys Gly Leu Asp Glu Gly
        35                  40                  45

Val Ala Thr Ile Asp Asn Ala Gly Arg Ile Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ala Gly Trp Thr Phe Gly Gly Gln Cys Ser Pro Ala Asp Trp Gly
            100                 105                 110

Gln Gly Thr Gln Val Thr Val Ser Ser
        115                 120

<210> SEQ ID NO 83
<211> LENGTH: 121
<212> TYPE: PRT
<213> ORGANISM: Artificial sequence
<220> FEATURE:
<223> OTHER INFORMATION: 30H4 HCVR

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Asp
            20                  25                  30

Cys Met Gly Trp Phe Arg Gln Ala Pro Gly Lys Gly Leu Asp Glu Gly
        35                  40                  45

Val Ala Thr Ile Asp Asn Ala Gly Arg Ile Lys Tyr Ala Asp Ser Val
    50                  55                  60

Lys Gly Arg Phe Thr Ile Ser His Gly Asn Ala Lys Tyr Ile Leu Tyr
65                  70                  75                  80

Leu Gln Met Asn Ser Leu Arg Ala Glu Asp Thr Ala Val Tyr Tyr Cys
                85                  90                  95

Ala Ala Gly Trp Thr Phe Gly Gly Gln Cys Ser Pro Ala Asp Trp Gly
            100                 105                 110

Gln Gly Thr Gln Val Thr Val Ser Ser
        115                 120

<210> SEQ ID NO 84
<211> LENGTH: 121
<212> TYPE: PRT
<213> ORGANISM: Artificial sequence
<220> FEATURE:
<223> OTHER INFORMATION: 30H5 HCVR

<400> SEQUENCE: 84

Glu Val Gln Leu Val Glu Ser Gly Gly Gly Leu Val Gln Pro Gly Gly

```
1               5                   10                  15

Ser Leu Arg Leu Ser Cys Ala Ala Ser Gly Tyr Ser Tyr Ser Gly Asp
            20                  25                  30

Cys Met Gly Trp Phe Arg Gln Ala Pro Gly Lys Gly Leu Asp Glu Gly
            35                  40                  45

Val Ala Thr Ile Asp Asn Ala Gly Arg Ile Lys Tyr Ala Asp Ser Val
    50                  55                  60

Lys Gly Arg Phe Thr Ile Ser His Gly Asn Ala Lys Tyr Ile Leu Tyr
65                  70                  75                  80

Leu Gln Met Asn Ser Leu Arg Ala Glu Asp Thr Ala Val Tyr Tyr Cys
            85                  90                  95

Ala Ala Gly Trp Thr Phe Gly Gly Gln Cys Ser Pro Ala Asp Trp Gly
            100                 105                 110

Gln Gly Thr Gln Val Thr Val Ser Ser
            115                 120
```

<210> SEQ ID NO 85
<211> LENGTH: 98
<212> TYPE: PRT
<213> ORGANISM: Artificial sequence
<220> FEATURE:
<223> OTHER INFORMATION: IGHV3-30 *02

<400> SEQUENCE: 85

```
Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys
```

<210> SEQ ID NO 86
<211> LENGTH: 123
<212> TYPE: PRT
<213> ORGANISM: Artificial sequence
<220> FEATURE:
<223> OTHER INFORMATION: 38H2 HCVR

<400> SEQUENCE: 86

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Pro Ser
            20                  25                  30

Asp Met Ala Trp Phe Arg Gln Ala Pro Gly Lys Gly Leu Glu Gly Val
            35                  40                  45

Ala Thr Ile Ser Ala Ala Gly Arg Leu Thr Tyr Tyr Thr Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued

```
                        85                  90                  95

Ala Ala Asp Phe Ala Gly Gly Ser Ser Leu Phe Ala Asp Tyr Lys Tyr
                100                 105                 110

Trp Gly Gln Gly Thr Met Val Thr Val Ser Ser
        115                 120

<210> SEQ ID NO 87
<211> LENGTH: 123
<212> TYPE: PRT
<213> ORGANISM: Artificial sequence
<220> FEATURE:
<223> OTHER INFORMATION: 38H4 HCVR

<400> SEQUENCE: 87

Glu Val Gln Leu Val Glu Ser Gly Gly Gly Val Val Gln Pro Gly Gly
1               5                   10                  15

Ser Leu Arg Leu Ser Cys Ala Ala Ser Pro Phe Thr Tyr Gly Pro Ser
                20                  25                  30

Asp Met Ala Trp Phe Arg Gln Ala Pro Gly Lys Gly Leu Glu Gly Val
            35                  40                  45

Ala Thr Ile Ser Ala Ala Gly Arg Leu Thr Tyr Tyr Thr Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Phe Ala Gly Gly Ser Ser Leu Phe Ala Asp Tyr Lys Tyr
                100                 105                 110

Trp Gly Gln Gly Thr Met Val Thr Val Ser Ser
        115                 120

<210> SEQ ID NO 88
<211> LENGTH: 123
<212> TYPE: PRT
<213> ORGANISM: Artificial sequence
<220> FEATURE:
<223> OTHER INFORMATION: 38H7 HCVR

<400> SEQUENCE: 88

Glu Val Gln Leu Val Glu Ser Gly Gly Gly Val Val Gln Pro Gly Gly
1               5                   10                  15

Ser Leu Arg Leu Ser Cys Ala Ala Ser Pro Ser Thr Tyr Gly Pro Ser
                20                  25                  30

Asp Met Ala Trp Phe Arg Gln Ala Pro Gly Lys Gln Arg Glu Gly Val
            35                  40                  45

Ala Thr Ile Ser Ala Ala Gly Arg Leu Thr Tyr Tyr Thr Asp Ser Val
        50                  55                  60

Arg Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Ala Asp Phe Ala Gly Gly Ser Ser Leu Phe Ala Asp Tyr Lys Tyr
                100                 105                 110

Trp Gly Gln Gly Thr Met Val Thr Val Ser Ser
        115                 120

<210> SEQ ID NO 89
<211> LENGTH: 123
```

-continued

```
<212> TYPE: PRT
<213> ORGANISM: Artificial sequence
<220> FEATURE:
<223> OTHER INFORMATION: 38H8 HCVR

<400> SEQUENCE: 89

Glu Val Gln Leu Val Glu Ser Gly Gly Gly Val Val Gln Pro Gly Gly
1               5                   10                  15

Ser Leu Arg Leu Ser Cys Ala Ala Ser Pro Ser Thr Tyr Gly Pro Ser
            20                  25                  30

Asp Met Ala Trp Phe Arg Gln Ala Pro Gly Lys Gly Leu Glu Gly Val
        35                  40                  45

Ala Thr Ile Ser Ala Ala Gly Arg Leu Thr Tyr Tyr Thr Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Phe Ala Gly Gly Ser Ser Leu Phe Ala Asp Tyr Lys Tyr
            100                 105                 110

Trp Gly Gln Gly Thr Met Val Thr Val Ser Ser
        115                 120

<210> SEQ ID NO 90
<211> LENGTH: 123
<212> TYPE: PRT
<213> ORGANISM: Artificial sequence
<220> FEATURE:
<223> OTHER INFORMATION: 38H9 HCVR

<400> SEQUENCE: 90

Glu Val Gln Leu Val Glu Ser Gly Gly Gly Val Val Gln Pro Gly Gly
1               5                   10                  15

Ser Leu Arg Leu Ser Cys Ala Ala Ser Pro Ser Thr Tyr Gly Pro Ser
            20                  25                  30

Asp Met Ala Trp Phe Arg Gln Ala Pro Gly Lys Gly Leu Glu Gly Val
        35                  40                  45

Ala Thr Ile Ser Ala Ala Gly Arg Leu Thr Tyr Tyr Thr Asp Ser Val
        50                  55                  60

Arg Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Ala Asp Phe Ala Gly Gly Ser Ser Leu Phe Ala Asp Tyr Lys Tyr
            100                 105                 110

Trp Gly Gln Gly Thr Met Val Thr Val Ser Ser
        115                 120

<210> SEQ ID NO 91
<211> LENGTH: 120
<212> TYPE: PRT
<213> ORGANISM: Artificial sequence
<220> FEATURE:
<223> OTHER INFORMATION: 39H1 HCVR

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Asp
```

```
              20              25              30

Cys Met Gly Trp Phe Arg Gln Ala Pro Gly Lys Gly Leu Glu Gly Val
         35              40              45

Ala His Ile Asp Ser Asp Gly Ile Pro Arg Tyr Val Glu Ser Val Lys
     50              55              60

Gly Arg Phe Thr Ile Ser Arg Asp Asn Ala Lys Asn Ser Leu Tyr Leu
65              70              75              80

Gln Met Asn Ser Leu Arg Ala Glu Asp Thr Ala Val Tyr Tyr Cys Val
             85              90              95

Val Gly Phe Lys Phe Gly Asp Tyr Cys Ala Pro Asn Asp Trp Gly Gln
         100             105             110

Gly Thr Met Val Thr Val Ser Ser
         115             120
```

<210> SEQ ID NO 92
<211> LENGTH: 120
<212> TYPE: PRT
<213> ORGANISM: Artificial sequence
<220> FEATURE:
<223> OTHER INFORMATION: 39H2 HCVR

<400> SEQUENCE: 92

```
Glu Val Gln Leu Val Glu Ser Gly Gly Gly Leu Val Gln Pro Gly Gly
1               5              10              15

Ser Leu Arg Leu Ser Cys Ala Ala Ser Gly Phe Thr Ser Arg Thr Asp
         20              25              30

Cys Met Gly Trp Phe Arg Gln Ala Pro Gly Lys Gly Leu Glu Gly Val
         35              40              45

Ala His Ile Asp Ser Asp Gly Ile Pro Arg Tyr Val Glu Ser Val Lys
     50              55              60

Gly Arg Phe Thr Ile Ser Arg Asp Asn Ala Lys Asn Ser Leu Tyr Leu
65              70              75              80

Gln Met Asn Ser Leu Arg Ala Glu Asp Thr Ala Val Tyr Tyr Cys Val
             85              90              95

Val Gly Phe Lys Phe Gly Asp Tyr Cys Ala Pro Asn Asp Trp Gly Gln
         100             105             110

Gly Thr Met Val Thr Val Ser Ser
         115             120
```

<210> SEQ ID NO 93
<211> LENGTH: 120
<212> TYPE: PRT
<213> ORGANISM: Artificial sequence
<220> FEATURE:
<223> OTHER INFORMATION: 39H3 HCVR

<400> SEQUENCE: 93

```
Glu Val Gln Leu Val Glu Ser Gly Gly Gly Leu Val Gln Pro Gly Gly
1               5              10              15

Ser Leu Arg Leu Ser Cys Ala Ala Ser Gly Tyr Thr Phe Ser Thr Asp
         20              25              30

Cys Met Gly Trp Phe Arg Gln Ala Pro Gly Lys Gly Leu Glu Gly Val
         35              40              45

Ala His Ile Asp Ser Asp Gly Ile Pro Arg Tyr Val Glu Ser Val Lys
     50              55              60

Gly Arg Phe Thr Ile Ser Gln Asp His Ala Lys Asn Ser Leu Tyr Leu
65              70              75              80
```

```
Gln Met Asn Ser Leu Arg Ala Glu Asp Thr Ala Val Tyr Tyr Cys Val
                85                  90                  95

Val Gly Phe Lys Phe Gly Asp Tyr Cys Ala Pro Asn Asp Trp Gly Gln
            100                 105                 110

Gly Thr Met Val Thr Val Ser Ser
        115                 120
```

<210> SEQ ID NO 94
<211> LENGTH: 120
<212> TYPE: PRT
<213> ORGANISM: Artificial sequence
<220> FEATURE:
<223> OTHER INFORMATION: 39H4 HCVR

<400> SEQUENCE: 94

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ser Arg Thr Asp
                20                  25                  30

Cys Met Gly Trp Phe Arg Gln Ala Pro Gly Lys Gly Leu Glu Gly Val
            35                  40                  45

Ala His Ile Asp Ser Asp Gly Ile Pro Arg Tyr Val Glu Ser Val Lys
        50                  55                  60

Gly Arg Phe Thr Ile Ser Gln Asp His Ala Lys Asn Ser Leu Tyr Leu
65                  70                  75                  80

Gln Met Asn Ser Leu Arg Ala Glu Asp Thr Ala Val Tyr Tyr Cys Val
                85                  90                  95

Val Gly Phe Lys Phe Gly Asp Tyr Cys Ala Pro Asn Asp Trp Gly Gln
            100                 105                 110

Gly Thr Met Val Thr Val Ser Ser
        115                 120
```

<210> SEQ ID NO 95
<211> LENGTH: 120
<212> TYPE: PRT
<213> ORGANISM: Artificial sequence
<220> FEATURE:
<223> OTHER INFORMATION: 39H5 HCVR

<400> SEQUENCE: 95

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ser Arg Thr Asp
                20                  25                  30

Cys Met Gly Trp Phe Arg Gln Ala Pro Gly Lys Glu Arg Glu Gly Val
            35                  40                  45

Ala His Ile Asp Ser Asp Gly Ile Pro Arg Tyr Val Glu Ser Val Lys
        50                  55                  60

Gly Arg Phe Thr Ile Ser Gln Asp His Ala Lys Asn Ser Leu Tyr Leu
65                  70                  75                  80

Gln Met Asn Ser Leu Arg Ala Glu Asp Thr Ala Val Tyr Tyr Cys Val
                85                  90                  95

Val Gly Phe Lys Phe Gly Asp Tyr Cys Ala Pro Asn Asp Trp Gly Gln
            100                 105                 110

Gly Thr Met Val Thr Val Ser Ser
        115                 120
```

<210> SEQ ID NO 96

<211> LENGTH: 125
<212> TYPE: PRT
<213> ORGANISM: Artificial sequence
<220> FEATURE:
<223> OTHER INFORMATION: 151H2 HCVR

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Tyr Arg Pro Tyr
            20                  25                  30

Cys Met Ala Trp Phe Arg Gln Ala Pro Gly Lys Gly Leu Glu Ala Val
        35                  40                  45

Ala Gly Ile Asp Ile Phe Gly Gly Thr Thr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
            85                  90                  95

Ala Gly Asp Ser Pro Asp Gly Arg Cys Pro Pro Leu Gly Gln Gly Leu
            100                 105                 110

Asn Tyr Trp Gly Gln Gly Thr Met Val Thr Val Ser Ser
            115                 120                 125

<210> SEQ ID NO 97
<211> LENGTH: 127
<212> TYPE: PRT
<213> ORGANISM: Artificial sequence
<220> FEATURE:
<223> OTHER INFORMATION: 151H4 HCVR

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Val Ala Ser Ala Ser Gly Phe Thr Tyr Arg
            20                  25                  30

Pro Tyr Cys Met Ala Trp Phe Arg Gln Ala Pro Gly Lys Gly Leu Glu
        35                  40                  45

Ala Val Ala Gly Ile Asp Ile Phe Gly Gly Thr Thr Tyr Ala Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
            85                  90                  95

Cys Ala Ala Gly Asp Ser Pro Asp Gly Arg Cys Pro Pro Leu Gly Gln
            100                 105                 110

Gly Leu Asn Tyr Trp Gly Gln Gly Thr Met Val Thr Val Ser Ser
        115                 120                 125

<210> SEQ ID NO 98
<211> LENGTH: 127
<212> TYPE: PRT
<213> ORGANISM: Artificial sequence
<220> FEATURE:
<223> OTHER INFORMATION: 151H7 HCVR

<400> SEQUENCE: 98

His Val Gln Leu Val Glu Ser Gly Gly Gly Leu Val Gln Pro Gly Gly
1               5                   10                  15

```
Ser Leu Arg Leu Ser Cys Val Ala Ser Ala Ser Gly Phe Thr Tyr Arg
         20                  25                  30

Pro Tyr Cys Met Ala Trp Phe Arg Gln Ala Pro Gly Lys Glu Arg Glu
         35                  40                  45

Ala Val Ala Gly Ile Asp Ile Phe Gly Gly Thr Thr Tyr Ala Asp Ser
         50                  55                  60

Val Lys Gly Arg Phe Thr Ala Ser Arg Asp Asn Ala Gly Phe Ser Leu
65                  70                  75                  80

Tyr Leu Gln Met Asn Ser Leu Arg Ala Glu Asp Thr Ala Val Tyr Tyr
                 85                  90                  95

Cys Ala Ala Gly Asp Ser Pro Asp Gly Arg Cys Pro Pro Leu Gly Gln
             100                 105                 110

Gly Leu Asn Tyr Trp Gly Gln Gly Thr Met Val Thr Val Ser Ser
         115                 120                 125
```

<210> SEQ ID NO 99
<211> LENGTH: 127
<212> TYPE: PRT
<213> ORGANISM: Artificial sequence
<220> FEATURE:
<223> OTHER INFORMATION: 151H8 HCVR

<400> SEQUENCE: 99

```
Glu Val Gln Leu Val Glu Ser Gly Gly Gly Leu Val Gln Pro Gly Gly
1               5                   10                  15

Ser Leu Arg Leu Ser Cys Val Ala Ser Ala Ser Gly Phe Thr Tyr Arg
         20                  25                  30

Pro Tyr Cys Met Ala Trp Phe Arg Gln Ala Pro Gly Lys Gly Leu Glu
         35                  40                  45

Ala Val Ala Gly Ile Asp Ile Phe Gly Gly Thr Thr Tyr Ala Asp Ser
         50                  55                  60

Val Lys Gly Arg Phe Thr Ile Ser Arg Asp Asn Ala Gly Phe Ser Leu
65                  70                  75                  80

Tyr Leu Gln Met Asn Ser Leu Arg Ala Glu Asp Thr Ala Val Tyr Tyr
                 85                  90                  95

Cys Ala Ala Gly Asp Ser Pro Asp Gly Arg Cys Pro Pro Leu Gly Gln
             100                 105                 110

Gly Leu Asn Tyr Trp Gly Gln Gly Thr Met Val Thr Val Ser Ser
         115                 120                 125
```

<210> SEQ ID NO 100
<211> LENGTH: 127
<212> TYPE: PRT
<213> ORGANISM: Artificial sequence
<220> FEATURE:
<223> OTHER INFORMATION: 151H9 HCVR

<400> SEQUENCE: 100

```
His Val Gln Leu Val Glu Ser Gly Gly Gly Leu Val Gln Pro Gly Gly
1               5                   10                  15

Ser Leu Arg Leu Ser Cys Val Ala Ser Ala Ser Gly Phe Thr Tyr Arg
         20                  25                  30

Pro Tyr Cys Met Ala Trp Phe Arg Gln Ala Pro Gly Lys Gly Leu Glu
         35                  40                  45

Ala Val Ala Gly Ile Asp Ile Phe Gly Gly Thr Thr Tyr Ala Asp Ser
         50                  55                  60

Val Lys Gly Arg Phe Thr Ala Ser Arg Asp Asn Ala Gly Phe Ser Leu
65                  70                  75                  80
```

-continued

```
Tyr Leu Gln Met Asn Ser Leu Arg Ala Glu Asp Thr Ala Val Tyr Tyr
                85                      90                      95

Cys Ala Ala Gly Asp Ser Pro Asp Gly Arg Cys Pro Pro Leu Gly Gln
            100                     105                     110

Gly Leu Asn Tyr Trp Gly Gln Gly Thr Met Val Thr Val Ser Ser
        115                     120                     125
```

<210> SEQ ID NO 101
<211> LENGTH: 229
<212> TYPE: PRT
<213> ORGANISM: Artificial sequence
<220> FEATURE:
<223> OTHER INFORMATION: Fc region of human IgG4 heavy chain
      (S228P/F234A/L235A/K447A)

<400> SEQUENCE: 101

```
Glu Ser Lys Tyr Gly Pro Pro Cys Pro Pro Cys Pro Ala Pro Glu Ala
1               5                       10                      15

Ala Gly Gly Pro Ser Val Phe Leu Phe Pro Pro Lys Pro Lys Asp Thr
            20                      25                      30

Leu Met Ile Ser Arg Thr Pro Glu Val Thr Cys Val Val Val Asp Val
        35                      40                      45

Ser Gln Glu Asp Pro Glu Val Gln Phe Asn Trp Tyr Val Asp Gly Val
    50                      55                      60

Glu Val His Asn Ala Lys Thr Lys Pro Arg Glu Glu Gln Phe Asn Ser
65                      70                      75                      80

Thr Tyr Arg Val Val Ser Val Leu Thr Val Leu His Gln Asp Trp Leu
                85                      90                      95

Asn Gly Lys Glu Tyr Lys Cys Lys Val Ser Asn Lys Gly Leu Pro Ser
            100                     105                     110

Ser Ile Glu Lys Thr Ile Ser Lys Ala Lys Gly Gln Pro Arg Glu Pro
        115                     120                     125

Gln Val Tyr Thr Leu Pro Pro Ser Gln Glu Glu Met Thr Lys Asn Gln
        130                     135                     140

Val Ser Leu Thr Cys Leu Val Lys Gly Phe Tyr Pro Ser Asp Ile Ala
145                     150                     155                     160

Val Glu Trp Glu Ser Asn Gly Gln Pro Glu Asn Asn Tyr Lys Thr Thr
                165                     170                     175

Pro Pro Val Leu Asp Ser Asp Gly Ser Phe Phe Leu Tyr Ser Arg Leu
                180                     185                     190

Thr Val Asp Lys Ser Arg Trp Gln Glu Gly Asn Val Phe Ser Cys Ser
        195                     200                     205

Val Met His Glu Ala Leu His Asn His Tyr Thr Gln Lys Ser Leu Ser
    210                     215                     220

Leu Ser Leu Gly Ala
225
```

<210> SEQ ID NO 102
<211> LENGTH: 446
<212> TYPE: PRT
<213> ORGANISM: Artificial sequence
<220> FEATURE:
<223> OTHER INFORMATION: 1708TIGITHC

<400> SEQUENCE: 102

```
Glu Val Gln Leu Val Gln Ser Gly Ala Glu Val Lys Lys Pro Gly Ala
1               5                       10                      15
```

```
Ser Val Lys Val Ser Cys Lys Ala Ser Gly Tyr Thr Phe Thr Asn Tyr
        20              25                      30

Trp Met His Trp Val Arg Gln Ala Pro Gly Gln Gly Leu Glu Trp Met
        35              40                      45

Gly Arg Ile Asp Pro Asp Ser Thr Gly Ser Lys Tyr Asn Glu Lys Phe
    50              55                  60

Lys Thr Arg Val Thr Met Thr Arg Asp Thr Ser Thr Ser Thr Val Tyr
65                  70                  75                      80

Met Glu Leu Ser Ser Leu Arg Ser Glu Asp Thr Ala Val Tyr Tyr Cys
                85                  90                      95

Ala Arg Glu Gly Ala Tyr Gly Tyr Tyr Phe Asp Tyr Trp Gly Gln Gly
            100             105             110

Thr Leu Val Thr Val Ser Ser Ala Ser Thr Lys Gly Pro Ser Val Phe
            115             120             125

Pro Leu Ala Pro Cys Ser Arg Ser Thr Ser Glu Ser Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
            180             185             190

Ser Ser Leu Gly Thr Lys Thr Tyr Thr Cys Asn Val Asp His Lys Pro
            195             200             205

Ser Asn Thr Lys Val Asp Lys Arg Val Glu Ser Lys Tyr Gly Pro Pro
    210             215             220

Cys Pro Pro Cys Pro Ala Pro Glu Phe Leu Gly Gly Pro Ser Val Phe
225             230             235             240

Leu Phe Pro Pro Lys Pro Lys Asp Thr Leu Met Ile Ser Arg Thr Pro
            245             250             255

Glu Val Thr Cys Val Val Val Asp Val Ser Gln Glu Asp Pro Glu Val
            260             265             270

Gln Phe Asn Trp Tyr Val Asp Gly Val Glu Val His Asn Ala Lys Thr
            275             280             285

Lys Pro Arg Glu Glu Gln Phe Asn Ser Thr Tyr Arg Val Val Ser Val
    290             295             300

Leu Thr Val Leu His Gln Asp Trp Leu Asn Gly Lys Glu Tyr Lys Cys
305             310             315             320

Lys Val Ser Asn Lys Gly Leu Pro Ser Ser Ile Glu Lys Thr Ile Ser
            325             330             335

Lys Ala Lys Gly Gln Pro Arg Glu Pro Gln Val Tyr Thr Leu Pro Pro
            340             345             350

Ser Gln Glu Glu Met Thr Lys Asn Gln Val Ser Leu Thr Cys Leu Val
            355             360             365

Lys Gly Phe Tyr Pro Ser Asp Ile Ala Val Glu Trp Glu Ser Asn Gly
    370             375             380

Gln Pro Glu Asn Asn Tyr Lys Thr Thr Pro Pro Val Leu Asp Ser Asp
385             390             395             400

Gly Ser Phe Phe Leu Tyr Ser Arg Leu Thr Val Asp Lys Ser Arg Trp
            405             410             415

Gln Glu Gly Asn Val Phe Ser Cys Ser Val Met His Glu Ala Leu His
            420             425             430

Asn His Tyr Thr Gln Lys Ser Leu Ser Leu Ser Leu Gly Lys
```

```
               435                  440                  445

<210> SEQ ID NO 103
<211> LENGTH: 214
<212> TYPE: PRT
<213> ORGANISM: Artificial sequence
<220> FEATURE:
<223> OTHER INFORMATION: 1708TIGIT LC

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ser Pro Lys Leu Leu Ile
        35                  40                  45

Tyr Asn Ala Arg Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Tyr His Ser Gly Ser Pro Leu
                85                  90                  95

Pro Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 104
<211> LENGTH: 583
<212> TYPE: PRT
<213> ORGANISM: Artificial sequence
<220> FEATURE:
<223> OTHER INFORMATION: 1708-151-11511708N

<400> SEQUENCE: 104

His Val Gln Leu Val Glu Ser Gly Gly Gly Ser Val Gln Ala Gly Gly
1               5                   10                  15

Ser Leu Arg Leu Ser Cys Val Ala Ser Ala Ser Gly Phe Thr Tyr Arg
            20                  25                  30

Pro Tyr Cys Met Ala Trp Phe Arg Gln Ala Pro Gly Lys Glu Arg Glu
        35                  40                  45

Ala Val Ala Gly Ile Asp Ile Phe Gly Gly Thr Thr Tyr Ala Asp Ser
    50                  55                  60

Val Lys Gly Arg Phe Thr Ala Ser Arg Asp Asn Ala Gly Phe Ser Leu
65                  70                  75                  80
```

-continued

```
Phe Leu Gln Met Asn Asp Leu Lys Pro Glu Asp Thr Ala Met Tyr Tyr
             85                  90                  95

Cys Ala Ala Gly Asp Ser Pro Asp Gly Arg Cys Pro Pro Leu Gly Gln
            100             105             110

Gly Leu Asn Tyr Trp Gly Gln Gly Thr Gln Val Thr Val Ser Ser Gly
            115             120             125

Gly Gly Gly Ser Gly Gly Gly Ser Glu Val Gln Leu Val Gln Ser
    130             135             140

Gly Ala Glu Val Lys Lys Pro Gly Ala Ser Val Lys Val Ser Cys Lys
145             150             155             160

Ala Ser Gly Tyr Thr Phe Thr Asn Tyr Trp Met His Trp Val Arg Gln
            165             170             175

Ala Pro Gly Gln Gly Leu Glu Trp Met Gly Arg Ile Asp Pro Asp Ser
            180             185             190

Thr Gly Ser Lys Tyr Asn Glu Lys Phe Lys Thr Arg Val Thr Met Thr
            195             200             205

Arg Asp Thr Ser Thr Ser Thr Val Tyr Met Glu Leu Ser Ser Leu Arg
    210             215             220

Ser Glu Asp Thr Ala Val Tyr Tyr Cys Ala Arg Glu Gly Ala Tyr Gly
225             230             235             240

Tyr Tyr Phe Asp Tyr Trp Gly Gln Gly Thr Leu Val Thr Val Ser Ser
            245             250             255

Ala Ser Thr Lys Gly Pro Ser Val Phe Pro Leu Ala Pro Cys Ser Arg
            260             265             270

Ser Thr Ser Glu Ser Thr Ala Ala Leu Gly Cys Leu Val Lys Asp Tyr
            275             280             285

Phe Pro Glu Pro Val Thr Val Ser Trp Asn Ser Gly Ala Leu Thr Ser
    290             295             300

Gly Val His Thr Phe Pro Ala Val Leu Gln Ser Ser Gly Leu Tyr Ser
305             310             315             320

Leu Ser Ser Val Val Thr Val Pro Ser Ser Ser Leu Gly Thr Lys Thr
            325             330             335

Tyr Thr Cys Asn Val Asp His Lys Pro Ser Asn Thr Lys Val Asp Lys
            340             345             350

Arg Val Glu Ser Lys Tyr Gly Pro Pro Cys Pro Pro Cys Pro Ala Pro
            355             360             365

Glu Phe Leu Gly Gly Pro Ser Val Phe Leu Phe Pro Pro Lys Pro Lys
    370             375             380

Asp Thr Leu Met Ile Ser Arg Thr Pro Glu Val Thr Cys Val Val Val
385             390             395             400

Asp Val Ser Gln Glu Asp Pro Glu Val Gln Phe Asn Trp Tyr Val Asp
            405             410             415

Gly Val Glu Val His Asn Ala Lys Thr Lys Pro Arg Glu Glu Gln Phe
            420             425             430

Asn Ser Thr Tyr Arg Val Val Ser Val Leu Thr Val Leu His Gln Asp
            435             440             445

Trp Leu Asn Gly Lys Glu Tyr Lys Cys Lys Val Ser Asn Lys Gly Leu
    450             455             460

Pro Ser Ser Ile Glu Lys Thr Ile Ser Lys Ala Lys Gly Gln Pro Arg
465             470             475             480

Glu Pro Gln Val Tyr Thr Leu Pro Pro Ser Gln Glu Glu Met Thr Lys
            485             490             495

Asn Gln Val Ser Leu Thr Cys Leu Val Lys Gly Phe Tyr Pro Ser Asp
```

-continued

```
            500             505             510
Ile Ala Val Glu Trp Glu Ser Asn Gly Gln Pro Glu Asn Asn Tyr Lys
            515             520             525

Thr Thr Pro Pro Val Leu Asp Ser Asp Gly Ser Phe Phe Leu Tyr Ser
    530             535             540

Arg Leu Thr Val Asp Lys Ser Arg Trp Gln Glu Gly Asn Val Phe Ser
545             550             555             560

Cys Ser Val Met His Glu Ala Leu His Asn His Tyr Thr Gln Lys Ser
            565             570             575

Leu Ser Leu Ser Leu Gly Lys
            580

<210> SEQ ID NO 105
<211> LENGTH: 583
<212> TYPE: PRT
<213> ORGANISM: Artificial sequence
<220> FEATURE:
<223> OTHER INFORMATION: 1708-151-21511708C

<400> SEQUENCE: 105

Glu Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Asn Tyr
            20              25              30

Trp Met His Trp Val Arg Gln Ala Pro Gly Gln Gly Leu Glu Trp Met
        35              40              45

Gly Arg Ile Asp Pro Asp Ser Thr Gly Ser Lys Tyr Asn Glu Lys Phe
    50              55              60

Lys Thr Arg Val Thr Met Thr Arg Asp Thr Ser Thr Ser Thr Val Tyr
65              70              75              80

Met Glu Leu Ser Ser Leu Arg Ser Glu Asp Thr Ala Val Tyr Tyr Cys
                85              90              95

Ala Arg Glu Gly Ala Tyr Gly Tyr Tyr Phe Asp Tyr Trp Gly Gln Gly
            100             105             110

Thr Leu Val Thr Val Ser Ser Ala Ser Thr Lys Gly Pro Ser Val Phe
            115             120             125

Pro Leu Ala Pro Cys Ser Arg Ser Thr Ser Glu Ser Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
            180             185             190

Ser Ser Leu Gly Thr Lys Thr Tyr Thr Cys Asn Val Asp His Lys Pro
            195             200             205

Ser Asn Thr Lys Val Asp Lys Arg Val Glu Ser Lys Tyr Gly Pro Pro
    210             215             220

Cys Pro Pro Cys Pro Ala Pro Glu Phe Leu Gly Gly Pro Ser Val Phe
225             230             235             240

Leu Phe Pro Pro Lys Pro Lys Asp Thr Leu Met Ile Ser Arg Thr Pro
            245             250             255

Glu Val Thr Cys Val Val Val Asp Val Ser Gln Glu Asp Pro Glu Val
            260             265             270

Gln Phe Asn Trp Tyr Val Asp Gly Val Glu Val His Asn Ala Lys Thr
```

-continued

```
            275               280               285
Lys Pro Arg Glu Glu Gln Phe Asn Ser Thr Tyr Arg Val Val Ser Val
    290               295               300
Leu Thr Val Leu His Gln Asp Trp Leu Asn Gly Lys Glu Tyr Lys Cys
305               310               315               320
Lys Val Ser Asn Lys Gly Leu Pro Ser Ser Ile Glu Lys Thr Ile Ser
                325               330               335
Lys Ala Lys Gly Gln Pro Arg Glu Pro Gln Val Tyr Thr Leu Pro Pro
            340               345               350
Ser Gln Glu Glu Met Thr Lys Asn Gln Val Ser Leu Thr Cys Leu Val
            355               360               365
Lys Gly Phe Tyr Pro Ser Asp Ile Ala Val Glu Trp Glu Ser Asn Gly
    370               375               380
Gln Pro Glu Asn Asn Tyr Lys Thr Thr Pro Pro Val Leu Asp Ser Asp
385               390               395               400
Gly Ser Phe Phe Leu Tyr Ser Arg Leu Thr Val Asp Lys Ser Arg Trp
                405               410               415
Gln Glu Gly Asn Val Phe Ser Cys Ser Val Met His Glu Ala Leu His
            420               425               430
Asn His Tyr Thr Gln Lys Ser Leu Ser Leu Ser Leu Gly Lys Gly Gly
            435               440               445
Gly Gly Ser Gly Gly Gly Gly Ser His Val Gln Leu Val Glu Ser Gly
    450               455               460
Gly Gly Ser Val Gln Ala Gly Gly Ser Leu Arg Leu Ser Cys Val Ala
465               470               475               480
Ser Ala Ser Gly Phe Thr Tyr Arg Pro Tyr Cys Met Ala Trp Phe Arg
                485               490               495
Gln Ala Pro Gly Lys Glu Arg Glu Ala Val Ala Gly Ile Asp Ile Phe
            500               505               510
Gly Gly Thr Thr Tyr Ala Asp Ser Val Lys Gly Arg Phe Thr Ala Ser
            515               520               525
Arg Asp Asn Ala Gly Phe Ser Leu Phe Leu Gln Met Asn Asp Leu Lys
    530               535               540
Pro Glu Asp Thr Ala Met Tyr Tyr Cys Ala Ala Gly Asp Ser Pro Asp
545               550               555               560
Gly Arg Cys Pro Pro Leu Gly Gln Gly Leu Asn Tyr Trp Gly Gln Gly
                565               570               575
Thr Gln Val Thr Val Ser Ser
            580
```

```
<210> SEQ ID NO 106
<211> LENGTH: 351
<212> TYPE: PRT
<213> ORGANISM: Artificial sequence
<220> FEATURE:
<223> OTHER INFORMATION: 1708-151-31511708N

<400> SEQUENCE: 106

His Val Gln Leu Val Glu Ser Gly Gly Gly Ser Val Gln Ala Gly Gly
1               5               10               15
Ser Leu Arg Leu Ser Cys Val Ala Ser Ala Ser Gly Phe Thr Tyr Arg
            20               25               30
Pro Tyr Cys Met Ala Trp Phe Arg Gln Ala Pro Gly Lys Glu Arg Glu
        35               40               45
Ala Val Ala Gly Ile Asp Ile Phe Gly Gly Thr Thr Tyr Ala Asp Ser
```

-continued

```
            50              55              60

Val Lys Gly Arg Phe Thr Ala Ser Arg Asp Asn Ala Gly Phe Ser Leu
65              70              75              80

Phe Leu Gln Met Asn Asp Leu Lys Pro Glu Asp Thr Ala Met Tyr Tyr
                85              90              95

Cys Ala Ala Gly Asp Ser Pro Asp Gly Arg Cys Pro Pro Leu Gly Gln
            100             105             110

Gly Leu Asn Tyr Trp Gly Gln Gly Thr Gln Val Thr Val Ser Ser Gly
            115             120             125

Gly Gly Gly Ser Gly Gly Gly Ser Asp Ile Gln Met Thr Gln Ser
        130             135             140

Pro Ser Ser Leu Ser Ala Ser Val Gly Asp Arg Val Thr Ile Thr Cys
145             150             155             160

Arg Ala Ser Glu Asn Ile Tyr Ser Tyr Leu Ala Trp Tyr Gln Gln Lys
                165             170             175

Pro Gly Lys Ser Pro Lys Leu Leu Ile Tyr Asn Ala Arg Thr Leu Ala
            180             185             190

Glu Gly Val Pro Ser Arg Phe Ser Gly Ser Gly Ser Gly Thr Asp Phe
            195             200             205

Thr Leu Thr Ile Ser Ser Leu Gln Pro Glu Asp Phe Ala Thr Tyr Tyr
        210             215             220

Cys Gln Tyr His Ser Gly Ser Pro Leu Pro Phe Gly Gly Gly Thr Lys
225             230             235             240

Val Glu Ile Lys Arg Thr Val Ala Ala Pro Ser Val Phe Ile Phe Pro
            245             250             255

Pro Ser Asp Glu Gln Leu Lys Ser Gly Thr Ala Ser Val Val Cys Leu
            260             265             270

Leu Asn Asn Phe Tyr Pro Arg Glu Ala Lys Val Gln Trp Lys Val Asp
            275             280             285

Asn Ala Leu Gln Ser Gly Asn Ser Gln Glu Ser Val Thr Glu Gln Asp
        290             295             300

Ser Lys Asp Ser Thr Tyr Ser Leu Ser Ser Thr Leu Thr Leu Ser Lys
305             310             315             320

Ala Asp Tyr Glu Lys His Lys Val Tyr Ala Cys Glu Val Thr His Gln
            325             330             335

Gly Leu Ser Ser Pro Val Thr Lys Ser Phe Asn Arg Gly Glu Cys
            340             345             350
```

```
<210> SEQ ID NO 107
<211> LENGTH: 351
<212> TYPE: PRT
<213> ORGANISM: Artificial sequence
<220> FEATURE:
<223> OTHER INFORMATION: 1708-151-41511708C

<400> SEQUENCE: 107

Asp Ile Gln Met Thr Gln Ser Pro Ser Ser Leu Ser Ala Ser Val Gly
1               5               10              15

Asp Arg Val Thr Ile Thr Cys Arg Ala Ser Glu Asn Ile Tyr Ser Tyr
                20              25              30

Leu Ala Trp Tyr Gln Gln Lys Pro Gly Lys Ser Pro Lys Leu Leu Ile
            35              40              45

Tyr Asn Ala Arg Thr Leu Ala Glu Gly Val Pro Ser Arg Phe Ser Gly
        50              55              60

Ser Gly Ser Gly Thr Asp Phe Thr Leu Thr Ile Ser Ser Leu Gln Pro
```

-continued

```
65              70              75              80

Glu Asp Phe Ala Thr Tyr Tyr Cys Gln Tyr His Ser Gly Ser Pro Leu
                85              90              95

Pro Phe Gly Gly Gly Thr Lys Val Glu Ile Lys Arg Thr Val Ala Ala
                100             105             110

Pro Ser Val Phe Ile Phe Pro Pro Ser Asp Glu Gln Leu Lys Ser Gly
                115             120             125

Thr Ala Ser Val Val Cys Leu Leu Asn Asn Phe Tyr Pro Arg Glu Ala
        130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
                165             170             175

Ser Thr Leu Thr Leu Ser Lys Ala Asp Tyr Glu Lys His Lys Val Tyr
                180             185             190

Ala Cys Glu Val Thr His Gln Gly Leu Ser Ser Pro Val Thr Lys Ser
                195             200             205

Phe Asn Arg Gly Glu Cys Gly Gly Gly Ser Gly Gly Gly Ser
        210             215             220

His Val Gln Leu Val Glu Ser Gly Gly Gly Ser Val Gln Ala Gly Gly
225             230             235             240

Ser Leu Arg Leu Ser Cys Val Ala Ser Ala Ser Gly Phe Thr Tyr Arg
                245             250             255

Pro Tyr Cys Met Ala Trp Phe Arg Gln Ala Pro Gly Lys Glu Arg Glu
                260             265             270

Ala Val Ala Gly Ile Asp Ile Phe Gly Gly Thr Thr Tyr Ala Asp Ser
        275             280             285

Val Lys Gly Arg Phe Thr Ala Ser Arg Asp Asn Ala Gly Phe Ser Leu
        290             295             300

Phe Leu Gln Met Asn Asp Leu Lys Pro Glu Asp Thr Ala Met Tyr Tyr
305             310             315             320

Cys Ala Ala Gly Asp Ser Pro Asp Gly Arg Cys Pro Pro Leu Gly Gln
                325             330             335

Gly Leu Asn Tyr Trp Gly Gln Gly Thr Gln Val Thr Val Ser Ser
                340             345             350
```

```
<210> SEQ ID NO 108
<211> LENGTH: 577
<212> TYPE: PRT
<213> ORGANISM: Artificial sequence
<220> FEATURE:
<223> OTHER INFORMATION: 1708-20H5

<400> SEQUENCE: 108

Glu Val Gln Leu Val Glu Ser Gly Gly Gly Leu Val Gln Pro Gly Gly
1               5               10              15

Ser Leu Arg Leu Ser Cys Ala Ala Ser Gly Tyr Thr Ser Arg Thr Asp
                20              25              30

Cys Met Gly Trp Phe Arg Gln Ala Pro Gly Lys Glu His Glu Gly Val
            35              40              45

Ala His Ile Asp Ser Asp Gly Ile Pro Arg Tyr Val Asp Ser Val Lys
        50              55              60

Gly Arg Phe Thr Ile Ser Gln Asp His Ala Lys Asn Ser Leu Tyr Leu
65              70              75              80

Gln Met Asn Ser Leu Arg Ala Glu Asp Thr Ala Val Tyr Tyr Cys Val
```

-continued

```
                 85                  90                  95
Val Gly Phe Lys Phe Asp Glu Asp Tyr Cys Ala Pro Asn Asp Trp Gly
            100                 105                 110

Gln Gly Thr Met Val Thr Val Ser Ser Gly Gly Gly Ser Gly Gly
            115                 120                 125

Gly Gly Ser Glu Val Gln Leu Val Gln Ser Gly Ala Glu Val Lys Lys
            130                 135                 140

Pro Gly Ala Ser Val Lys Val Ser Cys Lys Ala Ser Gly Tyr Thr Phe
145                 150                 155                 160

Thr Asn Tyr Trp Met His Trp Val Arg Gln Ala Pro Gly Gln Gly Leu
                165                 170                 175

Glu Trp Met Gly Arg Ile Asp Pro Asp Ser Thr Gly Ser Lys Tyr Asn
                180                 185                 190

Glu Lys Phe Lys Thr Arg Val Thr Met Thr Arg Asp Thr Ser Thr Ser
                195                 200                 205

Thr Val Tyr Met Glu Leu Ser Ser Leu Arg Ser Glu Asp Thr Ala Val
            210                 215                 220

Tyr Tyr Cys Ala Arg Glu Gly Ala Tyr Gly Tyr Tyr Phe Asp Tyr Trp
225                 230                 235                 240

Gly Gln Gly Thr Leu Val Thr Val Ser Ser Ala Ser Thr Lys Gly Pro
                245                 250                 255

Ser Val Phe Pro Leu Ala Pro Cys Ser Arg Ser Thr Ser Glu Ser Thr
                260                 265                 270

Ala Ala Leu Gly Cys Leu Val Lys Asp Tyr Phe Pro Glu Pro Val Thr
            275                 280                 285

Val Ser Trp Asn Ser Gly Ala Leu Thr Ser Gly Val His Thr Phe Pro
            290                 295                 300

Ala Val Leu Gln Ser Ser Gly Leu Tyr Ser Leu Ser Ser Val Val Thr
305                 310                 315                 320

Val Pro Ser Ser Ser Leu Gly Thr Lys Thr Tyr Thr Cys Asn Val Asp
                325                 330                 335

His Lys Pro Ser Asn Thr Lys Val Asp Lys Arg Val Glu Ser Lys Tyr
                340                 345                 350

Gly Pro Pro Cys Pro Pro Cys Pro Ala Pro Glu Phe Leu Gly Gly Pro
                355                 360                 365

Ser Val Phe Leu Phe Pro Pro Lys Pro Lys Asp Thr Leu Met Ile Ser
            370                 375                 380

Arg Thr Pro Glu Val Thr Cys Val Val Val Asp Val Ser Gln Glu Asp
385                 390                 395                 400

Pro Glu Val Gln Phe Asn Trp Tyr Val Asp Gly Val Glu Val His Asn
                405                 410                 415

Ala Lys Thr Lys Pro Arg Glu Glu Gln Phe Asn Ser Thr Tyr Arg Val
                420                 425                 430

Val Ser Val Leu Thr Val Leu His Gln Asp Trp Leu Asn Gly Lys Glu
            435                 440                 445

Tyr Lys Cys Lys Val Ser Asn Lys Gly Leu Pro Ser Ser Ile Glu Lys
            450                 455                 460

Thr Ile Ser Lys Ala Lys Gly Gln Pro Arg Glu Pro Gln Val Tyr Thr
465                 470                 475                 480

Leu Pro Pro Ser Gln Glu Glu Met Thr Lys Asn Gln Val Ser Leu Thr
                485                 490                 495

Cys Leu Val Lys Gly Phe Tyr Pro Ser Asp Ile Ala Val Glu Trp Glu
                500                 505                 510
```

-continued

```
Ser Asn Gly Gln Pro Glu Asn Asn Tyr Lys Thr Thr Pro Pro Val Leu
        515                 520                 525

Asp Ser Asp Gly Ser Phe Phe Leu Tyr Ser Arg Leu Thr Val Asp Lys
        530                 535                 540

Ser Arg Trp Gln Glu Gly Asn Val Phe Ser Cys Ser Val Met His Glu
545                 550                 555                 560

Ala Leu His Asn His Tyr Thr Gln Lys Ser Leu Ser Leu Ser Leu Gly
                565                 570                 575

Lys

<210> SEQ ID NO 109
<211> LENGTH: 577
<212> TYPE: PRT
<213> ORGANISM: Artificial sequence
<220> FEATURE:
<223> OTHER INFORMATION: 1708-30H2

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Asp
        20                  25                  30

Cys Met Gly Trp Phe Arg Gln Ala Pro Gly Lys Gly Leu Asp Glu Gly
        35                  40                  45

Val Ala Thr Ile Asp Asn Ala Gly Arg Ile Lys Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ala Gly Trp Thr Phe Gly Gly Gln Cys Ser Pro Ala Asp Trp Gly
                100                 105                 110

Gln Gly Thr Gln Val Thr Val Ser Ser Gly Gly Gly Gly Ser Gly Gly
        115                 120                 125

Gly Gly Ser Glu Val Gln Leu Val Gln Ser Gly Ala Glu Val Lys Lys
        130                 135                 140

Pro Gly Ala Ser Val Lys Val Ser Cys Lys Ala Ser Gly Tyr Thr Phe
145                 150                 155                 160

Thr Asn Tyr Trp Met His Trp Val Arg Gln Ala Pro Gly Gln Gly Leu
                165                 170                 175

Glu Trp Met Gly Arg Ile Asp Pro Asp Ser Thr Gly Ser Lys Tyr Asn
                180                 185                 190

Glu Lys Phe Lys Thr Arg Val Thr Met Thr Arg Asp Thr Ser Thr Ser
        195                 200                 205

Thr Val Tyr Met Glu Leu Ser Ser Leu Arg Ser Glu Asp Thr Ala Val
        210                 215                 220

Tyr Tyr Cys Ala Arg Glu Gly Ala Tyr Gly Tyr Tyr Phe Asp Tyr Trp
225                 230                 235                 240

Gly Gln Gly Thr Leu Val Thr Val Ser Ser Ala Ser Thr Lys Gly Pro
                245                 250                 255

Ser Val Phe Pro Leu Ala Pro Cys Ser Arg Ser Thr Ser Glu Ser Thr
                260                 265                 270

Ala Ala Leu Gly Cys Leu Val Lys Asp Tyr Phe Pro Glu Pro Val Thr
        275                 280                 285
```

-continued

```
Val Ser Trp Asn Ser Gly Ala Leu Thr Ser Gly Val His Thr Phe Pro
    290                 295                 300

Ala Val Leu Gln Ser Ser Gly Leu Tyr Ser Leu Ser Ser Val Val Thr
305                 310                 315                 320

Val Pro Ser Ser Ser Leu Gly Thr Lys Thr Tyr Thr Cys Asn Val Asp
                325                 330                 335

His Lys Pro Ser Asn Thr Lys Val Asp Lys Arg Val Glu Ser Lys Tyr
                340                 345                 350

Gly Pro Pro Cys Pro Pro Cys Pro Ala Pro Glu Phe Leu Gly Gly Pro
                355                 360                 365

Ser Val Phe Leu Phe Pro Pro Lys Pro Lys Asp Thr Leu Met Ile Ser
    370                 375                 380

Arg Thr Pro Glu Val Thr Cys Val Val Val Asp Val Ser Gln Glu Asp
385                 390                 395                 400

Pro Glu Val Gln Phe Asn Trp Tyr Val Asp Gly Val Glu Val His Asn
                405                 410                 415

Ala Lys Thr Lys Pro Arg Glu Glu Gln Phe Asn Ser Thr Tyr Arg Val
                420                 425                 430

Val Ser Val Leu Thr Val Leu His Gln Asp Trp Leu Asn Gly Lys Glu
                435                 440                 445

Tyr Lys Cys Lys Val Ser Asn Lys Gly Leu Pro Ser Ser Ile Glu Lys
    450                 455                 460

Thr Ile Ser Lys Ala Lys Gly Gln Pro Arg Glu Pro Gln Val Tyr Thr
465                 470                 475                 480

Leu Pro Pro Ser Gln Glu Glu Met Thr Lys Asn Gln Val Ser Leu Thr
                485                 490                 495

Cys Leu Val Lys Gly Phe Tyr Pro Ser Asp Ile Ala Val Glu Trp Glu
                500                 505                 510

Ser Asn Gly Gln Pro Glu Asn Asn Tyr Lys Thr Thr Pro Pro Val Leu
                515                 520                 525

Asp Ser Asp Gly Ser Phe Phe Leu Tyr Ser Arg Leu Thr Val Asp Lys
    530                 535                 540

Ser Arg Trp Gln Glu Gly Asn Val Phe Ser Cys Ser Val Met His Glu
545                 550                 555                 560

Ala Leu His Asn His Tyr Thr Gln Lys Ser Leu Ser Leu Ser Leu Gly
                565                 570                 575

Lys
```

```
<210> SEQ ID NO 110
<211> LENGTH: 576
<212> TYPE: PRT
<213> ORGANISM: Artificial sequence
<220> FEATURE:
<223> OTHER INFORMATION: 1708-39H2

<400> SEQUENCE: 110

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Arg Thr Asp
                20                  25                  30

Cys Met Gly Trp Phe Arg Gln Ala Pro Gly Lys Gly Leu Glu Gly Val
                35                  40                  45

Ala His Ile Asp Ser Asp Gly Ile Pro Arg Tyr Val Glu Ser Val Lys
    50                  55                  60

Gly Arg Phe Thr Ile Ser Arg Asp Asn Ala Lys Asn Ser Leu Tyr Leu
```

-continued

```
65              70              75              80

Gln Met Asn Ser Leu Arg Ala Glu Asp Thr Ala Val Tyr Tyr Cys Val
             85              90              95

Val Gly Phe Lys Phe Gly Asp Tyr Cys Ala Pro Asn Asp Trp Gly Gln
            100             105             110

Gly Thr Met Val Thr Val Ser Ser Gly Gly Gly Ser Gly Gly Gly
            115             120             125

Gly Ser Glu Val Gln Leu Val Gln Ser Gly Ala Glu Val Lys Lys Pro
    130             135             140

Gly Ala Ser Val Lys Val Ser Cys Lys Ala Ser Gly Tyr Thr Phe Thr
145             150             155             160

Asn Tyr Trp Met His Trp Val Arg Gln Ala Pro Gly Gln Gly Leu Glu
            165             170             175

Trp Met Gly Arg Ile Asp Pro Asp Ser Thr Gly Ser Lys Tyr Asn Glu
            180             185             190

Lys Phe Lys Thr Arg Val Thr Met Thr Arg Asp Thr Ser Thr Ser Thr
            195             200             205

Val Tyr Met Glu Leu Ser Ser Leu Arg Ser Glu Asp Thr Ala Val Tyr
    210             215             220

Tyr Cys Ala Arg Glu Gly Ala Tyr Gly Tyr Tyr Phe Asp Tyr Trp Gly
225             230             235             240

Gln Gly Thr Leu Val Thr Val Ser Ser Ala Ser Thr Lys Gly Pro Ser
            245             250             255

Val Phe Pro Leu Ala Pro Cys Ser Arg Ser Thr Ser Glu Ser Thr Ala
            260             265             270

Ala Leu Gly Cys Leu Val Lys Asp Tyr Phe Pro Glu Pro Val Thr Val
            275             280             285

Ser Trp Asn Ser Gly Ala Leu Thr Ser Gly Val His Thr Phe Pro Ala
    290             295             300

Val Leu Gln Ser Ser Gly Leu Tyr Ser Leu Ser Ser Val Val Thr Val
305             310             315             320

Pro Ser Ser Ser Leu Gly Thr Lys Thr Tyr Thr Cys Asn Val Asp His
            325             330             335

Lys Pro Ser Asn Thr Lys Val Asp Lys Arg Val Glu Ser Lys Tyr Gly
            340             345             350

Pro Pro Cys Pro Pro Cys Pro Ala Pro Glu Phe Leu Gly Gly Pro Ser
            355             360             365

Val Phe Leu Phe Pro Pro Lys Pro Lys Asp Thr Leu Met Ile Ser Arg
    370             375             380

Thr Pro Glu Val Thr Cys Val Val Val Asp Val Ser Gln Glu Asp Pro
385             390             395             400

Glu Val Gln Phe Asn Trp Tyr Val Asp Gly Val Glu Val His Asn Ala
            405             410             415

Lys Thr Lys Pro Arg Glu Glu Gln Phe Asn Ser Thr Tyr Arg Val Val
            420             425             430

Ser Val Leu Thr Val Leu His Gln Asp Trp Leu Asn Gly Lys Glu Tyr
            435             440             445

Lys Cys Lys Val Ser Asn Lys Gly Leu Pro Ser Ser Ile Glu Lys Thr
    450             455             460

Ile Ser Lys Ala Lys Gly Gln Pro Arg Glu Pro Gln Val Tyr Thr Leu
465             470             475             480

Pro Pro Ser Gln Glu Glu Met Thr Lys Asn Gln Val Ser Leu Thr Cys
            485             490             495
```

```
Leu Val Lys Gly Phe Tyr Pro Ser Asp Ile Ala Val Glu Trp Glu Ser
            500             505             510

Asn Gly Gln Pro Glu Asn Asn Tyr Lys Thr Thr Pro Pro Val Leu Asp
            515             520             525

Ser Asp Gly Ser Phe Phe Leu Tyr Ser Arg Leu Thr Val Asp Lys Ser
            530             535             540

Arg Trp Gln Glu Gly Asn Val Phe Ser Cys Ser Val Met His Glu Ala
545             550             555             560

Leu His Asn His Tyr Thr Gln Lys Ser Leu Ser Leu Ser Leu Gly Lys
            565             570             575

<210> SEQ ID NO 111
<211> LENGTH: 583
<212> TYPE: PRT
<213> ORGANISM: Artificial sequence
<220> FEATURE:
<223> OTHER INFORMATION: 1708-151H7

<400> SEQUENCE: 111

His Val Gln Leu Val Glu Ser Gly Gly Gly Leu Val Gln Pro Gly Gly
1               5               10              15

Ser Leu Arg Leu Ser Cys Val Ala Ser Ala Ser Gly Phe Thr Tyr Arg
            20              25              30

Pro Tyr Cys Met Ala Trp Phe Arg Gln Ala Pro Gly Lys Glu Arg Glu
            35              40              45

Ala Val Ala Gly Ile Asp Ile Phe Gly Gly Thr Thr Tyr Ala Asp Ser
            50              55              60

Val Lys Gly Arg Phe Thr Ala Ser Arg Asp Asn Ala Gly Phe Ser Leu
65              70              75              80

Tyr Leu Gln Met Asn Ser Leu Arg Ala Glu Asp Thr Ala Val Tyr Tyr
                85              90              95

Cys Ala Ala Gly Asp Ser Pro Asp Gly Arg Cys Pro Pro Leu Gly Gln
            100             105             110

Gly Leu Asn Tyr Trp Gly Gln Gly Thr Met Val Thr Val Ser Ser Gly
            115             120             125

Gly Gly Gly Ser Gly Gly Gly Gly Ser Glu Val Gln Leu Val Gln Ser
            130             135             140

Gly Ala Glu Val Lys Lys Pro Gly Ala Ser Val Lys Val Ser Cys Lys
145             150             155             160

Ala Ser Gly Tyr Thr Phe Thr Asn Tyr Trp Met His Trp Val Arg Gln
            165             170             175

Ala Pro Gly Gln Gly Leu Glu Trp Met Gly Arg Ile Asp Pro Asp Ser
            180             185             190

Thr Gly Ser Lys Tyr Asn Glu Lys Phe Lys Thr Arg Val Thr Met Thr
            195             200             205

Arg Asp Thr Ser Thr Ser Thr Val Tyr Met Glu Leu Ser Ser Leu Arg
            210             215             220

Ser Glu Asp Thr Ala Val Tyr Tyr Cys Ala Arg Glu Gly Ala Tyr Gly
225             230             235             240

Tyr Tyr Phe Asp Tyr Trp Gly Gln Gly Thr Leu Val Thr Val Ser Ser
            245             250             255

Ala Ser Thr Lys Gly Pro Ser Val Phe Pro Leu Ala Pro Cys Ser Arg
            260             265             270

Ser Thr Ser Glu Ser Thr Ala Ala Leu Gly Cys Leu Val Lys Asp Tyr
            275             280             285
```

-continued

Phe Pro Glu Pro Val Thr Val Ser Trp Asn Ser Gly Ala Leu Thr Ser
    290                 295                 300

Gly Val His Thr Phe Pro Ala Val Leu Gln Ser Ser Gly Leu Tyr Ser
305                 310                 315                 320

Leu Ser Ser Val Val Thr Val Pro Ser Ser Ser Leu Gly Thr Lys Thr
                325                 330                 335

Tyr Thr Cys Asn Val Asp His Lys Pro Ser Asn Thr Lys Val Asp Lys
            340                 345                 350

Arg Val Glu Ser Lys Tyr Gly Pro Pro Cys Pro Pro Cys Pro Ala Pro
        355                 360                 365

Glu Phe Leu Gly Gly Pro Ser Val Phe Leu Phe Pro Pro Lys Pro Lys
    370                 375                 380

Asp Thr Leu Met Ile Ser Arg Thr Pro Glu Val Thr Cys Val Val Val
385                 390                 395                 400

Asp Val Ser Gln Glu Asp Pro Glu Val Gln Phe Asn Trp Tyr Val Asp
                405                 410                 415

Gly Val Glu Val His Asn Ala Lys Thr Lys Pro Arg Glu Glu Gln Phe
                420                 425                 430

Asn Ser Thr Tyr Arg Val Val Ser Val Leu Thr Val Leu His Gln Asp
            435                 440                 445

Trp Leu Asn Gly Lys Glu Tyr Lys Cys Lys Val Ser Asn Lys Gly Leu
    450                 455                 460

Pro Ser Ser Ile Glu Lys Thr Ile Ser Lys Ala Lys Gly Gln Pro Arg
465                 470                 475                 480

Glu Pro Gln Val Tyr Thr Leu Pro Pro Ser Gln Glu Glu Met Thr Lys
                485                 490                 495

Asn Gln Val Ser Leu Thr Cys Leu Val Lys Gly Phe Tyr Pro Ser Asp
            500                 505                 510

Ile Ala Val Glu Trp Glu Ser Asn Gly Gln Pro Glu Asn Asn Tyr Lys
            515                 520                 525

Thr Thr Pro Pro Val Leu Asp Ser Asp Gly Ser Phe Phe Leu Tyr Ser
    530                 535                 540

Arg Leu Thr Val Asp Lys Ser Arg Trp Gln Glu Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Leu Gly Lys
                580

<210> SEQ ID NO 112
<211> LENGTH: 583
<212> TYPE: PRT
<213> ORGANISM: Artificial sequence
<220> FEATURE:
<223> OTHER INFORMATION: 1708-151H8

<400> SEQUENCE: 112

Glu Val Gln Leu Val Glu Ser Gly Gly Gly Leu Val Gln Pro Gly Gly
1                   5                   10                  15

Ser Leu Arg Leu Ser Cys Val Ala Ser Ala Ser Gly Phe Thr Tyr Arg
            20                  25                  30

Pro Tyr Cys Met Ala Trp Phe Arg Gln Ala Pro Gly Lys Gly Leu Glu
        35                  40                  45

Ala Val Ala Gly Ile Asp Ile Phe Gly Gly Thr Thr Tyr Ala Asp Ser
    50                  55                  60

```
Val Lys Gly Arg Phe Thr Ile Ser Arg Asp Asn Ala Gly Phe Ser Leu
65              70                  75              80

Tyr Leu Gln Met Asn Ser Leu Arg Ala Glu Asp Thr Ala Val Tyr Tyr
                85                  90                  95

Cys Ala Ala Gly Asp Ser Pro Asp Gly Arg Cys Pro Pro Leu Gly Gln
            100                 105                 110

Gly Leu Asn Tyr Trp Gly Gln Gly Thr Met Val Thr Val Ser Ser Gly
            115                 120                 125

Gly Gly Gly Ser Gly Gly Gly Ser Glu Val Gln Leu Val Gln Ser
        130                 135                 140

Gly Ala Glu Val Lys Lys Pro Gly Ala Ser Val Lys Val Ser Cys Lys
145                 150                 155                 160

Ala Ser Gly Tyr Thr Phe Thr Asn Tyr Trp Met His Trp Val Arg Gln
                165                 170                 175

Ala Pro Gly Gln Gly Leu Glu Trp Met Gly Arg Ile Asp Pro Asp Ser
            180                 185                 190

Thr Gly Ser Lys Tyr Asn Glu Lys Phe Lys Thr Arg Val Thr Met Thr
            195                 200                 205

Arg Asp Thr Ser Thr Ser Thr Val Tyr Met Glu Leu Ser Ser Leu Arg
    210                 215                 220

Ser Glu Asp Thr Ala Val Tyr Tyr Cys Ala Arg Glu Gly Ala Tyr Gly
225                 230                 235                 240

Tyr Tyr Phe Asp Tyr Trp Gly Gln Gly Thr Leu Val Thr Val Ser Ser
            245                 250                 255

Ala Ser Thr Lys Gly Pro Ser Val Phe Pro Leu Ala Pro Cys Ser Arg
            260                 265                 270

Ser Thr Ser Glu Ser Thr Ala Ala Leu Gly Cys Leu Val Lys Asp Tyr
            275                 280                 285

Phe Pro Glu Pro Val Thr Val Ser Trp Asn Ser Gly Ala Leu Thr Ser
    290                 295                 300

Gly Val His Thr Phe Pro Ala Val Leu Gln Ser Ser Gly Leu Tyr Ser
305                 310                 315                 320

Leu Ser Ser Val Val Thr Val Pro Ser Ser Ser Leu Gly Thr Lys Thr
            325                 330                 335

Tyr Thr Cys Asn Val Asp His Lys Pro Ser Asn Thr Lys Val Asp Lys
            340                 345                 350

Arg Val Glu Ser Lys Tyr Gly Pro Pro Cys Pro Pro Cys Pro Ala Pro
            355                 360                 365

Glu Phe Leu Gly Gly Pro Ser Val Phe Leu Phe Pro Pro Lys Pro Lys
    370                 375                 380

Asp Thr Leu Met Ile Ser Arg Thr Pro Glu Val Thr Cys Val Val Val
385                 390                 395                 400

Asp Val Ser Gln Glu Asp Pro Glu Val Gln Phe Asn Trp Tyr Val Asp
            405                 410                 415

Gly Val Glu Val His Asn Ala Lys Thr Lys Pro Arg Glu Glu Gln Phe
            420                 425                 430

Asn Ser Thr Tyr Arg Val Val Ser Val Leu Thr Val Leu His Gln Asp
            435                 440                 445

Trp Leu Asn Gly Lys Glu Tyr Lys Cys Lys Val Ser Asn Lys Gly Leu
    450                 455                 460

Pro Ser Ser Ile Glu Lys Thr Ile Ser Lys Ala Lys Gly Gln Pro Arg
465                 470                 475                 480
```

-continued

```
Glu Pro Gln Val Tyr Thr Leu Pro Pro Ser Gln Glu Glu Met Thr Lys
            485                 490                 495

Asn Gln Val Ser Leu Thr Cys Leu Val Lys Gly Phe Tyr Pro Ser Asp
            500                 505                 510

Ile Ala Val Glu Trp Glu Ser Asn Gly Gln Pro Glu Asn Asn Tyr Lys
            515                 520                 525

Thr Thr Pro Pro Val Leu Asp Ser Asp Gly Ser Phe Phe Leu Tyr Ser
        530                 535                 540

Arg Leu Thr Val Asp Lys Ser Arg Trp Gln Glu Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Leu Gly Lys
                580
```

<210> SEQ ID NO 113
<211> LENGTH: 449
<212> TYPE: PRT
<213> ORGANISM: Artificial sequence
<220> FEATURE:
<223> OTHER INFORMATION: 1708-IgG1 (1708IgG1) HC

<400> SEQUENCE: 113

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
            35                  40                  45

Gly Arg Ile Asp Pro Asp Ser Thr Gly Ser Lys Tyr Asn Glu Lys Phe
        50                  55                  60

Lys Thr Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Ala Tyr Gly Tyr Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

-continued

```
Arg Thr Pro Glu Val Thr Cys Val Val Val Asp Val Ser His Glu Asp
        260             265             270

Pro Glu Val Lys Phe Asn Trp Tyr Val Asp Gly Val Glu Val His Asn
        275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
                325             330             335

Thr Ile Ser Lys Ala Lys Gly Gln Pro Arg Glu Pro Gln Val Tyr Thr
            340             345             350

Leu Pro Pro Ser Arg Glu Glu Met Thr Lys Asn Gln Val Ser Leu Thr
        355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
        435             440             445

Lys
```

```
<210> SEQ ID NO 114
<211> LENGTH: 586
<212> TYPE: PRT
<213> ORGANISM: Artificial sequence
<220> FEATURE:
<223> OTHER INFORMATION: 1708-151-IgG1 (1708-151IgG1)

<400> SEQUENCE: 114
```

```
His Val Gln Leu Val Glu Ser Gly Gly Gly Ser Val Gln Ala Gly Gly
1               5               10              15

Ser Leu Arg Leu Ser Cys Val Ala Ser Ala Ser Gly Phe Thr Tyr Arg
        20              25              30

Pro Tyr Cys Met Ala Trp Phe Arg Gln Ala Pro Gly Lys Glu Arg Glu
        35              40              45

Ala Val Ala Gly Ile Asp Ile Phe Gly Gly Thr Thr Tyr Ala Asp Ser
    50              55              60

Val Lys Gly Arg Phe Thr Ala Ser Arg Asp Asn Ala Gly Phe Ser Leu
65              70              75              80

Phe Leu Gln Met Asn Asp Leu Lys Pro Glu Asp Thr Ala Met Tyr Tyr
            85              90              95

Cys Ala Ala Gly Asp Ser Pro Asp Gly Arg Cys Pro Pro Leu Gly Gln
            100             105             110

Gly Leu Asn Tyr Trp Gly Gln Gly Thr Gln Val Thr Val Ser Ser Gly
        115             120             125

Gly Gly Gly Ser Gly Gly Gly Gly Ser Glu Val Gln Leu Val Gln Ser
        130             135             140

Gly Ala Glu Val Lys Lys Pro Gly Ala Ser Val Lys Val Ser Cys Lys
145             150             155             160

Ala Ser Gly Tyr Thr Phe Thr Asn Tyr Trp Met His Trp Val Arg Gln
```

-continued

```
              165               170                 175

Ala Pro Gly Gln Gly Leu Glu Trp Met Gly Arg Ile Asp Pro Asp Ser
              180               185                 190

Thr Gly Ser Lys Tyr Asn Glu Lys Phe Lys Thr Arg Val Thr Met Thr
              195               200                 205

Arg Asp Thr Ser Thr Ser Thr Val Tyr Met Glu Leu Ser Ser Leu Arg
    210               215                 220

Ser Glu Asp Thr Ala Val Tyr Tyr Cys Ala Arg Glu Gly Ala Tyr Gly
225               230                 235                 240

Tyr Tyr Phe Asp Tyr Trp Gly Gln Gly Thr Leu Val Thr Val Ser Ser
              245               250                 255

Ala Ser Thr Lys Gly Pro Ser Val Phe Pro Leu Ala Pro Ser Ser Lys
              260               265                 270

Ser Thr Ser Gly Gly Thr Ala Ala Leu Gly Cys Leu Val Lys Asp Tyr
              275               280                 285

Phe Pro Glu Pro Val Thr Val Ser Trp Asn Ser Gly Ala Leu Thr Ser
    290               295                 300

Gly Val His Thr Phe Pro Ala Val Leu Gln Ser Ser Gly Leu Tyr Ser
305               310                 315                 320

Leu Ser Ser Val Val Thr Val Pro Ser Ser Ser Leu Gly Thr Gln Thr
              325               330                 335

Tyr Ile Cys Asn Val Asn His Lys Pro Ser Asn Thr Lys Val Asp Lys
              340               345                 350

Lys Val Glu Pro Lys Ser Cys Asp Lys Thr His Thr Cys Pro Pro Cys
              355               360                 365

Pro Ala Pro Glu Leu Leu Gly Gly Pro Ser Val Phe Leu Phe Pro Pro
    370               375                 380

Lys Pro Lys Asp Thr Leu Met Ile Ser Arg Thr Pro Glu Val Thr Cys
385               390                 395                 400

Val Val Val Asp Val Ser His Glu Asp Pro Glu Val Lys Phe Asn Trp
              405               410                 415

Tyr Val Asp Gly Val Glu Val His Asn Ala Lys Thr Lys Pro Arg Glu
              420               425                 430

Glu Gln Tyr Asn Ser Thr Tyr Arg Val Val Ser Val Leu Thr Val Leu
              435               440                 445

His Gln Asp Trp Leu Asn Gly Lys Glu Tyr Lys Cys Lys Val Ser Asn
    450               455                 460

Lys Ala Leu Pro Ala Pro Ile Glu Lys Thr Ile Ser Lys Ala Lys Gly
465               470                 475                 480

Gln Pro Arg Glu Pro Gln Val Tyr Thr Leu Pro Pro Ser Arg Glu Glu
              485               490                 495

Met Thr Lys Asn Gln Val Ser Leu Thr Cys Leu Val Lys Gly Phe Tyr
              500               505                 510

Pro Ser Asp Ile Ala Val Glu Trp Glu Ser Asn Gly Gln Pro Glu Asn
              515               520                 525

Asn Tyr Lys Thr Thr Pro Pro Val Leu Asp Ser Asp Gly Ser Phe Phe
    530               535                 540

Leu Tyr Ser Lys Leu Thr Val Asp Lys Ser Arg Trp Gln Gln Gly Asn
545               550                 555                 560

Val Phe Ser Cys Ser Val Met His Glu Ala Leu His Asn His Tyr Thr
              565               570                 575

Gln Lys Ser Leu Ser Leu Ser Pro Gly Lys
              580               585
```

-continued

<210> SEQ ID NO 115
<211> LENGTH: 5
<212> TYPE: PRT
<213> ORGANISM: Artificial sequence
<220> FEATURE:
<223> OTHER INFORMATION: 1707 HCDR1

<400> SEQUENCE: 115

Asp Tyr His Met Tyr
1               5

<210> SEQ ID NO 116
<211> LENGTH: 17
<212> TYPE: PRT
<213> ORGANISM: Artificial sequence
<220> FEATURE:
<223> OTHER INFORMATION: 1707 HCDR2

<400> SEQUENCE: 116

Tyr Ile Ser Lys Gly Gly Ile Ser Thr Tyr Tyr Pro Asp Thr Val Lys
1               5                   10                  15

Gly

<210> SEQ ID NO 117
<211> LENGTH: 10
<212> TYPE: PRT
<213> ORGANISM: Artificial sequence
<220> FEATURE:
<223> OTHER INFORMATION: 1707 HCDR3

<400> SEQUENCE: 117

Gln Ser Ser Tyr Asp Phe Ala Met Asp Tyr
1               5                   10

<210> SEQ ID NO 118
<211> LENGTH: 11
<212> TYPE: PRT
<213> ORGANISM: Artificial sequence
<220> FEATURE:
<223> OTHER INFORMATION: 1707 LCDR1

<400> SEQUENCE: 118

Lys Ala Ser Gln Asp Val Gly Thr Ser Val Ala
1               5                   10

<210> SEQ ID NO 119
<211> LENGTH: 7
<212> TYPE: PRT
<213> ORGANISM: Artificial sequence
<220> FEATURE:
<223> OTHER INFORMATION: 1707 LCDR2

<400> SEQUENCE: 119

Trp Ala Ser Ala Arg His Thr
1               5

<210> SEQ ID NO 120
<211> LENGTH: 9
<212> TYPE: PRT
<213> ORGANISM: Artificial sequence
<220> FEATURE:
<223> OTHER INFORMATION: 1707 LCDR3

<400> SEQUENCE: 120

Gln Gln Tyr Ser Ser Tyr Pro Leu Thr

-continued

```
1               5

<210> SEQ ID NO 121
<211> LENGTH: 5
<212> TYPE: PRT
<213> ORGANISM: Artificial sequence
<220> FEATURE:
<223> OTHER INFORMATION: 1708 HCDR1

<400> SEQUENCE: 121

Asn Tyr Trp Met His
1               5

<210> SEQ ID NO 122
<211> LENGTH: 17
<212> TYPE: PRT
<213> ORGANISM: Artificial sequence
<220> FEATURE:
<223> OTHER INFORMATION: 1708 HCDR2

<400> SEQUENCE: 122

Arg Ile Asp Pro Asp Ser Thr Gly Ser Lys Tyr Asn Glu Lys Phe Lys
1               5                   10                  15

Thr

<210> SEQ ID NO 123
<211> LENGTH: 10
<212> TYPE: PRT
<213> ORGANISM: Artificial sequence
<220> FEATURE:
<223> OTHER INFORMATION: 1708 HCDR3

<400> SEQUENCE: 123

Glu Gly Ala Tyr Gly Tyr Tyr Phe Asp Tyr
1               5                   10

<210> SEQ ID NO 124
<211> LENGTH: 11
<212> TYPE: PRT
<213> ORGANISM: Artificial sequence
<220> FEATURE:
<223> OTHER INFORMATION: 1708 LCDR1

<400> SEQUENCE: 124

Arg Ala Ser Glu Asn Ile Tyr Ser Tyr Leu Ala
1               5                   10

<210> SEQ ID NO 125
<211> LENGTH: 7
<212> TYPE: PRT
<213> ORGANISM: Artificial sequence
<220> FEATURE:
<223> OTHER INFORMATION: 1708 LCDR2

<400> SEQUENCE: 125

Asn Ala Arg Thr Leu Ala Glu
1               5

<210> SEQ ID NO 126
<211> LENGTH: 9
<212> TYPE: PRT
<213> ORGANISM: Artificial sequence
<220> FEATURE:
<223> OTHER INFORMATION: 1708 LCDR3

<400> SEQUENCE: 126
```

```
Gln Tyr His Ser Gly Ser Pro Leu Pro
1               5

<210> SEQ ID NO 127
<211> LENGTH: 5
<212> TYPE: PRT
<213> ORGANISM: Artificial sequence
<220> FEATURE:
<223> OTHER INFORMATION: 1709 HCDR1

<400> SEQUENCE: 127

Asp Tyr Tyr Met His
1               5

<210> SEQ ID NO 128
<211> LENGTH: 17
<212> TYPE: PRT
<213> ORGANISM: Artificial sequence
<220> FEATURE:
<223> OTHER INFORMATION: 1709 HCDR2

<400> SEQUENCE: 128

Leu Val Tyr Pro Tyr Asn Asp Asn Thr Gly Tyr Asn Arg Lys Phe Lys
1               5                   10                  15

Gly

<210> SEQ ID NO 129
<211> LENGTH: 11
<212> TYPE: PRT
<213> ORGANISM: Artificial sequence
<220> FEATURE:
<223> OTHER INFORMATION: 1709 HCDR3

<400> SEQUENCE: 129

Gly Gly Pro Ser Asn Trp Asn Tyr Phe Asp Tyr
1               5                   10

<210> SEQ ID NO 130
<211> LENGTH: 11
<212> TYPE: PRT
<213> ORGANISM: Artificial sequence
<220> FEATURE:
<223> OTHER INFORMATION: 1709 LCDR1

<400> SEQUENCE: 130

Lys Ala Ser Gln Asn Val Val Thr Ala Val Ala
1               5                   10

<210> SEQ ID NO 131
<211> LENGTH: 7
<212> TYPE: PRT
<213> ORGANISM: Artificial sequence
<220> FEATURE:
<223> OTHER INFORMATION: 1709 LCDR2

<400> SEQUENCE: 131

Ser Ala Ser Asn Arg Tyr Thr
1               5

<210> SEQ ID NO 132
<211> LENGTH: 9
<212> TYPE: PRT
<213> ORGANISM: Artificial sequence
<220> FEATURE:
<223> OTHER INFORMATION: 1709 HCDR3

<400> SEQUENCE: 132
```

```
Gln Gln Tyr Thr Leu Tyr Pro Leu Thr
1               5

<210> SEQ ID NO 133
<211> LENGTH: 5
<212> TYPE: PRT
<213> ORGANISM: Artificial sequence
<220> FEATURE:
<223> OTHER INFORMATION: 1710 HCDR1

<400> SEQUENCE: 133

Asn Tyr Tyr Met His
1               5

<210> SEQ ID NO 134
<211> LENGTH: 17
<212> TYPE: PRT
<213> ORGANISM: Artificial sequence
<220> FEATURE:
<223> OTHER INFORMATION: 1710 HCDR2

<400> SEQUENCE: 134

Arg Ile Asp Pro Thr Ser Gly Ala Thr Lys Tyr Asn Asp Asn Phe Lys
1               5                   10                  15

Gly

<210> SEQ ID NO 135
<211> LENGTH: 10
<212> TYPE: PRT
<213> ORGANISM: Artificial sequence
<220> FEATURE:
<223> OTHER INFORMATION: 1710 HCDR3

<400> SEQUENCE: 135

Glu Gly Gly Phe Gly Tyr Tyr Phe Asp Tyr
1               5                   10

<210> SEQ ID NO 136
<211> LENGTH: 11
<212> TYPE: PRT
<213> ORGANISM: Artificial sequence
<220> FEATURE:
<223> OTHER INFORMATION: 1710 LCDR1

<400> SEQUENCE: 136

Arg Thr Ser Glu Asn Ile Phe Thr Tyr Leu Ala
1               5                   10

<210> SEQ ID NO 137
<211> LENGTH: 7
<212> TYPE: PRT
<213> ORGANISM: Artificial sequence
<220> FEATURE:
<223> OTHER INFORMATION: 1710 LCDR2

<400> SEQUENCE: 137

Asn Ala Lys Thr Phe Ala Glu
1               5

<210> SEQ ID NO 138
<211> LENGTH: 9
<212> TYPE: PRT
<213> ORGANISM: Artificial sequence
<220> FEATURE:
<223> OTHER INFORMATION: 1710 LCDR3
```

-continued

```
<400> SEQUENCE: 138

Gln His His Tyr Gly Ile Pro Leu Pro
1               5

<210> SEQ ID NO 139
<211> LENGTH: 5
<212> TYPE: PRT
<213> ORGANISM: Artificial sequence
<220> FEATURE:
<223> OTHER INFORMATION: 1711 HCDR1

<400> SEQUENCE: 139

Asn Tyr Trp Ile Gly
1               5

<210> SEQ ID NO 140
<211> LENGTH: 17
<212> TYPE: PRT
<213> ORGANISM: Artificial sequence
<220> FEATURE:
<223> OTHER INFORMATION: 1711 HCDR2

<400> SEQUENCE: 140

Asp Ile Tyr Pro Gly Gly Ala Tyr Thr Asn Tyr Asn Glu Lys Phe Lys
1               5                   10                  15

Asp

<210> SEQ ID NO 141
<211> LENGTH: 13
<212> TYPE: PRT
<213> ORGANISM: Artificial sequence
<220> FEATURE:
<223> OTHER INFORMATION: 1711 HCDR3

<400> SEQUENCE: 141

Gly Asp Tyr Tyr Asp Ser Ser Gly Arg Ala Met Asp Tyr
1               5                   10

<210> SEQ ID NO 142
<211> LENGTH: 17
<212> TYPE: PRT
<213> ORGANISM: Artificial sequence
<220> FEATURE:
<223> OTHER INFORMATION: 1711 LCDR1

<400> SEQUENCE: 142

Lys Ser Ser Gln Ser Leu Leu Tyr Ser Arg Asn Gln Met Asn Tyr Leu
1               5                   10                  15

Ala

<210> SEQ ID NO 143
<211> LENGTH: 7
<212> TYPE: PRT
<213> ORGANISM: Artificial sequence
<220> FEATURE:
<223> OTHER INFORMATION: 1711 LCDR2

<400> SEQUENCE: 143

Trp Thr Ser Thr Arg Glu Ser
1               5

<210> SEQ ID NO 144
<211> LENGTH: 9
<212> TYPE: PRT
<213> ORGANISM: Artificial sequence
```

```
<220> FEATURE:
<223> OTHER INFORMATION: 1711 LCDR3

<400> SEQUENCE: 144

Gln Gln Tyr Tyr Ser Tyr Pro Tyr Thr
1               5

<210> SEQ ID NO 145
<211> LENGTH: 119
<212> TYPE: PRT
<213> ORGANISM: Artificial sequence
<220> FEATURE:
<223> OTHER INFORMATION: 1708-VH1

<400> SEQUENCE: 145

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met His Trp Val Arg Gln Ala Pro Gly Gln Gly Leu Glu Trp Met
            35                  40                  45

Gly Arg Ile Asp Pro Asp Ser Thr Gly Ser Lys Tyr Asn Glu Lys Phe
        50                  55                  60

Lys Thr Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Ala Tyr Gly Tyr Tyr Phe Asp Tyr Trp Gly Gln Gly
            100                 105                 110

Thr Leu Val Thr Val Ser Ser
        115

<210> SEQ ID NO 146
<211> LENGTH: 119
<212> TYPE: PRT
<213> ORGANISM: Artificial sequence
<220> FEATURE:
<223> OTHER INFORMATION: 1708-VH2

<400> SEQUENCE: 146

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met His Trp Val Arg Gln Ala Pro Gly Gln Gly Leu Glu Trp Met
            35                  40                  45

Gly Arg Ile Asp Pro Asp Ser Thr Gly Ser Lys Tyr Asn Glu Lys Phe
        50                  55                  60

Lys Thr Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Ala Tyr Gly Tyr Tyr Phe Asp Tyr Trp Gly Gln Gly
            100                 105                 110

Thr Leu Val Thr Val Ser Ser
        115

<210> SEQ ID NO 147
<211> LENGTH: 119
```

<212> TYPE: PRT
<213> ORGANISM: Artificial sequence
<220> FEATURE:
<223> OTHER INFORMATION: 1708-VH3

<400> SEQUENCE: 147

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Ile
        35                  40                  45

Gly Arg Ile Asp Pro Asp Ser Thr Gly Ser Lys Tyr Asn Glu Lys Phe
    50                  55                  60

Lys Thr Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ala Tyr Gly Tyr Tyr Phe Asp Tyr Trp Gly Gln Gly
            100                 105                 110

Thr Leu Val Thr Val Ser Ser
        115

<210> SEQ ID NO 148
<211> LENGTH: 107
<212> TYPE: PRT
<213> ORGANISM: Artificial sequence
<220> FEATURE:
<223> OTHER INFORMATION: 1708-VL1

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Arg Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Tyr His Ser Gly Ser Pro Leu
                85                  90                  95

Pro Phe Gly Gly Gly Thr Lys Val Glu Ile Lys
            100                 105

<210> SEQ ID NO 149
<211> LENGTH: 107
<212> TYPE: PRT
<213> ORGANISM: Artificial sequence
<220> FEATURE:
<223> OTHER INFORMATION: 1708-VL2

<400> SEQUENCE: 149

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ser Pro Lys Leu Leu Ile

-continued

```
          35                40                45

Tyr Asn Ala Arg Thr Leu Ala Glu Gly Val Pro Ser Arg Phe Ser Gly
    50                55                60

Ser Gly Ser Gly Thr Asp Phe Thr Leu Thr Ile Ser Ser Leu Gln Pro
65                70                75                80

Glu Asp Phe Ala Thr Tyr Tyr Cys Gln Tyr His Ser Gly Ser Pro Leu
                85                90                95

Pro Phe Gly Gly Gly Thr Lys Val Glu Ile Lys
            100               105
```

```
<210> SEQ ID NO 150
<211> LENGTH: 13
<212> TYPE: PRT
<213> ORGANISM: Artificial sequence
<220> FEATURE:
<223> OTHER INFORMATION: 20 HCDR3

<400> SEQUENCE: 150

Gly Phe Lys Phe Asp Glu Asp Tyr Cys Ala Pro Asn Asp
1               5               10
```

```
<210> SEQ ID NO 151
<211> LENGTH: 12
<212> TYPE: PRT
<213> ORGANISM: Artificial sequence
<220> FEATURE:
<223> OTHER INFORMATION: 30 HCDR3

<400> SEQUENCE: 151

Gly Trp Thr Phe Gly Gly Gln Cys Ser Pro Ala Asp
1               5               10
```

```
<210> SEQ ID NO 152
<211> LENGTH: 10
<212> TYPE: PRT
<213> ORGANISM: Artificial sequence
<220> FEATURE:
<223> OTHER INFORMATION: Linker

<400> SEQUENCE: 152

Gly Gly Gly Gly Ser Gly Gly Gly Gly Ser
1               5               10
```

```
<210> SEQ ID NO 153
<211> LENGTH: 229
<212> TYPE: PRT
<213> ORGANISM: Artificial sequence
<220> FEATURE:
<223> OTHER INFORMATION: Fc region of human IgG4 heavy chain
      (S228P/K447A)

<400> SEQUENCE: 153

Glu Ser Lys Tyr Gly Pro Pro Cys Pro Pro Cys Pro Ala Pro Glu Phe
1               5               10                15

Leu Gly Gly Pro Ser Val Phe Leu Phe Pro Pro Lys Pro Lys Asp Thr
            20                25                30

Leu Met Ile Ser Arg Thr Pro Glu Val Thr Cys Val Val Val Asp Val
        35                40                45

Ser Gln Glu Asp Pro Glu Val Gln Phe Asn Trp Tyr Val Asp Gly Val
    50                55                60

Glu Val His Asn Ala Lys Thr Lys Pro Arg Glu Glu Gln Phe Asn Ser
65                70                75                80
```

-continued

```
Thr Tyr Arg Val Val Ser Val Leu Thr Val Leu His Gln Asp Trp Leu
             85                  90                  95

Asn Gly Lys Glu Tyr Lys Cys Lys Val Ser Asn Lys Gly Leu Pro Ser
            100             105             110

Ser Ile Glu Lys Thr Ile Ser Lys Ala Lys Gly Gln Pro Arg Glu Pro
        115             120             125

Gln Val Tyr Thr Leu Pro Pro Ser Gln Glu Glu Met Thr Lys Asn Gln
    130             135             140

Val Ser Leu Thr Cys Leu Val Lys Gly Phe Tyr Pro Ser Asp Ile Ala
145             150             155                 160

Val Glu Trp Glu Ser Asn Gly Gln Pro Glu Asn Asn Tyr Lys Thr Thr
            165             170             175

Pro Pro Val Leu Asp Ser Asp Gly Ser Phe Phe Leu Tyr Ser Arg Leu
            180             185             190

Thr Val Asp Lys Ser Arg Trp Gln Glu Gly Asn Val Phe Ser Cys Ser
            195             200             205

Val Met His Glu Ala Leu His Asn His Tyr Thr Gln Lys Ser Leu Ser
    210             215             220

Leu Ser Leu Gly Lys
225
```

```
<210> SEQ ID NO 154
<211> LENGTH: 4
<212> TYPE: PRT
<213> ORGANISM: Artificial Sequence
<220> FEATURE:
<223> OTHER INFORMATION: Linker

<400> SEQUENCE: 154

Ala Ser Gly Ser
1
```

```
<210> SEQ ID NO 155
<211> LENGTH: 5
<212> TYPE: PRT
<213> ORGANISM: Artificial Sequence
<220> FEATURE:
<223> OTHER INFORMATION: G4S Linker

<400> SEQUENCE: 155

Gly Gly Gly Gly Ser
1               5
```

```
<210> SEQ ID NO 156
<211> LENGTH: 15
<212> TYPE: PRT
<213> ORGANISM: Artificial Sequence
<220> FEATURE:
<223> OTHER INFORMATION: (G4S)3 Linker

<400> SEQUENCE: 156

Gly Gly Gly Gly Ser Gly Gly Gly Gly Ser Gly Gly Gly Gly Ser
1               5                   10                  15
```

```
<210> SEQ ID NO 157
<211> LENGTH: 20
<212> TYPE: PRT
<213> ORGANISM: Artificial Sequence
<220> FEATURE:
<223> OTHER INFORMATION: (G4S)4 Linker

<400> SEQUENCE: 157
```

-continued

```
Gly Gly Gly Gly Ser Gly Gly Gly Gly Ser Gly Gly Gly Gly Ser Gly
1               5                   10                  15

Gly Gly Gly Ser
        20

<210> SEQ ID NO 158
<211> LENGTH: 25
<212> TYPE: PRT
<213> ORGANISM: Artificial Sequence
<220> FEATURE:
<223> OTHER INFORMATION: (G4S)5 Linker

<400> SEQUENCE: 158

Gly Gly Gly Gly Ser Gly Gly Gly Gly Ser Gly Gly Gly Gly Ser Gly
1               5                   10                  15

Gly Gly Gly Ser Gly Gly Gly Gly Ser
        20                  25

<210> SEQ ID NO 159
<211> LENGTH: 30
<212> TYPE: PRT
<213> ORGANISM: Artificial Sequence
<220> FEATURE:
<223> OTHER INFORMATION: (G4S)6 Linker

<400> SEQUENCE: 159

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
        20                  25                  30

<210> SEQ ID NO 160
<211> LENGTH: 5
<212> TYPE: PRT
<213> ORGANISM: Artificial Sequence
<220> FEATURE:
<223> OTHER INFORMATION: YGNGT Linker

<400> SEQUENCE: 160

Tyr Gly Asn Gly Thr
1               5

<210> SEQ ID NO 161
<211> LENGTH: 10
<212> TYPE: PRT
<213> ORGANISM: Artificial Sequence
<220> FEATURE:
<223> OTHER INFORMATION: (YGNGT)2 Linker

<400> SEQUENCE: 161

Tyr Gly Asn Gly Thr Tyr Gly Asn Gly Thr
1               5                   10

<210> SEQ ID NO 162
<211> LENGTH: 15
<212> TYPE: PRT
<213> ORGANISM: Artificial Sequence
<220> FEATURE:
<223> OTHER INFORMATION: (YGNGT)3 Linker

<400> SEQUENCE: 162

Tyr Gly Asn Gly Thr Tyr Gly Asn Gly Thr Tyr Gly Asn Gly Thr
1               5                   10                  15

<210> SEQ ID NO 163
```

```
<211> LENGTH: 20
<212> TYPE: PRT
<213> ORGANISM: Artificial Sequence
<220> FEATURE:
<223> OTHER INFORMATION: (YGNGT)4 Linker

<400> SEQUENCE: 163

Tyr Gly Asn Gly Thr Tyr Gly Asn Gly Thr Tyr Gly Asn Gly Thr Tyr
1               5                   10                  15

Gly Asn Gly Thr
            20

<210> SEQ ID NO 164
<211> LENGTH: 25
<212> TYPE: PRT
<213> ORGANISM: Artificial Sequence
<220> FEATURE:
<223> OTHER INFORMATION: (YGNGT)5 Linker

<400> SEQUENCE: 164

Tyr Gly Asn Gly Thr Tyr Gly Asn Gly Thr Tyr Gly Asn Gly Thr Tyr
1               5                   10                  15

Gly Asn Gly Thr Tyr Gly Asn Gly Thr
            20                  25

<210> SEQ ID NO 165
<211> LENGTH: 30
<212> TYPE: PRT
<213> ORGANISM: Artificial Sequence
<220> FEATURE:
<223> OTHER INFORMATION: (YGNGT)6 Linker

<400> SEQUENCE: 165

Tyr Gly Asn Gly Thr Tyr Gly Asn Gly Thr Tyr Gly Asn Gly Thr Tyr
1               5                   10                  15

Gly Asn Gly Thr Tyr Gly Asn Gly Thr Tyr Gly Asn Gly Thr
            20                  25                  30

<210> SEQ ID NO 166
<211> LENGTH: 5
<212> TYPE: PRT
<213> ORGANISM: Artificial Sequence
<220> FEATURE:
<223> OTHER INFORMATION: (GGNGT)x Linker
<220> FEATURE:
<221> NAME/KEY: MISC_FEATURE
<222> LOCATION: (1)..(5)
<223> OTHER INFORMATION: The entire sequence of amino acids 1-5 can be
      repeated one or more times.

<400> SEQUENCE: 166

Gly Gly Asn Gly Thr
1               5

<210> SEQ ID NO 167
<211> LENGTH: 5
<212> TYPE: PRT
<213> ORGANISM: Artificial Sequence
<220> FEATURE:
<223> OTHER INFORMATION: (YGNGT)x Linker
<220> FEATURE:
<221> NAME/KEY: MISC_FEATURE
<222> LOCATION: (1)..(5)
<223> OTHER INFORMATION: The entire sequence of amino acids 1-5 can be
      repeated one or more times.

<400> SEQUENCE: 167
```

-continued

```
Tyr Gly Asn Gly Thr
1               5

<210> SEQ ID NO 168
<211> LENGTH: 5
<212> TYPE: PRT
<213> ORGANISM: Artificial Sequence
<220> FEATURE:
<223> OTHER INFORMATION: (G4S)x Linker
<220> FEATURE:
<221> NAME/KEY: MISC_FEATURE
<222> LOCATION: (1)..(5)
<223> OTHER INFORMATION: The entire sequence of amino acids 1-5 can be
      repeated one or more times.

<400> SEQUENCE: 168

Gly Gly Gly Gly Ser
1               5
```